US009556206B2

(12) United States Patent
Toutov et al.

(10) Patent No.: US 9,556,206 B2
(45) Date of Patent: Jan. 31, 2017

(54) BASE-CATALYZED SILYLATION OF TERMINAL ALKYNE C—H BONDS

(71) Applicant: CALIFORNIA INSTITUTE OF TECHNOLOGY, Pasadena, CA (US)

(72) Inventors: Anton Toutov, Pasadena, CA (US); Kerry Betz, Boulder, CO (US); Brian M. Stoltz, San Marino, CA (US); Wenbo Liu, Pasadena, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/841,964

(22) Filed: Sep. 1, 2015

(65) Prior Publication Data
US 2016/0060278 A1 Mar. 3, 2016

Related U.S. Application Data

(60) Provisional application No. 62/044,754, filed on Sep. 2, 2014, provisional application No. 62/146,541, filed on Apr. 13, 2015, provisional application No. 62/172,969, filed on Jun. 9, 2015.

(51) Int. Cl.
C07F 7/08 (2006.01)
C07J 7/00 (2006.01)
C07J 1/00 (2006.01)
C07J 51/00 (2006.01)

(52) U.S. Cl.
CPC ............ *C07F 7/0827* (2013.01); *C07J 1/0096* (2013.01); *C07J 51/00* (2013.01)

(58) Field of Classification Search
CPC ......... C07F 7/0827; C07J 1/0096; C07J 51/00

USPC ....... 556/11, 413, 430, 481; 552/505; 549/4; 548/110; 546/14
See application file for complete search history.

(56) References Cited

U.S. PATENT DOCUMENTS

| 3,137,718 | A | * | 6/1964 | Jenkner | C07F 5/00 528/34 |
| 4,360,686 | A | | 11/1982 | Wang et al. | |
| 4,363,925 | A | | 12/1982 | Acker et al. | |
| 5,516,908 | A | | 5/1996 | Freyne et al. | |
| 9,000,167 | B2 | * | 4/2015 | Grubbs | C07F 7/0818 546/14 |

(Continued)

FOREIGN PATENT DOCUMENTS

WO WO 2014/055587 A1 4/2004

OTHER PUBLICATIONS

Anastas, et al., "Origins, Current Status, and Future Challenges of Green Chemistry", Chem. Res. 2002, vol. 35(9), 686-694.

(Continued)

Primary Examiner — Porfirio Nazario Gonzalez
(74) Attorney, Agent, or Firm — Baker & Hostetler LLP

(57) ABSTRACT

The present invention is directed to a mild, efficient, and general direct C(sp)-H bond silylation. Various embodiments includes methods, each method comprising or consisting essentially of contacting at least one organic substrate comprising a terminal alkynyl C—H bond, with a mixture of at least one organosilane and an alkali metal hydroxide, under conditions sufficient to form a silylated terminal alkynyl moiety. The methods are operable in the substantially absence of transition-metal compounds. The systems associated with these methods are also disclosed.

24 Claims, 10 Drawing Sheets
(10 of 10 Drawing Sheet(s) Filed in Color)

(56) References Cited

U.S. PATENT DOCUMENTS

| | | | | |
|---|---|---|---|---|
| 2014/0228588 | A1* | 8/2014 | Masumoto | A01N 37/52 556/413 |
| 2015/0005518 | A1* | 1/2015 | Gutierrez Fuentes | C07J 7/00 552/505 |
| 2015/0166579 | A1* | 6/2015 | Grubbs | C07F 7/0818 546/14 |
| 2016/0046653 | A1* | 2/2016 | Toutov | C07F 7/0801 528/380 |

OTHER PUBLICATIONS

Andreev, et al., "Direct Electrophilic Silylation of Terminal Alkynes", Organic Letters, Jan. 15, 2004, vol. 6(3), 421-424.
Bergman, et al., Organometallic chemistry: C—H activation, Nature, Mar. 2007, vol. 446, 391-393.
Cheng, et al., "Rhodium-Catalyzed Intermolecular C—H Silylation of Arenes with High Steric Regiocontrol", Science, Feb. 21, 2014, vol. 343, 853-857.
Cheng, et al., "Synthesis of Conjugated Polymers for Organic Solar Cell Applications", Chem. Rev., Sep. 2009, vol. 109(11), 5868-5923.
Clark, et al., "Green Chemistry: Challenges and Opportunities", Green Chem., Feb. 1999, vol. 1, 1-8.
Dudziec, et al., "New Catalytic Route to Monoalkynyl-Functionalized Di and Trivinyl-Substituted Cyclosiloxanes and Divinylcyclosilazanes", Organometallics, Oct. 2008, vol. 27(21), 5598-5604.
Eaborn, Cleavages of Aryl-Silicon and Related Bonds by Electrophiles, J. Organomet. Chem., Oct. 1975, vol. 100(1), 43-57.
Fujiki, "Optically Active Polysilanes. Ten Years of Progress and New Polymer Twist for Nanoscience and Nanotechnology", Polymer Journal, 2003, vol. 35(4), 297-344.
Godula, et al., "C—H Bond Functionalization in Complex Organic Synthesis", Science, 2006, vol. 312, 67-72.
Li, et al., "Green Chemistry for Chemical Synthesis", Proc. Natl. Acad. Sci., Sep. 2008, vol. 105(36), 13197-13202.
Li, et al., "Green chemistry: The Development of Cross-Dehydrogenative Coupling (CDC) for Chemical Synthesis", Pure Appl., 2006, Chem. 78(5), 935-945.
Lu, et al., "Efficient Iridium-Catalyzed C—H Functionalization/Silylation of Heteroarenes", Angew. Chem. Int., Aug. 2008, Ed., vol. 47, 7508-7510.
Oyamada, et al., "Scandium-Catalyzed Silylation of Aromatic C—H bonds", Angew. Chem. Int. Ed., Sep. 20, 2011, vol. 50, 10720-10723.
Rahaim, et al., "Zinc-Catalyzed Silylation of Terminal Alkynes", J. Org. Chem., Mar. 11, 2008, vol. 73, 2912-2915.
Scheuermann, "Beyond Traditional Cross Couplings: The Scope of the Cross Dehydrogenative Coupling Reaction", Chem. Asian J., Dec. 2009, vol. 5, 436-451.
Shimizu, et al., "Dehydrogenative Silylation of Terminal Alkynes by Iridium Catalyst", Tet. Lett., 2000, vol. 41, 907-910.
Sugita, et al., "A Novel Reduction of Zinc(II) Chloride with Samarium Metal and its Application to Silylation of 1-Alkynes. Synlett", 1996, vol. 7, 637-639.
Toutov, et al. "Silylation of C—H bonds in Aromatic Heterocycles by an Earth-Abundant Metal Catalyst", Nature, Feb. 2015, vol. 518, 80-84.
Tsuchimoto, et al., "Dehydrogenative Silylation of Terminal Alkynes with Hydrosilanes under Zinc-Pyridine Catalysis", Adv. Synth. Catal., 2012, vol. 354, 2959-2964.
Voronkov, et al., "Dehydrocondensation of Trialkylsilanes with Acetylene and Monosubstituted Acetylenes", J. Organomet. Chem., 1984, vol. 264, 39-48.
Wang, et al., "Unique σ-Bond Metathesis of Silylalkynes Promoted by an ansa-Dimethylsilyl and Oxo-Bridged Uranium Metallocene", J. Am. Chem. Soc., Jun. 2006, vol. 128(29), 9350-9351.

Weickgenannt, et al., "Potassium tert-Butoxide-Catalyzed Dehydrogenative Si—O Coupling: Reactivity Pattern and Mechanism of an Underappreciated Alcohol Protection", Chem. Asian J., 2009, vol. 4, 406-410.
Dervan, et al., "Trimethylsilylpotassium. Deoxygenation of Epoxides With Inversion of Stereochemistry", J. Am. Chem. Soc., 1976, vol. 98, 1265-1267.
Haebich, et al., "Preparation of Aryl- and Heteroaryltrimethylsilanes", Synthesis, 1979, Issue 11, 841-876.
Kyalo, et al., "Palladium-catalyzed Direct C—H Silylation and Germanylation of Benzamides and Carboxamides", Org. Lett., 2014, vol. 16, 1968-1971.
Shippey, et al., "Trimethylsilyl Anions. Direct Synthesis of Trimethylsilybenzenes", J. Org. Chem., 1977, vol. 42, 2654-2655.
Aikawa, et al., "Highly Enantioselective Alkynylation of Trifluoropyruvate with Alkynylsilanes Catalyzed by the BINAP-Pd Complex: Access to a-Trifluoromethyl-Substituted Tertiary Alcohols", Org. Lett., Nov. 16, 2010, 12(24), 5716-5719.
Babudri, et al., "A Straightforward Route to Polyenylsilanes by Palladium-Catalyzed or Nickel-Catalyzed Cross-Coupling Reactions", Tetrahedron, 1998, 54(7),1085-1094.
Ball et al., "Gold-Catalyzed Direct Arylation", Science, Sep. 28, 2012, vol. 337, 1644-1648.
Bekele et al., "Improved Synthesis of the Boc and Fmoc Derivatives of 4-(2'-Aminoethyl)-6-dibenzofuranpropionic Acid: An Unnatural Amino Acid That Nucleates β-Sheet Folding", Journal of Organic Chemistry, 1997, 62(7), 2259-2262.
Cheve et al., "De novo Design, synthesis and pharmacological evaluation of new azaindole derivatives as dual inhibitors of Abl and Src kinases", Med. Chem. Comm., Jun. 2012, 3, 7, 788-800.
Chinchilla, et al., "Recent Advances in Sonogashira Reactions", Chem. Soc. Rev., Mar. 18, 2011, 40, 5084-5121.
Diez-Gonzalez et al., "Copper, Silver and Gold Complexes in Hydrosilyation Reactions", Accts. Chem Res., Feb. 2008, 41 (2), 349-358.
Franz, et al., "Organosilicon Molecules with Medicinal Applications", J. Med. Chem., Jan. 2013, 56(2), 388-405.
Gleiter, et al., "Alkynes Between Main Group Element: From Dumbbells via Rods to Squares and Tubes", Chem. Rev., Apr. 14, 2010, 110, 4447-88.
Häbich et al., "Preparation of Aryl- and Heteroaryltrimethylsilanes", Reviews, Nov. 1979, 841-876.
Ishikawa, et al., "Dehydrogenative Coupling Between Hydrosilanes and Alkynes Catalyzed by Alkoxided, Alkylmetals, and Metalamides", Journ. of Catalysis, Apr. 16, 1999, 185,454-61.
Isogai, et al., "CUX$_2$-Mediated [4+2] Benzannulation as a New Synthetic Tool for Stereoselective Construction of Haloaromatic Compounds", Tetrahedron, 65, Sep. 2009, 9575-82.
Itami, et al., "2-Pyridylsilyl Group: A Useful Multifunctional Group in Organic Synthesis", Synlett, Dec. 2005, 2, 157-180.
Itoh, "Disproportionation Reactions of Organohydrosilanes in the Presence of Base Catalysts", Journ. of Organo Metalic Chem., 629, Feb. 2001, 1-6.
Itoh, et al., "Dehydrogenative Coupling Reactions Between Hydrosilanes and Monosubstituted Alkynes Catalyzed by Solid Bases", Journ. of Organo. Chem., 476, 1994, C30-C31.
Kaur, et al., "(NHC)Cu1 (NHC=N-Heterocyclic Carbene) Complexes as Efficient Catalysts for the Reduction of Carbonyl Compounds", Organometallics, Feb. 2004, 23, 1157-1160.
Keaton, et al., "Titanium(II)-Mediated Cyclization of (Silyloxy)enynes: A Total Synthesis of (−)-7-Demethylpiericidin A$_1$", JACS, Dec. 17, 2005, 408-409.
Kim, et al., "Regio- and Stereoselective Enyne Cross Metathesis of Silylated Internal Alkynes", JACS, Aug. 3, 2004, 10242-43.
Konigs et al., "Base-Free Dehydrogenative Coupling of Enolizable Carbonyl Compounds With Silanes", Org. Lett., May 2012, 14(11), 2842-2845.
Kuznetsov et al., "General and Practical One-Pot Synthesis of Dihydrobenzosiloles rom Styrenes", Org. Lett., Jan. 2012, 14(3), 914-917.

(56) References Cited

OTHER PUBLICATIONS

Marsden, et al. Structure-Property Relationships of Donor Acceptor-Functionalized Tetrakis(phenylethynyl)benzenes and Bis(dehydrobenzoannuleno)benzenes, J. Am. Chem. Soc., Feb. 2005, 2464-76.

Mita, et al., "Sequential Protocol for C(sp$^3$)-H Carboxylation with $CO_2$: Transition-Metal-Catalyzed Benzylic C—H Silylation and Fluoride-Mediated Carboxylation", Jun. 2012, vol. 14(13), 3462-3465.

Miyaura, "Organoboron Compounds", Top. Curr. Chem., Jan. 2002, 219, 11-59.

Miyaura, et al., "Palladium-Catalyzed Cross-Coupling Reactions of Organoboron Compounds", A. Chem. Rev. 1995, 95(7), 2457-2483.

Mu, et al. "Silicon-Based Building Blocks for One-Step $^{18}$F-Radiolabeling of Peptides for PET Imagin", Angew Chem., 2008, 47, 4922-25.

Nishihara, et al., "Palladium/copper-Catalyzed Sila-Sonogashira Reactions of Aryl Iodides with Alkynylsilanes via a Direct C—Si Bond Activation", Tetrahedron Letters 50, Jun. 2009, 4643-4646.

Park et al., "Transition Metal-Catalyzed Ortho-Functionalization in Organic Synthesis", Bull. Korean Chem. Soc., 2005, vol. 26, No. 6, 871-877.

Park, et al., "Gold-Catalyzed Intramolecular Allylation of Silyl Alkynes Induced by Silane Alcoholysis" JACS, 128, 10664-10665, Jul. 28, 2006, 10664-65.

Rychnovsky et al., "Synthesis of Optically Pure Arylsilylcarbinols and Their Use as Chiral Auxiliaries in Oxacarbenium Ion Reactions", Journal of Organic Chemistry, Dec. 2003, 68, 10135-10145.

Showell, et al., "Chemistry Challenges in Lead Optimization: Silicon Isosteres in Drug Discovery", Drug Discovery, vol. 8(12), Jun. 2003, 551-556.

Starkov, et al., "Catalytic Electrophilic Halogenation of Siyl-Protected and Terminal Alkynes: Trapping Gold (I) Acetylides vs. a Bronsted Acid-Promoted Reaction", Adv. Synth. Catal., Nov. 2012, 354, pp. 3217-3224.

Ulrich, et al., "Elektrophile Silyberung Elektronemrelcher Heteroaromaten", Synthesis, Nov. 1984, 929-930.

Wang, et al., "Transition-Metal-Free Synthesis of Alternating Thiophene-Perfluroarene Copolymers", Feb. 3, 2006, 2536-2537.

Yamaguchi, et al., "Heterogeneously Catalyzed Aerobic Cross-Dehydrogenative Coupling of Terminal Alkynes and Monohydrosilanes by Gold Supported on OMS-2", Angew Chem., 2013, 52, 5627-30.

Zhao, et al., Directed ortho Metalation-Based Methodology. Halo-, Nitroso-, and Boro-Induced *ipso*-Desilylation. Link to an in situ Reaction, May 20, 2005, vol. 7(13), 2523-2526.

\* cited by examiner

FIG. 1
a. Previous investigations: KOt-Bu-catalyzed (hetero)aromatic C–H silylation
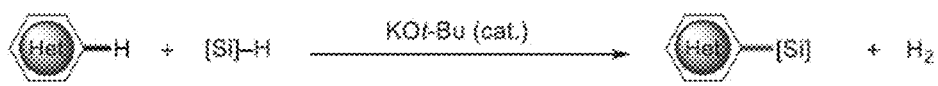
b. This study: catalytic silylation of non-aromatic C–H bonds by alkali metal hydroxides
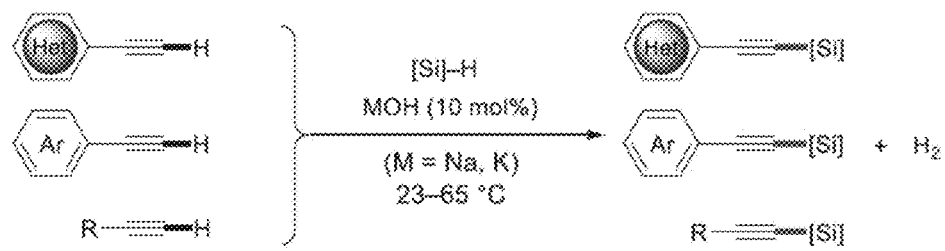

FIG. 2

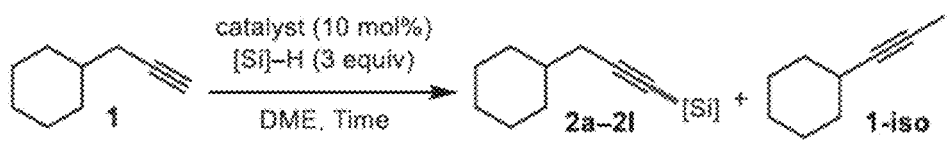

| Entry | Catalyst | [Si]–H | T | Time | Yield 2 | Yield 1-iso |
|---|---|---|---|---|---|---|
| a Optimization of reaction conditions ||||||||
| 1 | KOt-Bu | Et₃SiH | 85 °C | 24 h | 2a (89%) | 9% |
| 2 | NaOt-Bu | Et₃SiH | 85 °C | 24h | 2a (46%) | 52% |
| 3 | LiOt-Bu | Et₃SiH | 85 °C | 24h | 2a (<1%) | – |
| 4 | DABCO | Et₃SiH | 85 °C | 48h | – | – |
| 5 | Pyridine | Et₃SiH | 85 °C | 48h | 2a (1%) | – |
| 6 | Et₃N | Et₃SiH | 85 °C | 48h | 2a (4%) | – |
| 7 | KOH | Et₃SiH | 85 °C | 24h | 2a (95%) | 3% |
| 8 | KOH | PhMe₂Si–H | 25 °C | 48h | 2b (89%) | – |
| 9 | NaOH | PhMe₂Si–H | 25 °C | 48h | 2b (93%) | – |
| 10 | LiOH | PhMe₂Si–H | 25 °C | 48h | – | – |
| b Scope of the hydrosilane ||||||||
| 11 | KOH | EtMe₂Si–H | 45 °C | 24h | 2c (93%) | – |
| 12 | KOH | nBu₃Si–H | 65 °C | 48h | 2d (73%) | – |
| 13 | KOH | Et₂HSi–H | 25 °C | 24h | 2e (71%) | – |
| 14 | NaOH | tBu₂HSi–H | 65 °C | 48h | 2f (91%) | – |
| 15 | NaOH | BnMe₂Si–H | 45 °C | 48h | 2g (75%) | – |
| 16 | KOH | (iPr)₃Si–H | 85 °C | 48h | 2h (69%) | – |
| 17 | NaOH | (OEt)₃Si–H | 65 °C | 48h | 2i (68%) | – |
| 18 | KOH | (iPr)₂PySi–H | 65 °C | 48h | 2j (78%) | – |
| 19 | NaOH | Me₂PySi–H | 65 °C | 48h | 2k (78%) | – |
| 20 | NaOH | Me₃Si–SiMe₂–H | 25 °C | 48h | 2l (95%) | – |

| Entry | Product | | Yield KOH | Yield NaOH |
|---|---|---|---|---|
| 1 | | [Si] = EtMe₂ (2c) | 81% | 14% |
| 2 | | = SinBu₃ (2d) | 73% | 22% |
| 3 | | = SiEt₂H (2e) | 71% | 46% |
| 4 | | = Si(iPr)₃ (2h) | 68% | 0% |
| 5 | | = Si(iPr)₂Py (2j) | 78% | 0% |
| 6 | | = SiMe₂Bn (2g) | 0% | 75% |
| 7 | | = Si(OEt)₃ (2i) | 0% | 68% |
| 8 | | = SiMe₂-SiMe₃ (2l) | 0% | 85% |

FIG. 6 (cont'd)
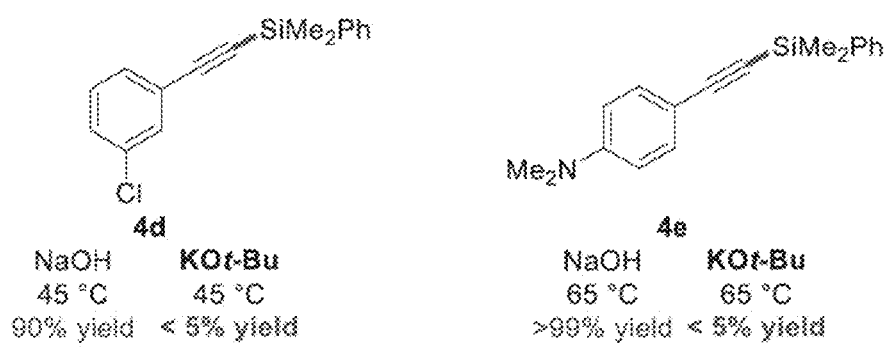
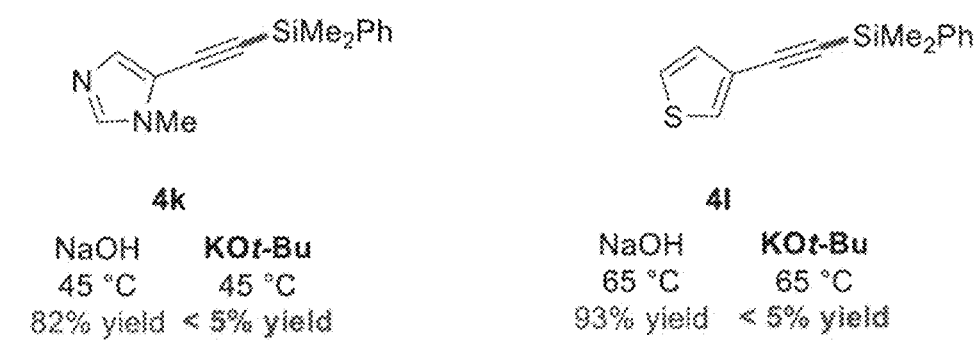
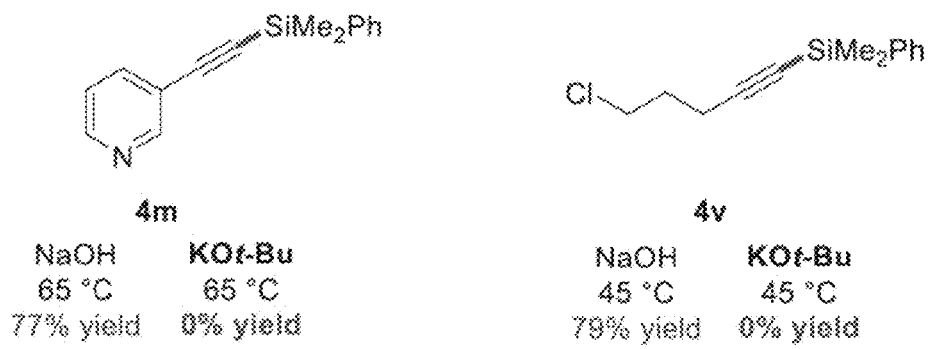

BASE-CATALYZED SILYLATION OF TERMINAL ALKYNE C—H BONDS

CROSS REFERENCE TO RELATED APPLICATIONS

This application claims the benefit of priority to U.S. Patent Application Ser. Nos. 62/044,754, filed Sep. 2, 2014; 62/146,541, filed Apr. 13, 2015; and 62/172,969, filed Jun. 9, 2015, the contents of which are incorporated by reference herein for all purposes.

GOVERNMENT RIGHTS

This invention was made with government support under Grant No. CHE1212767 awarded by the National Science Foundation. The government has certain rights in the invention.

TECHNICAL FIELD

The present invention is directed at methods for silylating alkyne substrates—i.e., containing terminal alkyne C(sp)-H bonds—using alkali metal hydroxide, alkoxide, or hydride catalysts and organosilane reagents.

BACKGROUND

The ability to silylate organic moieties has attracted significant attention in recent years, owing to the utility of the silylated materials in their own rights or as intermediates for other important materials used, for example, in agrichemical, pharmaceutical, and electronic material applications.

Over the past several decades, considerable effort has been allocated to the development of powerful catalyst architectures to accomplish a variety of C—H functionalization reactions, revolutionizing the logic of chemical synthesis and consequently streamlining synthetic chemistry. Accomplishing such challenging transformations can often necessitate the use of stoichiometric additives, demanding reaction conditions, complex ligands, and most notably precious metal precatalysts. Notably, the need to use precious metal catalysts for these transformations remains a fundamental and longstanding limitation.

Strategies for the synthesis of ethynylsilanes have employed strong bases or have relied on stoichiometric or catalytic transition metal species such as Pt, Zn, Au, and Ir, typically using various pre-activated organosilicon coupling partners at high temperatures. Inexpensive and commercially available hydrosilanes have been investigated, however this particular silicon source has introduced new challenges: the requisite in situ Si—H bond activation necessitates exogenous bases, sacrificial hydrogen acceptors or oxidants, and elevated temperatures (i.e., 80-120° C.). Moreover, undesired hydrosilylation of the alkyne can be competitive, further complicating catalyst and reaction design. These factors have led to important limitations in scope and practical utility. For example, substrate classes important in pharmaceuticals and natural products applications such as aliphatic amines and nitrogen heterocycles are notably absent in the aforementioned reports. Despite the inherent acidity of terminal acetylenes, the development of a mild and general stoichiometric or catalytic method for cross-dehydrogenative C(sp)-Si bond formation remains a longstanding challenge in the field.

The present invention takes advantage of the discoveries cited herein to avoid at least some of the problems associated with previously known methods.

SUMMARY

Herein is disclosed a mild, efficient, and general direct C(sp)-H bond silylation. The catalytic cross-dehydrogenative method avoids the limitations of previous strategies and successfully couples alkynes and hydrosilanes previously unprecedented in C—H silylation on multi-gram scale and with high yield and excellent chemoselectivity. Remarkably, the catalysts can be KOH and NaOH.

Various embodiments includes methods, each method comprising or consisting essentially of contacting at least one organic substrate comprising a terminal alkynyl C—H bond, with a mixture of at least one organosilane and an alkali metal hydroxide, alkoxide, or hydride (hydroxide preferred), under conditions sufficient to form a silylated terminal alkynyl moiety. Such methods are operable in the substantial absence of transition metal compounds, or other electromagnetic or thermal initiation or propagation.

In some embodiments, the organosilane comprises an organosilane of Formula (I), Formula (II), or Formula (III):

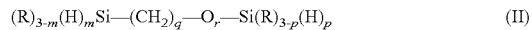

where R is flexibly defined, m and p are independently 1, 2, or 3; q is 0, 1, 2, 3, 4, 5, or 6; r is 0 or 1; and n is 10 to 100. In some embodiments, for example, the organosilane is independently $(R)_3SiH(R)_2SiH_2$, or $(R)SiH_3$. In some embodiments for Formula (II), q is 0. In some embodiments for Formula (II), r is 0. In some embodiments, R is independently alkoxy, alkyl, alkenyl, aryl, aryloxy, heteroaryl, aralkyl, or heteroaralkyl.

In some embodiments, the alkali metal hydroxide is sodium hydroxide (NaOH) or potassium hydroxide (KOH). In some embodiments, the alkali metal alkoxide is sodium alkoxide (e.g., NaOMe, NaOEt, NaO-t-Bu) or potassium alkoxide (e.g., KOMe, KOEt, KO-t-Bu, KO-t-amyl). In some embodiments, the alkali metal hydride is sodium hydride (NaH) or potassium hydride (KH).

The organic substrate is typically defined as having at least one terminal alkynyl C—H bond having a formula:

where $R^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene. The methods are operable with a wide array of substrates defined in this way. Compounds having two or more terminal alkyne C—H bonds also provide silylated products, generally in discrete, sequential reactions. The substrates include individual chemical compounds, oligomers, and polymers.

In certain embodiments employing silanes having two or three Si—H bonds (e.g., $R_2SiH_2$ or $(R)SiH_3$), contacting a second or third organic substrate comprising a terminal alkynyl C—H bond with the silylated terminal alkynyl moiety, either at the same time or sequentially, can form a di- or tri-alkynyl silane product.

Once formed, the silylated terminal alkynyl moiety can be subject to a variety of known chemical reactions, and methods employing these known methods, when coupled with the inventive methods described here, are considered to be within the scope of the present invention. For example, when coupled with the inventive silylating methods described herein, at least one of the following subsequent reactions are within scope: (a) reacting the silylated terminal alkynyl moiety with another unsaturated moiety in a [2+2] or [4+2] cycloaddition reaction to form an aromatic, heteroaromatic, cycloalkenyl, or heterocycloalkenyl moiety; (b) reacting the silylated terminal alkynyl moiety with a second, unsaturated organic moiety in a cross-metathesis reaction to form a diolefin or polyolefin product; (c) polymerizing the silylated terminal alkynyl moiety; (d) reacting the silylated terminal alkynyl moiety with an organic azide a [3+2] azide-alkyne cycloaddition reaction (generally referred to as "Click chemistry," including 1,3-dipolar cycloadditions; (e) hydrogenating the silylated terminal alkynyl moiety; (f) removing the silyl group originally added to the terminal alkynyl C—H bond, such that the silylation functions as a blocking group for other transformations; (g) reacting the silylated terminal alkynyl moiety with an aromatic halide compound under conditions sufficient to form an alkynyl-arene linkage; and (h) reacting the silylated terminal alkynyl moiety with an N-halosuccinimide in the presence of a cationic gold catalyst to produce a terminal alkynyl halide.

Additionally, in the case wherein the at least one organosilane comprises an optionally substituted $C_{1-12}$ alkenyl or heteroalkenyl, such that the silylated terminal alkynyl moiety comprises a silicon bonded optionally substituted $C_{1-12}$ alkenyl or heteroalkenyl, certain embodiments include those methods further comprising reacting the silylated terminal alkynyl moiety with an alcohol and a catalyst under conditions to result in the intramolecular allylation of the silylated terminal alkynyl moiety Additionally, in the case wherein the at least one organosilane comprises a 2-pyridinyl group (as exemplifed herein by $(Me)_2$(pyridinyl)SiH or $(i-Pr)_2$(pyridinyl)SiH), the method further comprising reacting the silylated terminal alkynyl moiety with a copper carbomagnesation catalyst and an optionally substituted aryl or optionally substituted heteroaryl magnesium complex under conditions sufficient to carbomagnesate the silylated terminal alkynyl moiety. Still further embodiments provide reacting the carbomagnesated silylated terminal alkynyl moiety with an optionally substituted aryl iodide or optionally substituted heteroaryl iodide in the presence of a palladium catalyst to form a trisubstituted silylated olefin. And still further embodiments include those where the trisubstituted silylated olefin is reacted with $BCl_3$ and pinacol under conditions sufficient to borodesilylate the compound, and then optionally reacting the borodesilylated compound with a second optionally substituted aryl iodide or optionally substituted heteroaryl iodide under conditions suitable to cross-couple the resulting C—B bond and the second optionally substituted aryl iodide or optionally substituted heteroaryl iodide.

Still further embodiments include those systems for silylating an organic substrate comprising a terminal alkynyl C—H bond, said system comprising or consisting essentially of a mixture of (a) at least one organosilane and (b) an alkali metal hydroxide, alkoxide, or hydride, and (c) at least one substrate. The systems are described at least in terms as sufficient to accommodate the methods described herein. In some embodiments, the system further comprises the presence of a silylated terminal alkyne derived from the reaction between the substrate and the at least one organosilane.

While the embodiments are described mainly in terms of methods and systems for affecting these transformations, it should be appreciated that any compound derived from these methods and systems, which are not otherwise accessible by other practicable means, are considered within the scope of this invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 1 illustrates the range of catalytic C—H silylations now available by Earth-abundant metal salts. a, Recently disclosed KOt-Bu catalyzed C—H silylation of N-, O-, and S-containing aromatic heterocycles with high regiocontrol. b, Alkali metal hydroxides catalyze the cross-dehydrogenative silylation of nonaromatic C(sp)-H bonds.

FIG. 2 illustrates a subset of the optimization reaction conditions and the scope of utility with respect to the hydrosilane. For Entries 1-6, 8, and 10, yields were determined by GC-FID analysis using tridecane as an internal standard. For Entries 7, 9, and 11-20, yields were of analytically pure isolated materials. Reactions were conducted on 0.5 mmol scale with 0.5 mL of solvent at the prescribed temperature and time. DME=1,2-dimethoxyethane; DABCO=diazabicyclo[2.2.2]octane; $(iPr)_2PySi$—H=2-diisopropylsilyl pyridine; $Me_2PySi$—H=2-dimethylsilyl pyridine.

FIG. 4A provides a scheme for the multigram synthesis of unbiased ethynylsilane building block 2a. FIG. 4B shows the step-wise reactivity of symmetrical terminal diynes in both the alkyl- and aryl series can be selectively mono- or bis-functionalized by simple modification of the reaction conditions. FIG. 4C shows that dihydrosilanes can undergo double C(sp)-H silylation with NaOH as the catalyst to furnish diethynylsilanes. These products can be readily elaborated to polysubstituted siloles. It should be appreciated that this, and any of the specific examples provided here should be considered exemplars of broader embodiments of the present invention (e.g., in this case, of forming siloles and polysiloles). FIG. 4D shows that 2-silylpyridine directing groups can be installed onto simple alkynes in good yield. These fragments can be advanced to densely substituted olefins. FIG. 4E shows examples of late-stage derivatization of pharmaceutical substances pargyline and mestranol furnishing sila-therapeutics. In the case of the latter, both O—Si and C—Si dehydrogenative coupling occurs. Reactions were conducted on 0.5 mmol scale with 0.5 mL of solvent unless otherwise stated and at the prescribed temperature. Yields were of analytically pure isolated materials. [Si]=PhMe$_2$Si; DME=1,2-dimethoxyethane.

DETAILED DESCRIPTION OF ILLUSTRATIVE EMBODIMENTS

Figure 3:
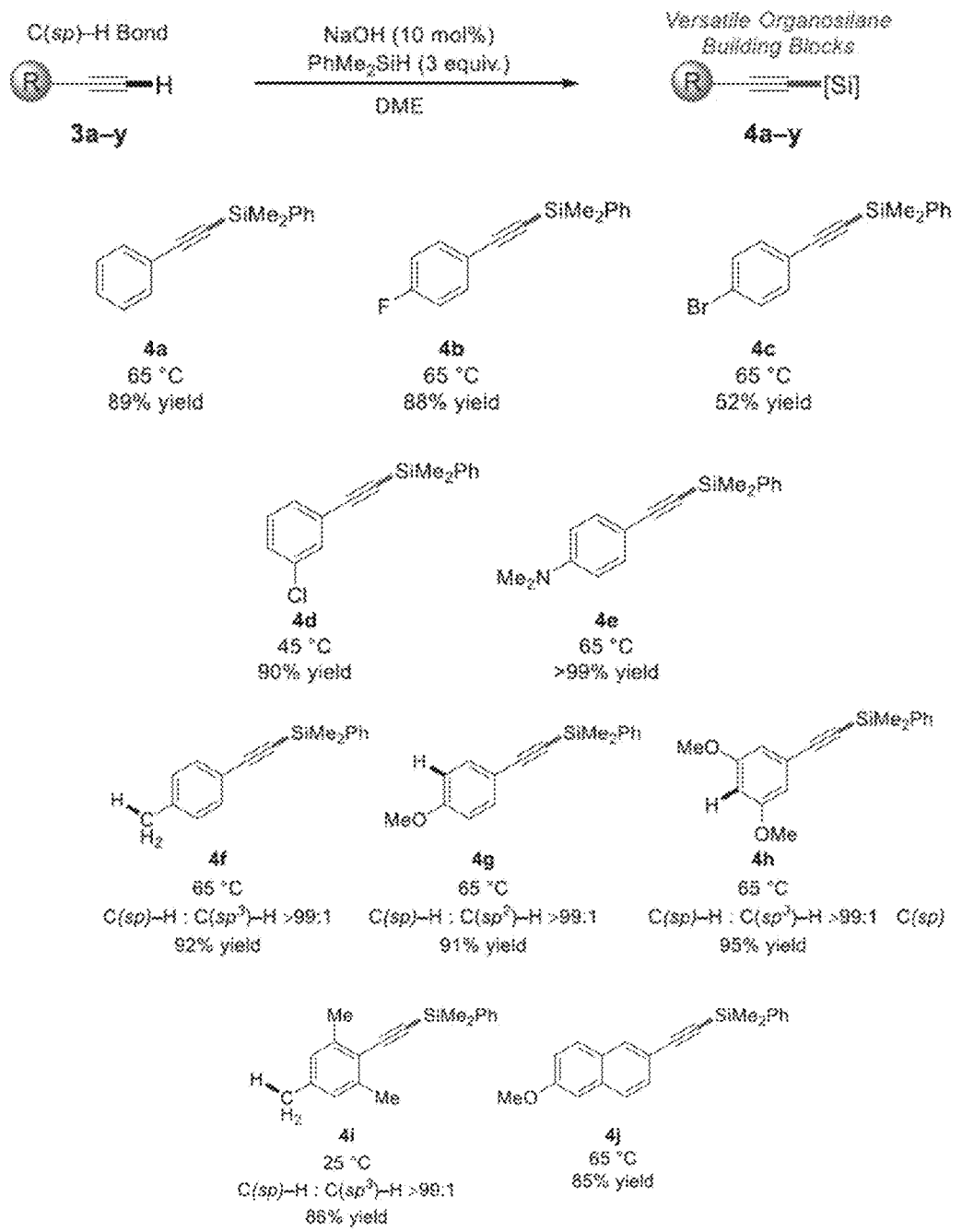
FIG. 3 illustrates the scope of the alkyne substrate. Propargyl alcohol (3x) underwent both O—Si and C—Si dehydrogenative coupling to give the bissilylated product 4x; by contrast, N—Si bond formation was not observed for N-methyl propargylamine (3w), giving monosilylated 4w. C—H bonds in bold represent sites that could be engaged by previously developed C—H functionalization methods, including KOt-Bu catalyzed silylation, potentially leading to product mixtures. Reactions were conducted on 0.5 mmol scale with 0.5 mL of solvent at the prescribed temperature. Yields are of analytically pure isolated materials. Selectivities determined by NMR and GC. DME=1,2-dimethoxyethane.
Figure 3:
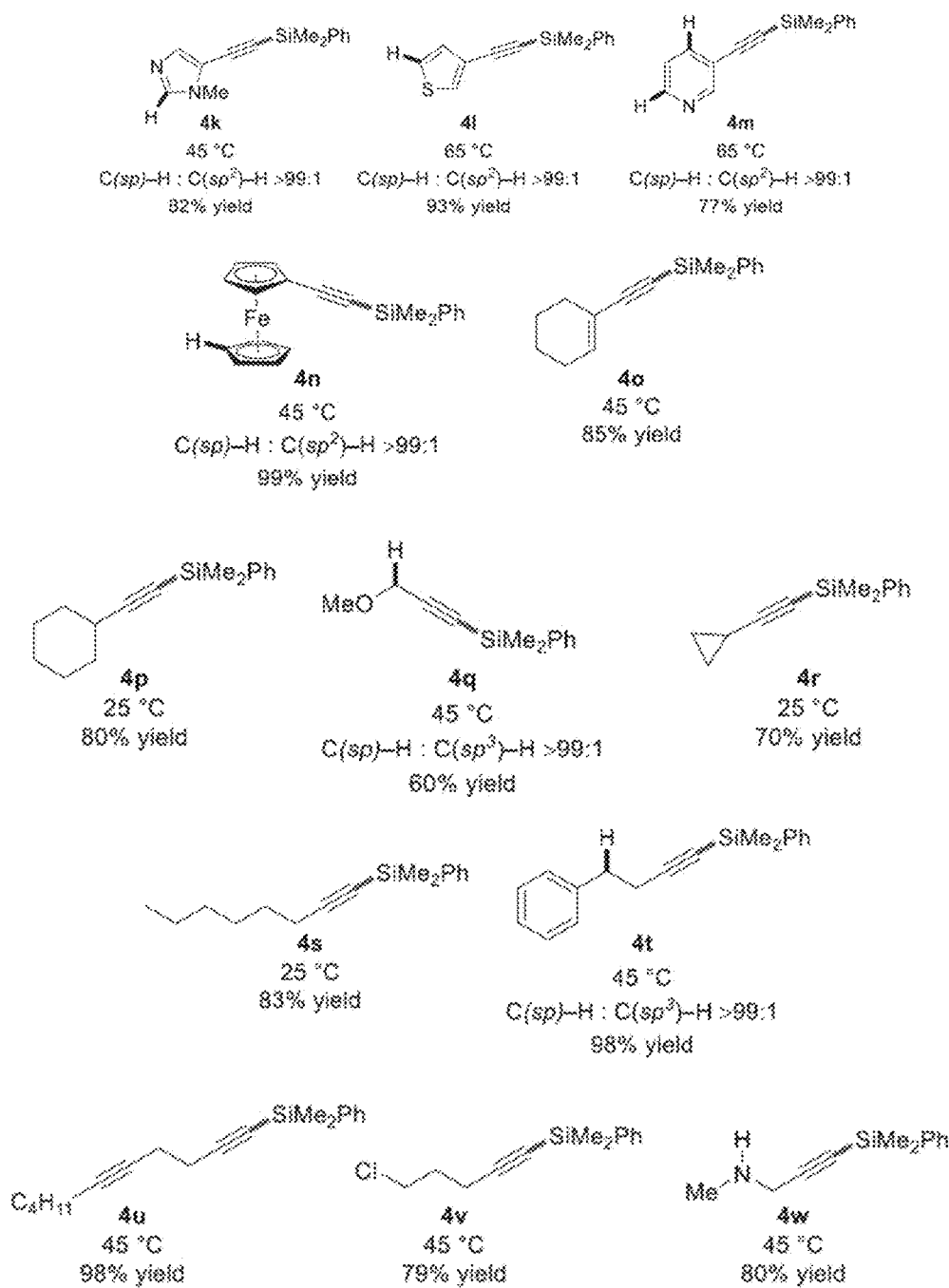
Figure 3:
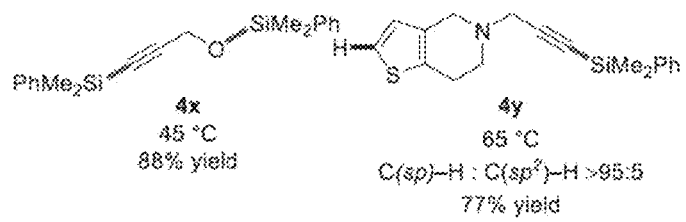

The present invention is founded on a set of reactions, each of which relies on simple mixtures of organosilanes and strong bases, including alkali metal hydroxide, alkoxides, and hydrides (preferably hydroxides) which together form in situ systems (the structure and nature of the active species is still unknown) able to silylate terminal alkyne groups, in the liquid phase, without the presence of transition metal catalysts, UV radiation or electrical (including plasma) discharges. These reactions are relevant as an important advance in developing practical methods for the preparation of products important for agrochemical, electronics, fine chemical, and pharmaceutical applications. Importantly this reaction is of great interest since it produces only environmentally benign silicates and dihydrogen as the byproduct and can avoid toxic metal waste streams as would be observed with nearly all other approaches proposed in the literature towards this end. The remarkable facility exhibited by these systems provides a useful tool in the kit of chemists in these fields. This utility can be leveraged when combined with other follow-on reactions.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

The present invention includes embodiments related chemical systems and methods for silylating terminal alkynes. Specific embodiments provide methods, each method comprising contacting at least one organic substrate comprising a terminal alkynyl C—H bond, with a mixture of at least one organosilane and an alkali metal hydroxide, alkoxides, and hydrides (preferably hydroxides), under conditions sufficient to form a silylated terminal alkynyl moiety. The reaction operate well in the complete absence of (or substantially complete absence) of transition-metal compounds. Likewise, these methods are also operable in the absence or substantially complete absence of other electromagnetic or thermal triggers needed for initiation or propagation. That is, these embodiments do not need UV irradiation or electric or plasma discharge conditions to operate.

As used herein to describe the systems and methods, the terms "organosilane" or "hydrosilane" may be used interchangeably and refer to a compound or reagent having at least one silicon-hydrogen (Si—H) bond and one carbon-containing moiety. The organosilane may further contain a silicon-carbon, a silicon-oxygen (i.e., encompassing the term "organosiloxane"), a silicon-nitrogen bond, or a combination thereof, and may be monomeric, or contained within an oligomeric or polymeric framework, including being tethered to a heterogeneous or homogeneous support structure. In certain embodiments, these organosilane may comprise at least one compound of Formula (I), Formula (II), or Formula (III):

$$(R)_{4-m}Si(H)_m \quad (I)$$

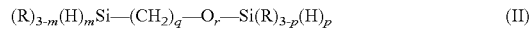

$$(R)_{3-m}(H)_mSi—(CH_2)_q—O_r—Si(R)_{3-p}(H)_p \quad (II)$$

$$R—[—SiH(R)—O—]_n—R \quad (III)$$

where: m and p are are independently 1, 2, or 3; q is 0, 1, 2, 3, 4, 5, or 6; r is 0 or 1; n is 10 to 100; and each R is independently halo (e.g., F, Br, Cl, I) (provided at least one R is contains carbon), optionally substituted $C_{1-12}$ alkyl or heteroalkyl, optionally substituted $C_{1-12}$ alkenyl or heteroalkenyl, optionally substituted $C_{1-12}$ alkynyl or heteroalkynyl, optionally substituted $C_{5-20}$ aryl or $C_{3-20}$ heteroaryl, optionally substituted $C_{6-30}$ alkaryl or heteroalkaryl, optionally substituted $C_{5-30}$ aralkyl or heteroaralkyl, optionally substituted —O—$C_{1-12}$ alkyl or heteroalkyl, optionally substituted —O—$C_{5-20}$ aryl or —O—$C_{3-20}$ heteroaryl, optionally substituted —O—$C_{5-30}$ alkaryl or heteroalkaryl, or optionally substituted —O—$C_{5-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. Exemplary, non-limiting organosilanes may independently include (R)$_3$SiH or (R)$_2$SiH$_2$, or (R)SiH$_3$. In some embodiments for Formula (II), q is 0. In some embodiments for Formula (II), r is 0. In some embodiment R is independently alkoxy, alkyl, alkenyl, aryl, aryloxy, heteroaryl, aralkyl, or heteroaralkyl. In certain embodiments, (R)$_3$SiH include the use of alkyl, aryl, heteraryl, alkoxy, or mixed alkyl-aryl silanes or alkyl-heteroaryl silanes, for example, EtMe$_2$SiH, (n-Bu)$_3$SiH, Et$_2$SiH$_2$, PhMe$_2$SiH, BnMe$_2$SiH, (EtO)$_3$SiH, (i-Pr)$_3$SiH, Me$_2$(pyridinyl)SiH, or (i-Pr)$_2$(pyridinyl)SiH, or Me$_3$Si—SiMe$_2$H. Embodiments involving R$_2$(pyridinyl)SiH silanes (i.e., the methods and systems involving them) are particularly unique as the inventors are unaware of these having ever been incorporated by a catalytic system of any type. Polymeric materials, such as polymethylhydrosiloxane (PMHS), are also effective.

Figure 4A:
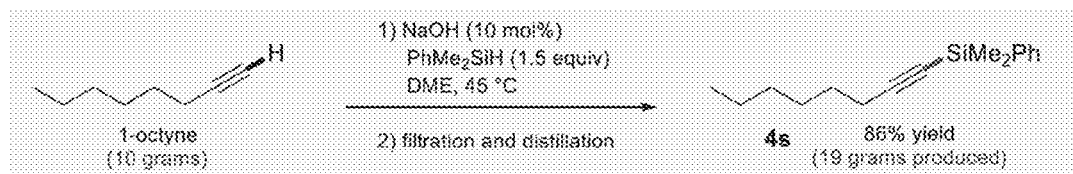
FIGS. 4A-4E illustrate some of the synthetic applications of the inventive methods.
Figure 4B:
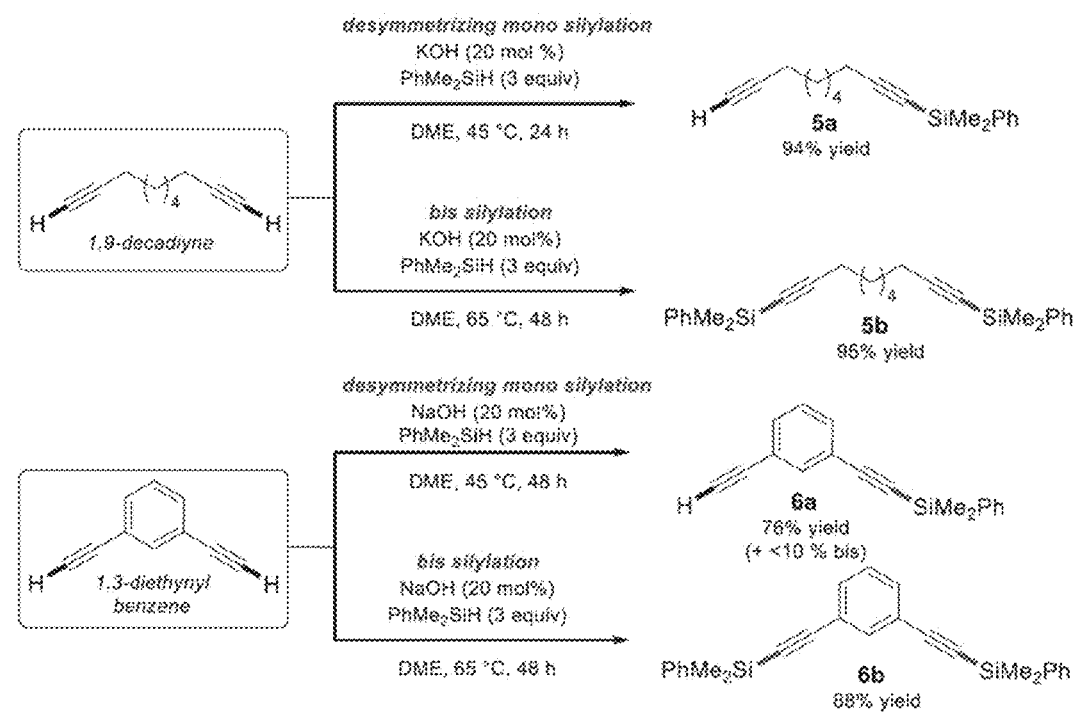
Figure 4C:
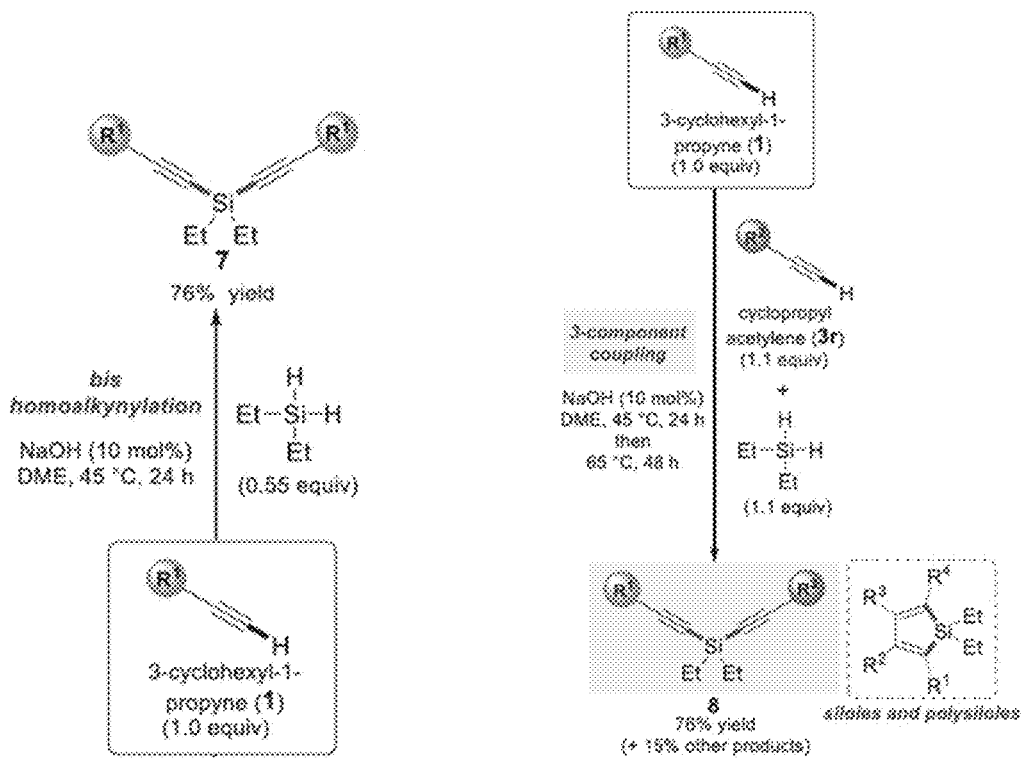

The use of organosilanes of general structure (R)$_2$SiH$_2$ and (R)SiH$_3$ also work well, and provide for opportunities for coupling or bridging reactions, as described herein. In the presence of a single substrate, bis-alkynyl silanes have been be isolated in good yield (see, e.g., Example 3.4; FIG. 4C). It is possible that at sufficiently mild conditions, the corresponding mono-alkynyl silane may be accessible, but that has yet to be observed. Interestingly, the R$_2$SiH$_2$ (and (R)SiH$_3$) organosilanes may also be reacted with different substrates to yield symmetric and asymetric bis- or tri-alkynyl silanes (again, see, e.g., Example 3.4). Note that Example 3.4 describes a reaction of equimolar amounts of two different substrates, resulting in a product mix that was predominantly (76%) cross-coupled. The reason for this substantial enrichment of the cross-coupled product, relative to what might have been expected from a purely statistical combination of the two substrates, is unknown, but suggests that this inventive methodology may provide a useful tool for the preferential formation of such di- or tri alkynyl cross-coupled silane products.

Additionally, the use of aceylene or poly-yne substrates, in the presence of R$_2$SiH$_2$ or silanes of Formula (II) may be useful for preparing polymeric or cyclic ethynlsilanes, non-limiting examples of which include the structure units:

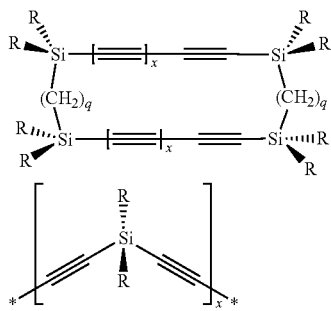

Some of these structures have been described by Gleiter, R. and D. B. Werz, *Chem. Rev.* 2010, 110, 4447-4488, which is incorporated by reference herein in its entirety for all purposes.

Previously, some of the inventors reported the use of potassium alkoxide and hydroxide catalysts to effect the silylation of aromatic and heteroaromatic substrates, and noted that potassium-based bases were unique in their ability in this regard. Here, the inventors have identified that, while potassium (and sodium) alkoxides (and in some cases KH) can be used with some substrates, the scope of the reaction is relatively limited (see, e.g., FIG. 6). In silylating terminal alkyne C—H groups, the use of alkali metal hydroxides, especially sodium hydroxide (NaOH) and potassium hydroxide (KOH) offers the possibility to silylate a much wider and more varied array of substrates. Interestingly, and for reasons not entirely understood, certain organosilane-substrate combinations practically operate to good yield with either KOH or NaOH (e.g., EtMe$_2$SiH, PhMe$_2$SiH, (n-Bu)$_3$SiH, Et$_2$SiH$_2$, (i-Pr)$_2$(pyridinyl)SiH, or Me$_2$(pyridinyl)SiH), while others appear to respond better to the use of NaOH(PhMe$_2$SiH, BnMe$_2$SiH, (EtO)$_3$SiH, Me$_2$(pyridinyl)SiH, or Me$_3$Si—SiMe$_2$H), and still others respond better to the use of KOH ((i-Pr)$_3$SiH, or (i-Pr)$_2$(pyridinyl)SiH), at least under the mild reaction conditions described herein (see, e.g., FIG. 5). This cation effect (NaOH vs. KOH) also appears to depend on the natures of the substrate (compare reactivity of Me$_2$PhSiH with various substrates in FIG. 5). The mechanistic reason for this unique and previously unrecognized cation effect is not yet understood. The ability of NaOH and sodium alkoxides (Table 1) to affect these silylations is especially interesting, given their unworkability in other aryl and heteroaryl systems. Note that the reference to independent use of sodium hydroxide, sodium alkoxide, potassium hydroxide, and potassium alkoxides, while preferred do not preclude these materials being used in any combination with one another, and these mixtures are seen as additional embodiments.

The Examples provide exemplary reaction conditions useful for effecting the desired transformations. In other embodiments, substrates, alkali metal hydroxides, alkoxides, and hydrides (preferably hydroxides), and organosilanes may be heated to temperatures ranging from 0° C. to 150° C., or higher, for times ranging from 24 hours to several days, though practically, the reactions proceed to good yield and selectivity when conducted at a temperate in a range of ambient room temperature (e.g., 25° C.) to about 85° C. Interesting, it is shown within this application that by staging the reaction temperatures (for example, from even 45° C. to 65° C.), it is possible to select and provide products that are either monosilylated or disilylated on substrates having two apparently equivalent terminal alkynyl C—H bonds (see, e.g., Example 3.3, FIG. 4B).

These methods typically employ hydrocarbon or ether-based solvents, or can be operated without solvent. Ether solvents, such as tetrahydrofurans (including 2-methyltetrahydrofuran), diethyl and dimethyl ether, 1,2-dimethoxyethane, dioxane, and alkyl terminated glycols have been shown to work well.

The methods are fairly flexible with respect to substrates, particularly when considering NaOH, KOH, or mixtures thereof. The inventive methods provide for the silylation of a wide range of substrates having one, two, or more terminal alkynyl C—H bonds with remarkable efficiency. In some embodiments, the organic substrate comprising the terminal alkynyl C—H bond is described in term of a formula:

where R$^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene. R$^1$ may include individual molecular moieties or be oligomeric or polymeric.

Independent embodiments include those where R$^1$ is or comprises:

(a) an optionally substituted linear alkyl, an optionally substituted branched alkyl, or an optionally substituted cycloalkyl;
(b) an optionally substituted linear alkenyl, an optionally substituted branched alkenyl, or an optionally substituted cycloalkenyl;
(c) an optionally substituted linear heteroalkyl, an optionally substituted branched heteroalkyl, or an optionally substituted heterocycloalkyl;
(d) an optionally substituted aryl, an optionally substituted aralkyl, optionally substituted heteroaryl, or an optionally substituted heteroaralkyl; or
(e) a combination of any two or more types of substituents listed in (a) through (d).

In more specific embodiments, $R^1$ is or comprises:
(a) an optionally substituted benzene, biphenyl, naphthalene, or anthracene ring structure; or
(b) an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety; or
(c) the organic substrate comprising the terminal alkynyl C—H bond is polymeric.

Each of the substrates and organosilanes represent specific examples and embodiments of the materials within the scope of the present invention.

Once formed, the silylated terminal alkynyl moiety can be subject to a variety of known chemical reactions, and the present invention contemplates that methods employing these known methods, when coupled with the inventive methods described here, are within the scope of the present invention. For the sake of clarity, the term "original silylated product" is introduced here to represent the silylated product of the inventive methods, this original silylated product containing the silylated terminal alkynyl moiety previously described. Except as otherwise specified, the reactions which follow represent excellent ways in which to incorporate silyl groups in the final products.

For example, alkynes are useful synthons in forming silylated aromatic, heteroaromatic, cycloalkenyl, or heterocycloalkenyl moieties using Diels-Alder type [2+2] or [4+2] cycloaddition reaction. The pre-incorporation of silyl groups attached to the alkyne group of the present products provides an interesting alternative means to incorporate silyl groups on such aromatic, heteroaromatic, cycloalkenyl, or heterocycloalkenyl products. Accordingly, in some embodiments of the present invention, the silylated terminal alkynyl moiety formed by the present methods may be further reacted with another unsaturated moiety (for example an optionally substituted alkene, alkyne, azide, nitrile, isocynate, isothiocyanate, carbonyl, amide, urea, etc.) to form a silylated aromatic, heteroaromatic, cycloalkenyl, or heterocycloalkenyl structure. This "another unsaturated moiety" may be introduced as a separate molecular entity (i.e., an intermolecular reaction) or may be present in the original silylated product (i.e., an intramolecular reaction)—see e.g., FIG. 4C for but one example of this. In either case, the original silylated product may or may not need to be isolated before effecting the cyclization, and if the latter, the reaction may be conducted in a single pot synthesis.

In other embodiments, the original silylated product may also be reacted with a second, unsaturated organic moiety (cyclic or acyclic, comprising optionally substituted alkene, alkyne, azide, nitrile, isocynate, isothiocyanate, carbonyl, amide, urea, etc.) in a cross-metathesis reaction to form a silylated diolefin or polyolefin product. Such cross-metathesis metathesis reactions are well-known, and the person of ordinary skill would know how to effect these transformations. For example, the use of Grubbs-type ruthenium carbene metathesis catalysts may be used for this purpose, though the contemplated transformations are not limited to these types of catalysts. These may be represented schematically as:

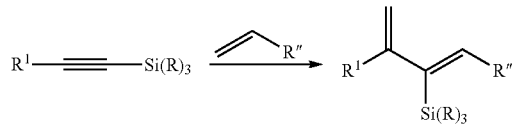

Again, the reactions may be intra- or intermolecular, single- or multi-pot syntheses, and provide another method for incorporating silyl groups under facile and mild conditions. Such downstream transformations are described, for example, in Kim, et al., *J. Amer. Chem. Soc.*, 126 (33), 2004, 10242-10243, which is incorporated by reference herein for its teaching in at least this regard. These products may then be subject to the Diels-Alder type [2+2] or [4+2] cycloaddition reactions described above.

Alternatively, or additionally, the original silylated product may be copolymerized with an optionally substituted enyne, diene, diyne, or cyclic olefin, using any suitable catalyst(s) to form silylated polymers. In certain embodiments, these reactions may comprise metathesis polymerization, for example ROMP. Such metathesis polymerization reactions are well-known, and the person of ordinary skill would know how to affect them, for example, again using Grubbs-type ruthenium carbene metathesis catalysts, though the contemplated transformations are not limited to these types of catalysts. Again, the reactions may be intra- or intermolecular, single- or multi-pot syntheses, and provide another method for incorporating silyl groups into polymers under facile and mild conditions. For example, such methods may provide silylated conducting polyacetylene polymers that would be useful in electronic applications.

In other embodiments, the original silylated product may be further reacted to hydrogenate the silylated terminal alkynyl moiety. This silylated terminal alkynyl moiety may also be reacted with water, alcohols, hydrogen cyanide, hydrogen chloride, dihalogen, or carboxylic acids under conditions known to give corresponding vinyl compounds or carbonyl-type compounds. Again, the skilled artisan would be able to affect these transformations without undue effort.

In other embodiments, the original silylated product may be reacted with n organic azide in a [3+2]azide-alkyne cycloaddition reaction, for example forming silylated triazoles. Such reactions are also well-known, as so-called Click chemistry, which include 1,3-dipolar cycloadditions. Such reactions may be inter- or intramolecular reaction and are typically catalyzed by copper, copper-iron, or ruthenium-containing catalysts. Again, it would be well within the skills of a person of ordinary skill to affect such transformations without undue burden.

Other embodiments provide that alkynyl aryl silanes react with, for example, triflic acid, to form silanols. See, for example, Franz, A. K., et al., *J. Med. Chem.*, 2013, 56, 388-405, which is incorporated by reference herein in its entirety for all purposes. Accordingly, certain embodiments of this invention provide for the further reaction of the original silylated product with triflic acid to form the corresponding silanol. As the present invention also allows for the incorporation of alkoxy silanes (e.g., $(RO)_3SiH$), similar silanol products can be prepared simply by hydrolyzing the original silylated product, where that original silylated product contains comprises an alkoxysilyl group.

The mildness of the conditions in these inventive methods, and the absence of any need for transition metal catalysts, makes them especially suitable for pharmaceutical or medicinal applications, silyl derivatives have been shown to be particularly important. In addition to the use of the inventive silyl derivatives for mechanistic determinations of modes of action, of enhancing tissue penetration, altering hydrogen-bonding effects, and lack of known toxicity effects, organosilicon compounds are finding use as biological imaging agents. The inventive silylated terminal alkynes can be expected to be effective in their own right for these purposes, as the methods allow for the incorporation of a wide variety of silyl moieties at virtually any stage in a drug's synthesis. Additionally, siloxylated terminal olefins (e.g., where the silylated terminal alkynyl moiety comprises an $—Si(OR)_3$ group) may further be reacted with, for example $KHF_2$, to form tetrafluorosilicate groups—i.e, as $R^1—C≡C—SiF_4^-$ compounds (or radiolabeled $^{18}F$ versions thereof). Such transformations and advantages are described, for example, in Franz, A. K., et al., *J. Med. Chem.*, 2013, 56, 388-405.

The inventive terminal alkynyl silanes may also be activated by fluoride or alkoxides, with the associated removal of the silyl group to form alkynyl nucleophiles which can then react with electrophiles. Accordingly, other embodiments also provide for the reaction of the silylated terminal alkynyl moiety with a fluoride containing salt (e.g., alkali metal or tetra-aryl, tetra-alkyl, or mixed alkyl/aryl ammonium salts) with or without the presence of an acid stronger then HF to generate an activated, desilylated alkynyl nucleophile, to be added to other substrates, for example, alkyl halides (or any alkyl group with a suitable leaving group, including without limitation tosylates, triflates, or any alcohol, amine, or carboxylic acid protecting group), acyl halides (including acyl chlorides), substituted alkene (e.g., Michael addition acceptors), enones (or generally α,β-unsaturated carbonyl compounds), epoxides, esters, α-ketoesters (including trifluoro- or other substituted pyruvate), etc. In the presence of chiral palladium catalysts, such as (but not limited to) (S)-BINAP-$Pd^{2+}$ catalysts, the reaction may be done to yield optically active addition products. Such chemistry is described, for example, in Aikawa, K., et al., *Org. Lett.*, 12, 5716-5719 (2010), which is incorporated by reference for all purposes.

In other embodiments, the original silylated product may be further reacted simply to remove the silyl group originally added to the terminal alkynyl C—H bond and replace it with a hydrogen, deuterium, or tritium atom. This could be accoomplished, for example, simply by quenching the desilylated alkynyl nucleophile with a protic (of isotopic) source. Such a strategy would be useful if the silyl group was originally added to protect the otherwise acidic terminal alkynyl C—H group from reactions conducted on the substrate away from this C—H group, or act as a directing group (e.g., see the carbomagnesation reactions described below).

In still other embodiments, the silylated terminal alkynyl moiety may be reacted with an N-halosuccinimide in the presence of a cationic gold catalyst to produce a terminal alkynyl halide, where halo is preferably bromo or iodo. Again, such reactions are known and described, for example, in Starkov, et al., *Adv. Synth. Catal.*, 2012, 354, pp. 3217-3224, which is incorporated by reference herein in its entirety for all purposes.

In other embodiments, the original silylated product may be further reacted with an aromatic halide compound under conditions sufficient to form an alkynyl-arene linkage, for example using Pd/Cu catalysts, such as $Pd(PPh_3)_2Cl_2$, CuI catalysts and optionally substituted iodo or bromo aromatic compounds. E.g.,

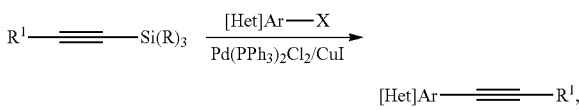

where R and $R^1$ are as described above, and [Het]Ar—X refers to an optionally substituted aryl or heteroaryl bromide or iodide.

In other specific embodiments, wherein the at least one organosilane comprises an optionally substituted $C_{1-12}$ alkenyl or heteroalkenyl, such that the silylated terminal alkynyl moiety comprises a silicon bonded optionally substituted $C_{1-12}$ alkenyl or heteroalkenyl, the silylated terminal alkynyl moiety may further be reacted with an alcohol and a catalyst under conditions to result in the intramolecular allylation of the silylated terminal alkynyl moiety:

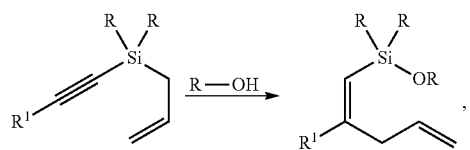

where R and $R^1$ are as described above. Such reactions have been described, for example, in Park and Lee, *J. Amer. Chem. Soc.* 2006, 128, 10664-10665, which is incorporated by reference herein in its entirety for all purposes.

In the specific case wherein the at least one organosilane comprises a 2-pyridinyl group (of which $(Me)_2$(pyridinyl)SiH or $(i-Pr)_2$(pyridinyl)SiH are but two non-limiting examples), further embodiments provide methods in which the silylated terminal alkynyl moiety is reacted with a copper carbomagnesation catalyst and an optionally substituted aryl or optionally substituted heteroaryl magnesium complex under conditions suitable and sufficient sufficient to carbomagnesate the silylated terminal alkynyl moiety. Such reactions are well-documented, for example in Itami, et al., *Synlett* 2006, No. 2, 157-180, which is incorporated by reference herein in its entirety for all purposes. In such cases, for example, the reaction of an original silylated product as shown below, with an optionally substituted aromatic magnesium complex, such as described in terms of $[Het]Ar^1—MgI$, results in a corresponding carbomagnesated product:

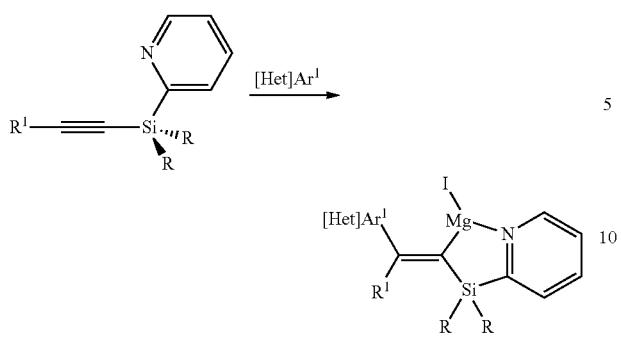

where R and R¹ are as described above, and [Het]Ar¹ is an optionally substituted aryl or heteroaryl moiety, again as described above. The conditions useful for carrying out this and the following transformations are available in the Itami reference cited above. Thecombined reactions are a powerful way of forming stereospecific products.

The carbomagnesated silylated terminal alkynyl moiety may then be reacted with an optionally substituted aryl iodide or optionally substituted heteroaryl iodide (designated here as [Het]Ar²) in the presence of a palladium catalyst to form a trisubstituted silylated olefin. For example,

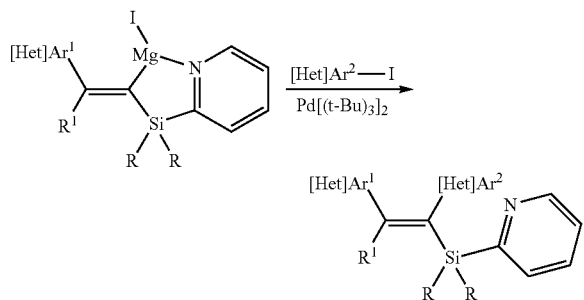

where [Het]Ar² is also an optionally substituted aryl or heteroaryl moiety, again as described above, which may be the same or different than [Het]Ar¹.

The trisubstituted silylated olefin may then reacted with BCl₃ and pinacol under conditions sufficient to borodesilylate the compound. In separate steps, the borodesilylated compound may be reacted with a second optionally substituted aryl iodide or optionally substituted heteroaryl iodide under conditions suitable to cross-couple the resulting C—B bond and the second optionally substituted aryl iodide or optionally substituted heteroaryl iodide. These reactions are shown schematically as:

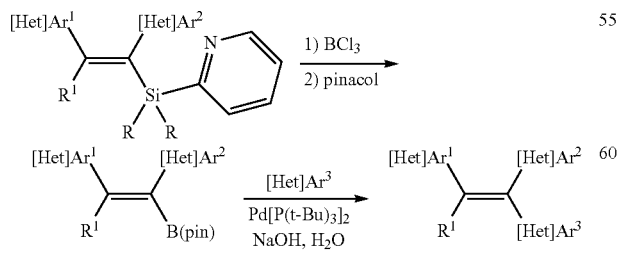

where [Het]Ar³ is also an optionally substituted aryl or heteroaryl moiety, again as described above, which may be the same or different than [Het]Ar¹ or [Het]Ar². The borodesilylation reactions have been previously described, for example, in Babudri, et al., *Tetrahedron* 1998, 54, 1085) as have the Suzuki-Miyaura-type boron-based crosscoupling reactions (e.g., see (a) Miyaura, N.; Suzuki, A. *Chem. Rev.* 1995, 95, 2457; and (b) Miyaura, N. *Top. Curr. Chem.* 2002, 219, 11). Each of these references is incorporated by reference herein in their entireties for all purposes.

It should be appreciated that hydrogenating the original silylated product containing a a 2-pyridinyl silyl group can result in the corresponding 2-pyridinyl silyl olefin, and that the reference to Itami (i.e., Itami, et al., *Synlett* 2006, No. 2, 157-180) describes a rich chemistry of such compounds. To the extent allowable by local law, such transformations of products derived from the inventive methods described in the present disclosure are also considered within the scope of the present invention.

The inventive concepts have been thusfar described in terms of the methods of catalytically silylating terminal alkynyl C(sp)-H bonds. It should be appreciated that the products obtained from such methods, to the extent that they are not practically available by other means known at the time of this filing, and the systems used in these methods, are all considered within the scope of the present disclosure.

Again, the present invention includes embodiments for any system necessary to affect any of the methods described herein. For example, certain embodiments provide systems for silylating an organic substrate comprising a terminal alkynyl C—H bond, each system comprising or consisting essentially of a mixture of (a) at least one organosilane and (b) an alkali metal hydroxide (and in some cases, sodium or potassium alkoxide or hydride, or a mixture thereof), and (c) at least one substrate. Such systems typically include the substrate(s) upon which the system is operable, the substrates comprising at least one terminal alkynyl C(sp)-H moiety. Typically, the system is substantially free of transition-metal compounds, or where present, the transition metal may be considered a spectator to the reaction. In some embodiments, the system further comprises the presence of a silylated terminal alkyne derived from the reaction between the substrate and the at least one organosilane.

In such systems, the at last one organosilane comprises an organosilane of Formula (I), Formula (II), or Formula (III):

$$(R)_{4-m}Si(H)_m \qquad (I)$$

$$(R)_{3-m}(H)_m Si-(CH_2)_q-O_r-Si(R)_{3-p}(H)_p \qquad (II)$$

$$R-[-SiH(R)-O-]_n-R \qquad (III)$$

where: m, n, p, q, r and R are described elsewhere. Similarly, in various independent embodiments of the systems:
(a) the organosilane is $(R)_3SiH$, $(R)_2SiH_2$, or $(R)SiH_3$;
(b) R independently comprises alkoxy, alkyl, alkenyl, aryl, aryloxy, heteroaryl, aralkyl, or heteroaralkyl;
(c) the alkali metal hydroxide is sodium hydroxide (NaOH), potassium hydroxide (KOH), or a combination thereof;
(d) the alkali metal alkoxide is a sodium hydroxide, potassium alkoxide (KOH), or a combination thereof;
(e) the organic substrate comprising the terminal alkynyl C—H bond has a formula:

$$R^1-C\equiv C-H,$$

where R¹ is defined according to any of the method embodiments described above.

TERMS

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods to provide silylated products at meaningful yields (or the ability of the systems used in such methods to provide the product compositions at meaningful yields or the compositions derived therefrom) to silylate terminal alkynyl C(sp)-H moieties using only those ingredients listed. In those embodiments that provide a system or method comprises the use of a mixture consisting essentially of the substrate, organosilane (alternatively referred to as hydrosilane), and strong base (sodium or potassium hydroxide, alkoxide, or hydride), it refers to the fact that this system operates to silylate the substrate at rates corresponding to those described herein under comparable conditions as described herein without additional (e.g., transition metal) catalysts or plasma or UV radiation sources. While some level of transition metals may be present (for example, as a substrate), they are not needed for the operability of the methods, and may be considered spectators for purposes of this reaction. Indeed, extensive experiments and analyses conducted rule out catalysis by adventitious transition metal residues (see Example 2.1.2, Table 2). Similarly, while other previous silylation reactions have employed plasma or UV irradiation to operate, the present invention does not require these energy sources. The additional presence of these energy sources should not be seen as replacing the basis underlying operability of the present methods. The term "meaningful product yields" is intended to reflect product yields of greater than 50%, but when specified, this term may also refer to yields of 10%, 20%, 30%, 40%, 50%, 60%, 70%, 80%, or 90% or more, relative to the amount of original substrate.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes $C_1$, $C_2$, $C_3$, $C_{1-2}$, $C_{2-3}$, $C_{1,3}$, as separate embodiments, as well as $C_{1-3}$.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or prepolymeric (e.g., monomeric, dimeric), oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)— alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene"and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, pre-polymers (i.e., monomeric compounds capable of polymerizing), oligomers, or polymers having at least one of the indicated aromatic structure. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano (—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl) substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2OH$), sulfonate($SO_2O$—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—$PO_2$), and phosphine (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl](DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —CF$_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "silylating" refers to the forming of carbon-silicon bonds, generally in a position previously occupied by a carbon-hydrogen bond, generally a non-activated C—H bond. Silylating may be seen as coupling of a C—H and Si—H bond to form a C—Si bond. The ability to replace directly a C—H bond with a C—Si bond, under the conditions described herein, is believed to be unprecedented.

As used herein, the term "substantially free of a transition-metal compound" is intended to reflect that the system is effective for its intended purpose of silylating terminal alkyne C—H bonds under the relatively mild conditions described herein, even in the absence of any exogenous (i.e., deliberately added or otherwise) transition-metal catalyst(s). While certain embodiments provide that transition metals, including those capable of catalyzing silylation reactions, may be present within the systems or methods described herein at levels normally associated with such catalytic activity (for example, in the case where the substrates comprise metallocenes), the presence of such metals (either as catalysts or spectator compounds) is not required and in many cases is not desirable. As such, in preferred embodiments, the system and methods are "substantially free of transition-metal compounds." Unless otherwise stated, then, the term "substantially free of a transition-metal compound" is defined to reflect that the total level of transition metal within the silylating system, independently or in the presence of organic substrate, is less than about 5 ppm, as measured by ICP-MS as described in Example 2.1.2, Table 2 below. When expressly stated as such, additional embodiments also provide that the concentration of transition metals is less than about 10 wt %, 5 wt %, 1 wt %, 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include d-block elements, for example Ag, Au, Co, Cr, Rh, Ir, Fe, Ru, Os, Ni, Pd, Pt, Cu, Zn, or combinations thereof. In further specific independent embodiments, the concentration of Ni, as measured by ICP-MS, is less than 25 ppm, less than 10 ppm, less than 5 ppm, or less than 1 ppm.

While it may not be necessary to limit the system's exposure to water and oxygen, in some embodiments, the chemical systems and the methods are done in an environment substantially free of water, oxygen, or both water and oxygen. In other embodiments, air and/or water are present. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5%, 1%, 0.5%, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr. In the General Procedure described herein, deliberate efforts were made to exclude both water and oxygen, unless otherwise specified.

The following listing of Embodiments is intended to complement, rather than displace or supersede, the previous descriptions.

Embodiment 1

A method comprising contacting at least one organic substrate comprising a terminal alkynyl C—H bond, with a mixture of at least one organosilane and an alkali metal hydroxide (or alkoxide or hydride), under conditions sufficient to form a silylated terminal alkynyl moiety in the substantially absence of transition-metal compounds. Relatedly, this method also comprises operating in the substantial absence of transition metal compounds, or other electromagnetic or thermal initiation or propagation.

Embodiment 2

The method of Embodiment 1, wherein the transition-metal compounds are present at less than 1 ppm, relative to the weight of the total system.

Embodiment 3

The method of Embodiment 1 or 2, wherein at least one organosilane comprises an organosilane of Formula (I), Formula (II), or Formula (III):

$$(R)_{4-m}Si(H)_m \qquad (I)$$

$$(R)_{3-m}(H)_mSi\text{---}(CH_2)_q\text{---}O_r\text{---}Si(R)_{3-p}(H)_p \qquad (II)$$

$$R\text{---}[\text{---}SiH(R)\text{---}O\text{---}]_n\text{---}R \qquad (III)$$

where: m and p are are independently 1, 2, or 3; q is 0, 1, 2, 3, 4, 5, or 6; r is 0 or 1; n is 10 to 100; and each R is independently halo (e.g., F, Br, Cl, I) (provided at least one R is contains carbon), optionally substituted $C_{1\text{-}12}$ alkyl or heteroalkyl, optionally substituted $C_{1\text{-}12}$ alkenyl or heteroalkenyl, optionally substituted $C_{1-12}$ alkynyl or heteroalkynyl, optionally substituted $C_{5-20}$ aryl or $C_{3-20}$ heteroaryl, optionally substituted $C_{6-30}$ alkaryl or heteroalkaryl, optionally substituted $C_{5-30}$ aralkyl or heteroaralkyl, optionally substituted —O—$C_{1-12}$ alkyl or heteroalkyl, optionally substituted —O—$C_{5-20}$ aryl or —O—$C_{3-20}$ heteroaryl, optionally substituted —O—$C_{5-30}$ alkaryl or heteroalkaryl, or optionally substituted —O—$C_{5-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In some embodiments for Formula (II), q is 0. In some embodiments for Formula (II), r is 0. Any of the silanes described in this disclosure are also considered separate embodiments when used in these methods or systems.

Embodiment 4

The method of claim 3, wherein the organosilane is $(R)_3SiH$, $(R)_2SiH_2$, or $(R)SiH_3$. In some of these embodiments, R is independently alkoxy, alkyl, alkenyl, aryl, aryloxy, heteroaryl, aralkyl, or heteroaralkyl.

Embodiment 5

The method of any one of Embodiments 1 to 4, wherein the alkali metal hydroxide is sodium hydroxide (NaOH) (or the alkali metal alkoxide is sodium alkoxide).

Embodiment 6

The method of Embodiment 5, wherein the organosilane is $EtMe_2SiH$, $PhMe_2SiH$, $BnMe_2SiH$, $(n-Bu)_3SiH$, $Et_2SiH_2$, $(EtO)_3SiH$, $Me_2(pyridinyl)SiH$, or $Me_3Si$—$SiMe_2H$.

Embodiment 7

The method of any one of Embodiments 1 to 4, wherein the alkali metal hydroxide is potassium hydroxide (KOH) (or the alkali metal alkoxide is potassium alkoxide).

Embodiment 8

The method of Embodiment 7, wherein the organosilane is $EtMe_2SiH$, $PhMe_2SiH$, $(n-Bu)_3SiH$, $Et_2SiH_2$, $(i-Pr)_3SiH$, or $(i-Pr)_2(pyridinyl)SiH$.

Embodiment 9

The method of any one of Embodiments 1 to 8, wherein the organic substrate comprising the terminal alkynyl C—H bond has a formula:

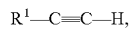

$R^1$—C≡C—H, where $R^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene.

Embodiment 10

The method of Embodiment 9, wherein $R^1$ is or comprises an optionally substituted linear alkyl, an optionally substituted branched alkyl, or an optionally substituted cycloalkyl.

Embodiment 11

The method of Embodiment 9, wherein $R^1$ is or comprises an optionally substituted linear alkenyl, an optionally substituted branched alkenyl, or an optionally substituted cycloalkenyl Embodiment 12

The method of Embodiment 9, wherein $R^1$ is or comprises an optionally substituted linear heteroalkyl, an optionally substituted branched heteroalkyl, or an optionally substituted heterocycloalkyl.

Embodiment 13

The method of Embodiment 9, wherein $R^1$ is or comprises an optionally substituted aryl, an optionally substituted aralkyl, optionally substituted heteroaryl, or an optionally substituted heteroaralkyl.

Embodiment 14

The method of Embodiment 13, wherein $R^1$ is or comprises an optionally substituted benzene, biphenyl, naphthalene, or anthracene ring structure.

Embodiment 15

The method of Embodiment 13, wherein $R^1$ is or comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 16

The method of any one of Embodiments 1 to 15, wherein the organic substrate comprising the terminal alkynyl C—H bond is polymeric.

Embodiment 17

The method of any one of Embodiments 3 to 16, where m=2, or 3, further comprising contacting a second or third organic substrate comprising a terminal alkynyl C—H bond with the first formed silylated terminal alkynyl moiety to form a di- or tri-akynyl cross-coupled silane product. This second (or third) organic substrate can be same or different than first.

Embodiment 18

The method of any one of Embodiments 1 to 17, further comprising reacting the silylated terminal alkynyl moiety with another unsaturated moiety in a [2+2] or [4+2] cycloaddition reaction to form an aromatic, heteroaromatic, cycloalkenyl, or heterocycloalkenyl moiety. The unsaturated moiety can include alkene, alkyne, azide, nitrile, isocynate, isothiocyanate, carbonyl, amide, urea, etc., and the reaction may be inter- or intramolecular.

Embodiment 19

The method of any one of Embodiments 1 to 17, further comprising reacting the silylated terminal alkynyl moiety with a second, unsaturated organic moiety in a cross-metathesis reaction to form a diolefin or polyolefin product. The unsaturated moiety can include alkene, alkyne, azide, nitrile, isocynate, isothiocyanate, carbonyl, amide, urea, etc., and the reaction may be inter- or intramolecular reaction. In some of these embodiments, the metathesis is accomplished using a Grubbs-type metathesis reaction catalyst.

Embodiment 20

The method of any one of Embodiments 1 to 17, further comprising polymerizing the silylated terminal alkynyl moiety. The silylated terminal alkynyl moiety may also be copolymerized with other acetylenic or olefinic compounds, by any means, including metathesis and free radical mechanisms.

Embodiment 21

The method of any one of Embodiments 1 to 17, further comprising reacting the silylated terminal alkynyl moiety with an organic azide a [3+2]azide-alkyne cycloaddition reaction. This so-called Click chemistry, includes 1,3-dipolar cycloadditions, may be inter- or intramolecular reaction, and typically involve the use of copper, copper-iron, or ruthenium-containing catalysts.

Embodiment 22

The method of any one of Embodiments 1 to 17, further comprising hydrogenating the silylated terminal alkynyl moiety. Certain other embodiments include the reaction of the silylated terminal alkynyl moiety with water, alcohols, hydrogen cyanide, hydrogen chloride, dihalogen, or carboxylic acids to give corresponding vinyl or carbonyl compounds.

Embodiment 23

The method of any one of Embodiments 1 to 20, further comprising removing the silyl group originally added to the terminal alkynyl C—H bond, such the the added silyl group was used as a blocking or directing group for other transformations in the substrate.

Embodiment 24

The method of any one of Embodiments 1 to 20, further comprising reacting silylated terminal alkynyl moiety with an aromatic halide compound under conditions sufficient to form an alkynyl-arene linkage; e.g., using $Pd(PPh_3)_2Cl_2$/CuI catalysts with aromatic bromo or iodo compounds.

Embodiment 25

The method of any one of Embodiments 1 to 17, further comprising reacting the silylated terminal alkynyl moiety with an N-halosuccinimide in the presence of a cationic gold catalyst to produce a terminal alkynyl halide, where halo is preferably bromo or iodo.

Embodiment 26

The method of any one of Embodiments 1 to 20, wherein the at least one organosilane comprises an optionally substituted $C_{1-12}$ alkenyl or heteroalkenyl, such that the silylated terminal alkynyl moiety comprises a silicon bonded optionally substituted $C_{1-12}$ alkenyl or heteroalkenyl, the method further comprising reacting the silylated terminal alkynyl moiety with an alcohol and a catalyst under conditions to result in the intramolecular allylation of the silylated terminal alkynyl moiety.

Embodiment 27

The method of any one of Embodiments 1 to 20, wherein the at least one organosilane comprises a 2-pyridinyl group (as typified herein using $(Me)_2$(pyridinyl)SiH or $(i-Pr)_2$(pyridinyl)SiH), the method further comprising reacting the silylated terminal alkynyl moiety with a copper carbomagnesation catalyst and an optionally substituted aryl or optionally substituted heteroaryl magnesium complex under conditions sufficient to carbomagnesate the silylated terminal alkynyl moiety.

Embodiment 28

The method of Embodiment 27, further comprising reacting the carbomagnesated silylated terminal alkynyl moiety with an optionally substituted aryl iodide or optionally substituted heteroaryl iodide in the presence of a palladium catalyst to form a trisubstituted silylated olefin.

Embodiment 29

The method of Embodiment 28, further comprising reacting the trisubstituted silylated olefin with $BCl_3$ and pinacol under conditions sufficient to borodesilylate the compound, and optionally reacting the borodesilylated compound with a second optionally substituted aryl iodide or optionally substituted heteroaryl iodide under conditions suitable to cross-couple the resulting C—B bond and the second optionally substituted aryl iodide or optionally substituted heteroaryl iodide.

Embodiment 30

A system for silylating an organic substrate comprising a terminal alkynyl C—H bond, said system comprising or consisting essentially of a mixture of (a) at least one organosilane and (b) an alkali metal hydroxide (or in some cases, alkali metal alkoxide or hydride), and (c) at least one substrate. Such systems may be substantially free of transition-metal compounds. Such systems may also contain a silylated product derived from the at least one organosilane and the terminal alkyne.

Embodiment 31

The system of Embodiment 30, wherein the transition-metal compound is present at less than 10 ppm, relative to the weight of the total system.

Embodiment 32

The system of Embodiment 30 or 31, wherein at least one organosilane comprises an organosilane of Formula (I), Formula (II), or Formula (III):

$$(R)_{4-m}Si(H)_m \quad (I)$$

$$(R)_{3-m}(H)_m Si-(CH_2)_q-O_r-Si(R)_{3-p}(H)_p \quad (II)$$

$$R-[-SiH(R)-O-]_n-R \quad (III)$$

where: m and p are are independently 1, 2, or 3; q is 0, 1, 2, 3, 4, 5, or 6; r is 0 or 1; n is 10 to 100; and each R is independently halo (e.g., F, Br, Cl, I) (provided at least one R is contains carbon), optionally substituted $C_{1-12}$ alkyl or heteroalkyl, optionally substituted $C_{1-12}$ alkenyl or heteroalkenyl, optionally substituted $C_{1-12}$ alkynyl or heteroalkynyl, optionally substituted $C_{5-20}$ aryl or $C_{3-20}$ heteroaryl, optionally substituted $C_{6-30}$ alkaryl or heteroalkaryl, optionally substituted $C_{5-30}$ aralkyl or heteroaralkyl, optionally substituted —O—$C_{1-12}$ alkyl or heteroalkyl, optionally substituted —O—$C_{5-20}$ aryl or —O—$C_{3-20}$ heteroaryl, optionally substituted —O—$C_{5-30}$ alkaryl or heteroalkaryl, or optionally substituted —O—$C_{5-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. In some embodiments for Formula (II), q is 0. In some embodiments for Formula (II), r is 0.

Embodiment 33

The system of Embodiment 32, wherein the organosilane is $(R)_3SiH$ or $(R)_2SiH_2$, where R is independently alkoxy, alkyl, alkenyl, aryl, aryloxy, heteroaryl, aralkyl, or heteroaralkyl.

Embodiment 34

The system of any one of Embodiments 30 to 33, wherein the alkali metal hydroxide is sodium hydroxide (NaOH) (or the alkali metal alkoxide is sodium alkoxide).

Embodiment 35

The system of Embodiment 34, wherein the organosilane is $EtMe_2SiH$, $PhMe_2SiH$, $(n-Bu)_3SiH$, $Et_2SiH_2$, $PhMe_2SiH$, $BnMe_2SiH$, $(Me)_2(pyridinyl)SiH$, $(EtO)_3SiH$, or $Me_3Si-SiMe_2H$.

Embodiment 36

The system of any one of Embodiments 30 to 33, wherein the alkali metal hydroxide is potassium hydroxide (KOH) (or the alkali metal alkoxide is potassium alkoxide).

Embodiment 37

The system of Embodiment 36, wherein the organosilane is $EtMe_2SiH$, $PhMe_2SiH$, $(n-Bu)_3SiH$, $Et_2SiH_2$, $(i-Pr)_3SiH$, or $(i-Pr)_2(pyridinyl)SiH$.

Embodiment 38

The system of any one of Embodiments 30 to 37, wherein the organic substrate comprising the terminal alkynyl C—H bond has a formula:

$$R^1-C\equiv C-H,$$

where $R^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene.

Embodiment 39

The system of Embodiment 38, wherein $R^1$ is or comprises an optionally substituted linear alkyl, an optionally substituted branched alkyl, or an optionally substituted cycloalkyl.

Embodiment 40

The system of Embodiment 38, wherein $R^1$ is or comprises an optionally substituted linear heteroalkyl, an optionally substituted branched heteroalkyl, or an optionally substituted heterocycloalkyl.

Embodiment 41

The system of Embodiment 38, wherein $R^1$ is or comprises an optionally substituted aryl, an optionally substituted aralkyl, optionally substituted heteroaryl, or an optionally substituted heteroaralkyl.

Embodiment 42

The system of Embodiment 41, wherein $R^1$ is or comprises an optionally substituted benzene, biphenyl, naphthalene, or anthracene ring structure

Embodiment 43

The system of Embodiment 39, wherein $R^1$ is or comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 44

The system of any one of Embodiments 30 to 43, wherein the organic substrate comprising the terminal alkynyl C—H bond is polymeric.

Embodiment 45

The system of any one of Embodiments 30 to 44, comprising at least two different organosilanes.

Embodiment 46

The system of any one of Embodiments 30 to 45, comprising at least two different organic substrates, each comprising a terminal alkynyl C—H bond.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

General Observations of Experimental Data

Initial investigations with the silylation of acetylene 1 (prop-2-ynyl-cyclohexane, FIG. 2) with $Et_3SiH$ were conducted under reactions conditions used for the silylation of heteroarenes using KOt-Bu-catalyzed $C(sp^2)$-H silylation conditions. In this case, the observed ethynylsilane 2a was obtained in good yield, along with 9% of undesired alkyne migration product 1-iso (FIG. 2, entry 1). NaOt-Bu (entry 2) and LiOt-Bu (entry 3) were inferior catalysts, and common organic bases (entries 4-6) also gave poor results. Surprisingly, the milder KOH was superior to KOt-Bu at 10 mol % catalyst loading (entry 7). Moving from $Et_3SiH$ to $PhMe_2SiH$ permitted the reaction to occur at ambient temperature while still maintaining high yields (entry 8). In sharp contrast to the previously reported heteroarene C—H silylation protocol wherein a strong potassium base is crucial to the reactivity, inexpensive and mild NaOH proved to be the ideal catalyst for the silylation of 1 affording 2b in 93% yield (entry 9). LiOH (entry 10) did not catalyze the reaction (see Table 1, below).

Varying the steric and electronic properties of the hydrosilane partner (FIG. 2) showed that a number of new ethynylsilanes could be produced, including those with synthetically versatile hydride-(2e and 2f), benzyldimethyl-(2g), triisopropyl-(2h), triethoxy-(2i), and 2-dialkylpyridyl-(2j and 2k) substituents on silicon (FIG. 2b). Labile Si—Si bonds that are cleaved under transition metal catalysis or in the presence of nucleophiles or acids are also well tolerated, furnishing 2l in 95% yield. This appears to be the broadest scope of mono- and dihydrosilanes reported to date in the C—H silylation field.

A wide variety of alkynes were shown to be reactive, including those bearing electron-rich and electron-deficient aryl (4a-j), heteroaryl (4k-m), and alkyl (4o-y) groups (FIG. 3). Sensitive functional groups such as aryl halides (4b-d), an alkyl chloride (4v), and cyclopropane (4r) were tolerated without any undesired side reactions. Substrates bearing acidic functionalities such as propargylamine (3w) and propargyl alcohol (3x) also reacted well, providing 4w and bis-silylated 4x respectively in high yields. Unprecedented catalytic cross-dehydrogenative silylation of N-heterocyclic systems, such as pyridine 3m, and imidazole 3k, also successful gave the corresponding silylated building blocks 4m and 4k. Substrates containing C—H bonds that are susceptible to KOt-Bu-catalyzed silylation, or those that are engaged under other C—H functionalization chemistries, such as anisole 3g, thiophene 3y, toluene 3f, propargyl ether 3q, and benzene derivative 3t, all reacted with excellent chemoselectivity (>99:1) at the terminal alkyne C—H bond without any observed $C(sp^2)$-H or $C(sp^3)$-H silylation. The complete suppression of Minisci-type radical functionalizations (e.g., pyridine 3m), and electrophilic substitution reactions (e.g., electron-rich system 3n and ferrocene 3h) suggest that a novel C—H functionalization mechanism is operative. The clean reaction profiles with these substrates demonstrated the unique benefits of catalysis by NaOH compared with transition metal-catalyzed methods and classical stoichiometric deprotonation strategies.

Figure 4D:
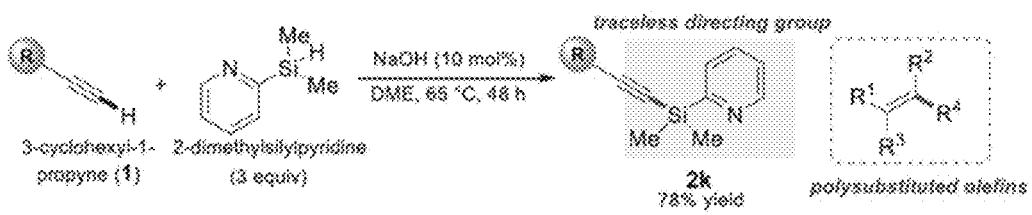

This alkali metal hydroxide-catalyzed silylation reaction scaled well without loss of catalyst activity as demonstrated by the multi-gram synthesis of 4s (FIG. 4A) and can be applied to challenging problems in organic synthesis, materials science, and late stage pharmaceutical derivatization. For example, successful experiments showed that symmetrical aliphatic or aromatic diynes can be bis-silylated (5b and 6b) or selectively mono-functionalized (5a and 6a) generating synthetically valuable, orthogonally activated alkyne building blocks (FIG. 4B). The catalyst's ability to differentiate the alkynes leading to mono-substituted 5a was especially surprising and not presently understood given the lack of electronic communication between the identical alkynes in the starting material. The use of dihydrosilanes allowed for the preparation of symmetrical diethynylsilanes by double C(sp)-H silylation (FIGS. 4C, 7). Simultaneously reacting two different terminal alkynes and a dialkylsilane in a three-component coupling reaction produced unsymmetrical diethynylsilane 8 in 76% yield, along with 10% of 7 (formed by homocoupling of 1) and <5% yield of the homocoupled cyclopropylacetylene product. By taking advantage of the rate differences between the alkyne partners, this non-statistical product distribution favouring the cross product was obtained (see Example 3.4). These silanes are precursors to functionalized siloles, polysiloles or silole-co-polymers, and further embodiments of the present invention provide for the further reactions of the silylated products to this end. Moreover, the hydroxide-catalyzed silylation protocol was employed in the first catalytic installation of the versatile 2-dimethylsilylpyridyl directing group furnishing 2k in 78% yield, which can be advanced to highly substituted olefins (FIG. 4D). Again, further embodiments of the present invention provide for the further reactions of the silylated products to this end.

Figure 4E:
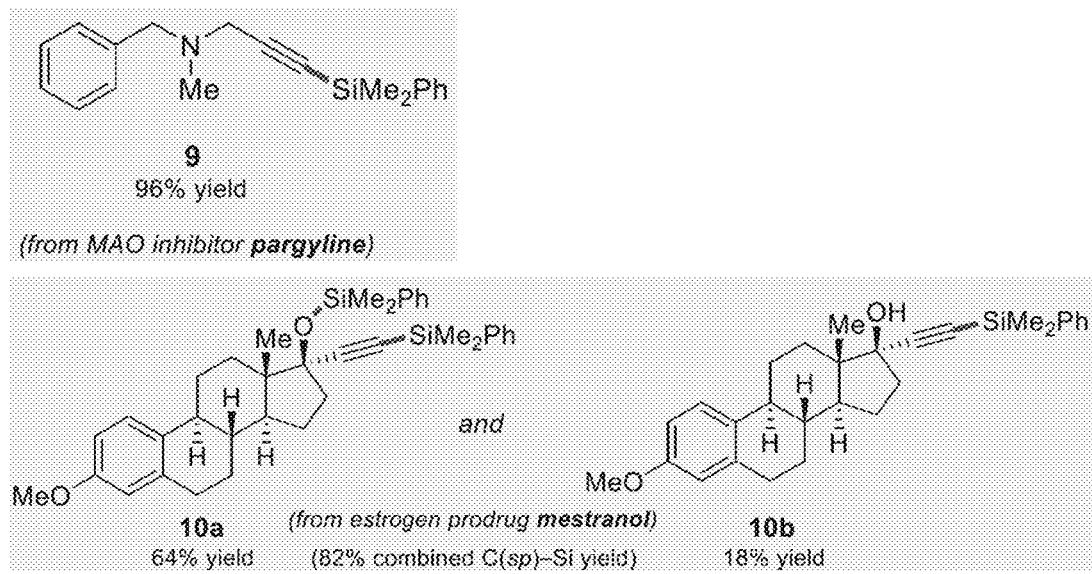

Sila-drug analogues are garnering increased attention from medicinal chemists because they can offer improved pharmacokinetic properties relative to the all-carbon substance. Moreover, the installed organosilicon moiety can serve as a functional group handle for subsequent elaboration or as an easily-removable protecting group. Again, further embodiments of the present invention provide for the further reactions of the silylated products to this end. To evaluate the present methods for such late-stage C—H functionalization applications, the pharmaceutical substances pargyline and mestranol were subjected to the catalytic silylation conditions, successfully providing novel sila-drug analogues 9 and 10 in 96% and 82% yield respectively (FIG. 4E).

Figure 5:
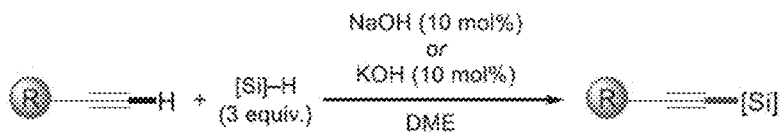
FIG. 5 directly compares the reactivities of KOH and NaOH catalysts under otherwise identical conditions revealing an unanticipated effect on the reaction outcome depending on whether Na$^+$ or K$^+$ is present. R=PhMe$_2$Si (10a); R=H (10b). Reaction conditions are equivalent to those given in FIGS. 3 and 4 for each particular hydrosilane and alkyne. Reactions were conducted on 0.5 mmol scale with 0.5 mL of solvent unless otherwise stated and at the prescribed temperature. Yields are of analytically pure isolated materials. DME=1,2-dimethoxyethane.
Figure 5:
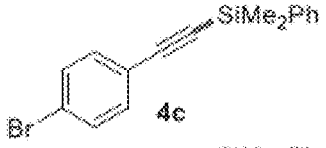
Figure 6:
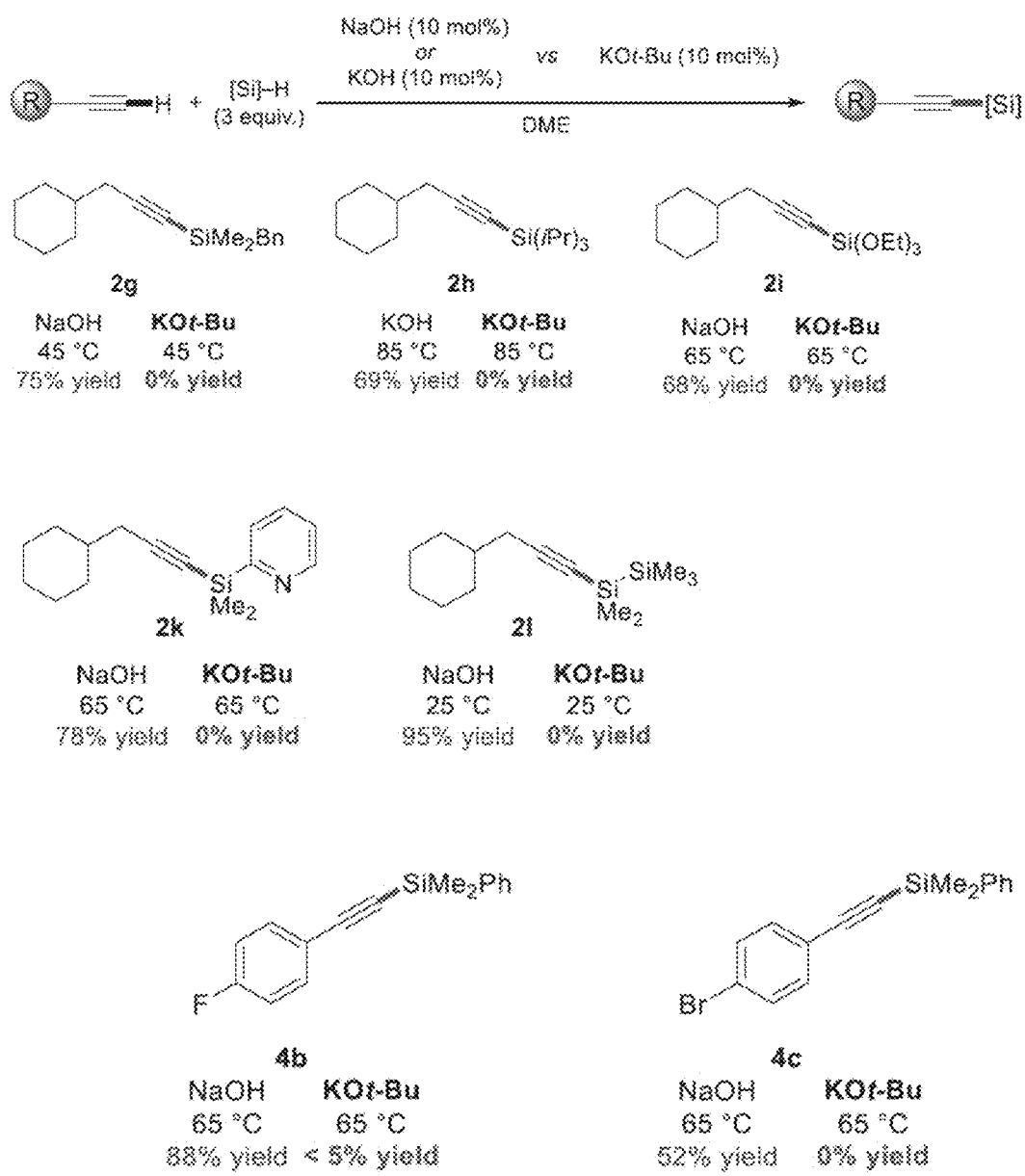
FIG. 6 directly compares the reactivities of NaOH/KOH and KO-tert-BuOH catalysts under otherwise identical conditions revealing an unanticipated benefit of using hydroxide vs. alkoxide under certain conditions.

The underlying mechanistic details of the alkali metal hydroxide, alkoxide, or hydride catalyzed silylation are not well understood at this point. A C—H deprotonation process is conceivable, but raises questions of thermodynamics (i.e., pKa difference between the deprotonating base and the C(sp)-H bond), the mechanism of catalyst turnover, and the nature of the reactive Si species. Preliminary studies further suggest that the mechanism is distinct from previously disclosed C(sp)-H silylation reactions including KOt-Bu-catalyzed $C(sp^2)$-H silylation of heteroarenes. This is based on the results from radical trapping and countercation chelation studies (see Example 2.1.3), the improved yields and greatly expanded hydrosilane and substrate scope compared to previous reports, and the fact that sodium hydroxide shows greatly improved activity compared to precious metal species, Lewis-acids, and KOt-Bu. With respect to the latter, attempting to employ KOt-Bu as the catalyst for the C(sp)-H coupling surprisingly failed in the majority of cases evaluated (see FIG. 6). Moreover, a striking difference in reactivity between KOH and NaOH, which differ only in the identity of the countercation, was observed. The apparent non-innocence of the cation cannot be easily rationalized by solubility, aggregation state, or basicity arguments given the lack of discernible reactivity trends in the substrates investigated under identical conditions (FIG. 5). These data suggest that simple alkali metal cations—either as additives or as catalyst countercations—play an important role in the discovery and development of novel catalytic processes.

Example 2

General Information

Unless otherwise stated, reactions were performed in oven-dried brand-new Fisherbrand scintillation vials in a nitrogen filled glove box or in flame-dried Schlenk flasks under argon connected on a Schlenk line using dry, degassed solvents and brand-new stirring bars. Solvents were dried by passage through an activated alumina column under argon. Reaction progress was monitored by thin-layer chromatography (TLC) or GC-FID analyses. TLC was performed using E. Merck silica gel 60 F254 precoated glass plates (0.25 mm) and visualized by UV fluorescence quenching, phosphomolybdic acid, or $KMnO_4$ staining. Silicycle SiliaFlash P60 Academic Silica gel (particle size 40-63 nm) was used for flash chromatography. $^1$H NMR spectra were recorded on a Varian Inova 500 MHz spectrometer in $CDCl_3$ or THF-d8 and are reported relative to residual solvent peak at δ 7.26 ppm or δ 3.58 ppm respectively. $^{13}$C NMR spectra were recorded on a Varian Inova 500 MHz spectrometer (126 MHz) in $CDCl_3$ or THF-d8 and are reported relative to residual solvent peak at δ 77.16 ppm or δ 67.21 ppm respectively. Data for $^1$H NMR are reported as follows: chemical shift (δ ppm) (multiplicity, coupling constant (Hz), integration). Multiplicities are reported as follows: s=singlet, d=doublet, t=triplet, q=quartet, p=pentet, sept=septet, m=multiplet, br s=broad singlet, br d=broad doublet, app=apparent. Data for $^{13}$C NMR are reported in terms of chemical shifts (δ ppm). IR spectra were obtained on a Perkin Elmer Spectrum BXII spectrometer using thin films deposited on NaCl plates and reported in frequency of absorption ($cm^{-1}$). GC-FID analyses were obtained on an Agilent 6890N gas chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High resolution mass spectra (HRMS) were acquired from the California Institute of Technology Mass Spectrometry Facility. ICP-MS analysis was conducted at the California Institute of Technology Mass Spectrometry Facility.

Silanes were purchased from Aldrich and distilled before use. KOt-Bu was purchased from Aldrich (sublimed grade, 99.99% trace metals basis) and used directly. KOH was purchased from Aldrich (semiconductor grade, pellets, 99.99% trace metals basis) and was pulverized (mortar and pestle) and heated (150° C.) under vacuum prior to use. NaOH was purchased from Aldrich (semiconductor grade, pellets, 99.99% trace metals basis) and was pulverized (mortar and pestle) and heated (150° C.) under vacuum prior to use. Alkyne substrates were purchased from Aldrich, TCI, or Acros.

Example 2.1

Reaction Optimizations, Trace Metal Analysis, and Preliminary Mechanistic Investigations Example 2.1.1

Reaction Optimization

Procedure for reaction condition optimization: In a nitrogen-filled glovebox, catalyst and alkyne 1a (0.1 mmol, 1 equiv) were added to a 2 dram scintillation vial equipped with a magnetic stirring bar. Next, hydrosilane and solvent (0.1 mL) were added. The vial was sealed and the mixture was stirred at the indicated temperature for the indicated time. The vial was then removed from the glovebox, diluted with diethyl ether (1 mL), and concentrated under reduced pressure. The yield was determined by $^1$H NMR or GC analysis of the crude mixture using an internal standard.

TABLE 1

Condition optimization of direct C(sp)—H silylation.

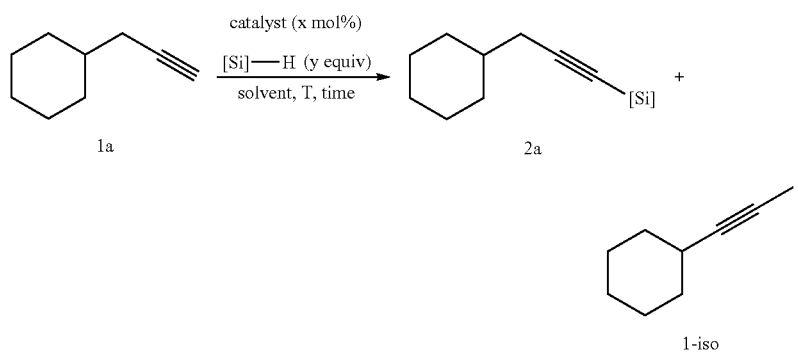

| entry | catalyst | [Si]—H | solvent | T, °C. | time, h | yield 2a | yield 1-iso |
|---|---|---|---|---|---|---|---|
| 1 | KOt-Bu (20 mol%) | Et$_3$SiH | — | 85 | 72 | 22% | 60% |
| 2 | KOt-Bu (20 mol%) | Et$_3$SiH | THF | 85 | 72 | 94% | 1% |
| 3 | KOt-Bu (20 mol%) | Et$_3$SiH | 1,4-dioxane | 85 | 72 | 88% | — |
| 4 | KOt-Bu (20 mol%) | Et$_3$SiH | DME | 85 | 72 | >99% | — |
| 5 | KOt-Bu (20 mol%) | Et$_3$SiH | MTBE | 85 | 72 | 30% | 53% |
| 6 | KOt-Bu (20 mol%) | Et$_3$SiH | toluene | 85 | 72 | 27% | 59% |
| 7 | KOt-Bu (20 mol%) | Et$_3$SiH | CyMe | 85 | 72 | 15% | 66% |
| 8 | KOt-Bu (20 mol%) | Et$_3$SiH | Pentane | 85 | 72 | 13% | 74% |
| 9 | KOt-Bu (20 mol%) | Et$_3$SiH | Mesitylene | 85 | 72 | 26% | 56% |
| 10 | KOt-Bu (20 mol%) | Et$_3$SiH | DCM | 85 | 72 | — | — |
| 11 | KOt-Bu (20 mol%) | Et$_3$SiH | Et$_2$O | 85 | 72 | 23% | 61% |
| 12 | KOt-Bu (20 mol%) | Et$_3$SiH | 2-Me—THF | 85 | 72 | 48% | 51% |
| 13 | KOt-Bu (40 mol%) | Et$_3$SiH | THF | 85 | 48 | 89% | — |
| 14 | KOt-Bu (20 mol%) | Et$_3$SiH | THF | 85 | 48 | 99% | — |
| 15 | KOt-Bu (10 mol%) | Et$_3$SiH | THF | 85 | 48 | >99% | — |
| 16 | KOt-Bu (5 mol%) | Et$_3$SiH | THF | 85 | 48 | 99% | <1% |
| 17 | KOt-Bu (1 mol%) | Et$_3$SiH | THF | 85 | 48 | 97% | 2% |
| 18 | KOt-Bu (10 mol%) | Et$_3$SiH | THF | 25 | 48 | 7% | 63% |
| 19 | KOt-Bu (10 mol%) | Et$_3$SiH | THF | 55 | 48 | 59% | 30% |
| 20 | KH (20 mol%) | Et$_3$SiH | THF | 85 | 72 | 99% | — |
| 21 | KHMDS (20 mol%) | Et$_3$SiH | THF | 85 | 72 | 99% | <1% |
| 22 | NaOt-Bu (20 mol%) | Et$_3$SiH | THF | 85 | 72 | 51% | 40% |
| 23 | LiOt-Bu (20 mol%) | Et$_3$SiH | THF | 85 | 72 | <1% | 5% |
| 24 | DABCO (20 mol%) | Et$_3$SiH | THF | 85 | 72 | <1% | — |
| 25 | NaOEt (20 mol%) | Et$_3$SiH | THF | 85 | 72 | 82% | <1% |
| 26 | KOEt (20 mol%) | Et$_3$SiH | THF | 85 | 72 | 99% | <1% |
| 27 | NaOAc (20 mol%) | Et$_3$SiH | THF | 85 | 72 | <1% | — |
| 28 | KOAc (20 mol%) | Et$_3$SiH | THF | 85 | 72 | <1% | — |
| 29 | KOMe (20 mol%) | Et$_3$SiH | THF | 85 | 72 | 98% | <1% |
| 30 | NaOMe (20 mol%) | Et$_3$SiH | THF | 85 | 72 | 95% | 3% |
| 31 | KOt-amyl (20 mol%) | Et$_3$SiH | THF | 85 | 72 | >99% | <1% |
| 32 | KOH (20 mol%) | Et$_3$SiH | THF | 85 | 72 | 94% | <1% |
| 33 | K$_2$CO$_3$ (20 mol%) | Et$_3$SiH | THF | 85 | 72 | <1% | — |
| 34 | Cs$_2$CO$_3$ (20 mol%) | Et$_3$SiH | THF | 85 | 72 | — | — |
| 35 | KF (20 mol%) | Et$_3$SiH | THF | 85 | 72 | <1% | — |
| 36 | KOt-Bu (10 mol%) | Et$_3$SiH | THF | 85 | 24 | 89% | 9% |
| 37 | KH (10 mol%) | Et$_3$SiH | THF | 85 | 24 | 87% | 11% |
| 38 | NaOt-Bu (10 mol%) | Et$_3$SiH | THF | 85 | 24 | 46% | 2% |
| 39 | LiOt-Bu (10 mol%) | Et$_3$SiH | THF | 85 | 24 | <1% | — |
| 40 | KOEt (10 mol%) | Et$_3$SiH | THF | 85 | 24 | 96% | 2% |
| 41 | NaOEt (10 mol%) | Et$_3$SiH | THF | 85 | 24 | 91% | <1% |
| 42 | KOMe (10 mol%) | Et$_3$SiH | THF | 85 | 24 | 96% | 4% |
| 43 | NaOMe (10 mol%) | Et$_3$SiH | THF | 85 | 24 | 83% | <1% |
| 44 | KOt-Amyl (10 mol%) | Et$_3$SiH | THF | 85 | 24 | 91% | 6% |
| 45 | KOH (10 mol%) | Et$_3$SiH | THF | 85 | 24 | 95% | 3% |
| 46 | NaOH (10 mol%) | Et$_3$SiH | THF | 85 | 24 | 98% | — |
| 47 | LiOH (10 mol%) | Et$_3$SiH | DME | 85 | 24 | 3% | — |
| 48 | Et$_3$N (10 mol%) | Et$_3$SiH | DME | 85 | 48 | 4% | — |
| 49 | Pyridine (10 mol%) | Et$_3$SiH | DME | 85 | 48 | 1% | — |
| 50 | KOH (10 mol%) | Et$_3$SiH (1.0 eq) | THF | 85 | 48 | 71% | 21% |
| 51 | KOH (10 mol%) | Et$_3$SiH (1.5 eq) | THF | 85 | 48 | 92% | 6% |
| 52 | KOH (10 mol%) | Et$_3$SiH (2.0 eq) | THF | 85 | 48 | 93% | 6% |
| 53 | KOH (10 mol%) | Et$_3$SiH (2.5 eq) | THF | 85 | 48 | 97% | 2% |
| 54 | KOH (10 mol%) | Et$_3$SiH (3.0 eq) | THF | 85 | 48 | 98% | 1% |
| 55 | KOH (10 mol%) | Et$_3$SiH (3.5 eq) | THF | 85 | 48 | 99% | 1% |
| 56 | KOH (10 mol%) | Et$_3$SiH (4.0 eq) | THF | 85 | 48 | 97% | 2% |

Yields determined by GC analysis of the crude reaction mixture using an internal standard.

The results from Table 1 reveal that there is a high degree of tunability in the reaction conditions for the C(sp)-H silylation reaction. THF, dioxane, and DME all proved to be suitable solvents, with low amounts of the isomerized starting material produced (Entries 2, 3, 4 respectively). Low loadings of catalyst were achieved with KOt-Bu, down to 1 mol %, without significant loss of yield (Entries 15-17). High temperatures (85° C.) proved necessary for silylation with triethylsilane (Entries 15, 18, 19); as seen in the silane screen in the text, lower temperatures were achieved when employing various other silanes. The extensive base screen (Entries 20-35) with longer reaction times (72 h) showed that there are a number of good catalysts for the C—H silylation reaction. A refined base screen with lower catalyst loading (Entries 36-49) revealed that there were still several catalysts that performed with surprisingly high efficiency, but NaOH proved to be the most convenient and high-performing catalyst. No product was observed in the absence of catalyst, or when LiOt-Bu, NaOAc, KOAc, DABCO, $K_2CO_3$, $Cs_2CO_3$, or KF were employed (Entries 39, 27, 28, 24, 33, 34, 35 respectively).

Example 2.1.2

Trace Metal Analysis by ICP-MS

ICP-MS Trace Metal Analysis of all the Reaction Components.

To provide further support against involvement of adventitious trace metal species in the cross-dehydrogenative C(sp)-H silylation catalysis, inductively coupled plasma mass spectrometry was performed on samples of NaOH, KOH, 3-cyclohexyl-1-propyne starting material, dimethoxyethane (DME) solvent, $PhMe_2SiH$, and a standard reaction mixture that was run under optimal conditions in the glove box. The results from quantitative analysis revealed that most metal contaminants were present below the instrument's lowest limit of detection (i.e., in ppt range or lower). Microgram per liter (ppb) quantities of metal contaminants are given in Table 2.

Samples each of NaOH (1000 mg, 99.99% Aldrich), 3-cyclohexyl-1-propyne, $PhMe_2SiH$, 1,2-dimethoxyethane, and a standard reaction mixture (0.5 mmol scale mixture, prepared following the general procedure with 61.1 mg of 3-cyclohexyl-1-propyne, 2 mg of NaOH, 204.4 mg of $PhMe_2SiH$ in 0.5 mL of 1,2-dimethoxyethane (DME) and stirred in the glovebox for 48 h.) were analyzed.

Each sample was added to a 50 mL DigiTUBE digestion tube (SCP Science) followed by addition of 3.0 mL of Plasma Pure nitric acid (SCP Science) and heating to 75° C. for 36 hours. After digestion, each sample was diluted using Milli Q water to 50 mL and subjected to trace metal analysis. Trace metal concentrations were determined by Inductively Coupled Plasma—Mass Spectrometry using an Agilent 8800. The sample introduction system consisted of a micro-mist nebulizer, scott type spray chamber and fixed injector quartz torch. A guard electrode was used and the plasma was operated at 1500 W. Elements were determined in single-quad mode with either no gas or helium (kinetic energy discrimination mode) in the collision cell. 33 elements were calibrated using external standard solutions ranging from 1 to 100 ppb (micrograms/L). Detection limits of trace elements of concern were below the 1 ppb standard. In addition Quick Scan data in helium mode data were calibrated semiquantitatively. LOD indicated that the analyte concentration is below the instrument's Lowest Limit of Detection. Values are in ppb unless otherwise stated.

TABLE 2

Trace-metal analysis of reactants in the alkyne silylation reaction.

Values in ng/g (ppb) Unless Otherwise Stated*

| Element | NaOH | KOH | 3-cyclohexyl-1-propyne | 1,2-DME | $PhMe_2SiH$ | Reaction Mixture |
|---|---|---|---|---|---|---|
| Ti | LOD | 0.767* | 0.324* | 0.206* | 0.545* | 0.059* |
| Co | LOD | LOD | 18.543 | LOD | LOD | LOD |
| Cu | LOD | LOD | 10.440 | 0.069* | 3.048 | 0.116 |
| Zn | LOD | 0.682* | 25.908* | 1.787* | 0.063* | 0.320 |
| Zr | LOD | LOD | LOD | LOD | 0.232* | LOD |
| Mo | LOD | LOD | LOD | LOD | 1.118* | LOD |
| Ru | LOD | 21.248 | 1.576 | LOD | 41.188 | 18.692 |
| Rh | LOD | 0.165 | LOD | LOD | 0.908 | LOD |
| Pd | LOD | 1.834 | 0.612 | 7.950 | 7.339 | 0.612 |
| Ag | LOD | LOD | LOD | LOD | LOD | LOD |
| Re | LOD | 0.156 | LOD | 0.700 | 5.835 | 0.311 |
| Os | LOD | LOD | LOD | LOD | LOD | LOD |
| Ir | LOD | 0.063* | 7.776* | 0.253* | 2.429* | 0.604 |
| Pt | LOD | 0.406 | 0.135 | 0.813 | 1.490 | 0.271 |
| Au | LOD | LOD | 0.115 | LOD | 1.729 | 1.383 |

*ppm

Example 2.1.3

Preliminary Mechanistic Experiments

A number of experiments were conducted to gain insight into the reaction mechanism. As a first investigation, experiments were conducted in an attempt to determined whether the silylation reaction was polar or radical in nature. The reactions were performed in the presence of the radical traps TEMPO and galvinoxyl. Neither additive thwarted the alkyne C—H silylation: TEMPO did not inhibit the reaction at 10% loading but lowered the silylation yield at 300% loading; the effect of galvinoxyl on the reaction conditions moving from 10 mol % to 300 mol % additive was unexpected and not presently understood (Scheme 1).

Scheme 1. Influence of radical scavengers on the reaction

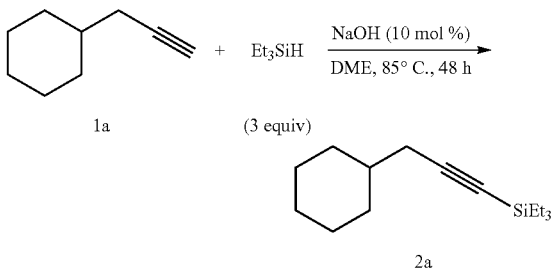

without additive: 99% yield
with galvinoxyl: (10 mol %) 5% yield
(300 mol %) 62% yield
with TEMPO: (10 mol %) 99% yield
(300 mol %) 24% yield

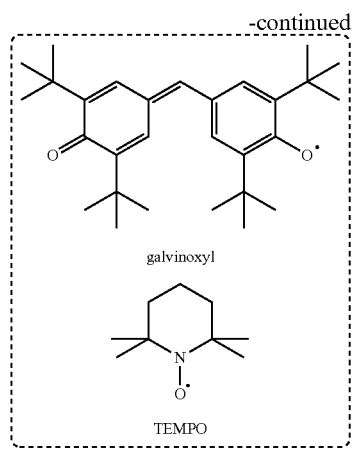

The effect of potassium and sodium chelating agents in the silylation reaction was also studied to investigate the importance of the cation in the catalysis. When 18-crown-6 and 15-crown-5 were added to reactions using KOH and NaOH as the catalysts respectively, quantitative silylation was still observed when using triethylsilane as the silicon partner, suggesting either that ineffective chelation of the metal ion had occurred or that the cation was not necessary to the reactivity in this particular case (Scheme 2a). However, this may be a special case since the reaction with Et₃SiH proceeded equally well using KOH or NaOH as the catalyst.

Scheme 2. Addition of potassium and sodium ion chelators

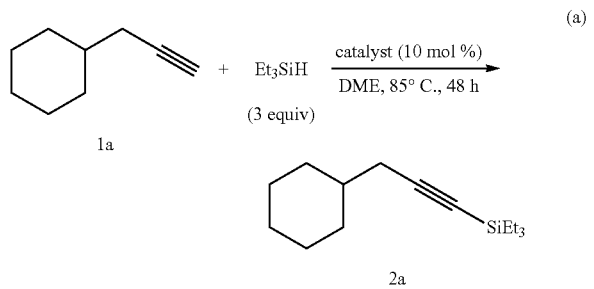

without additive (NaOH or KOH cat.): 99% yield
NaOH with 15-crown-5 (10 mol %):  99% yield
KOH with 18-crown-6 (10 mol %):  99% yield

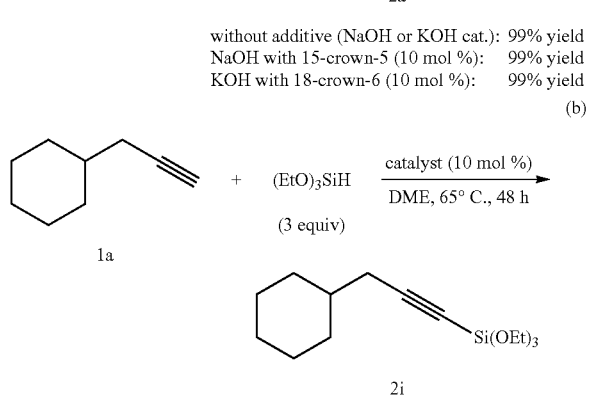

without additive (NaOH or KOH cat.): 99% yield
without additive (KOH cat.):  0% yield
NaOH with 15-crown-5 (10 mol %):  0% yield
KOH with 18-crown-6 (10 mol %):  0% yield The effect of potassium and sodium chelating agents affect silylation was also explored using a silicon partner that does not perform equally well with KOH and NaOH. Triethoxysilane was chosen as the test silane, since it only displays product formation using NaOH as the catalyst. In this case, the addition of potassium and sodium chelating agents shut down reactivity, indicating that the sodium ion is indeed necessary for the silylation of alkynes with triethoxysilane (Scheme 2b). The only product when crown ethers were added is (EtO)₄Si, which indicates that sequestration of the alkali metal cation from the system shut down the productive C—H silylation pathway and induced disproportionation of the silane. Yields were by GC and NMR analysis.

Example 2.1.4

Comparison of MOH and KOt-Bu Catalysts

In order to compare the performance of the newly-discovered MOH (alkali metal hydroxide) catalysts with the KOt-Bu catalyst used in the case of the heterocyclic silylation, several acetylene substrates and silanes were subjected to the reaction using KOt-Bu as a catalyst. The results are summarized in FIG. 6. Although in the reaction with cyclohexylpropyne and triethylsilane, KOt-Bu successfully produced the silylated alkyne in moderate yield (as stated in text), in all other investigated cases, KOt-Bu failed to convert the starting material or produced only trace product. It appears that the acetylinic silylation described herein and the heterocyclic silylation described previously require different catalysts and might proceed via a distinct mechanism.

Example 3

Experimental and Analytics

Example 3.1

General Procedure for Cross-Dehydrogenative C(Sp)-H Silylation and Characterization Data

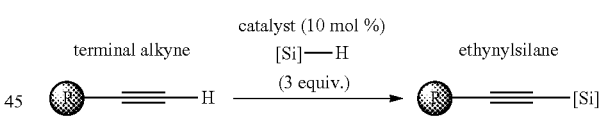

In a nitrogen-filled glove box, catalyst (0.05 mmol, 10 mol %) and alkyne (0.5 mmol, 1 equiv) were added to a 2 dram scintillation vial equipped with a magnetic stirring bar, followed by solvent (0.5 mL) and silane (1.5 mmol, 3 equiv). The vial was then sealed and the mixture was stirred at the indicated temperature for the indicated time. The vial was then removed from the glove box; the reaction mixture was diluted with diethyl ether (2 mL), filtered through a short pad of silica gel, and concentrated under reduced pressure. Volatiles were removed under high vacuum with heating as indicated and the resultant material was purified by silica gel flash chromatography if necessary to give the desired C(sp)-Si product.

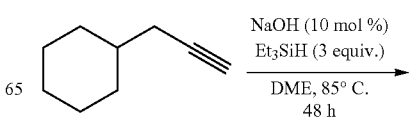

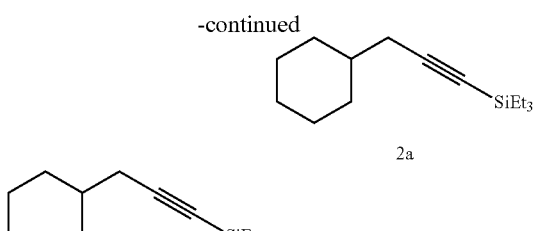

(3-Cyclohexylprop-1-yn-1-yl)triethylsilane 2a

The general procedure was followed. The reaction was performed with NaOH (2.0 mg, 0.05 mmol, 10 mol %), cyclohexylpropyne (61 mg, 0.5 mmol, 1.0 equiv), Et$_3$SiH (174 mg, 240 μL, 1.5 mmol, 3.0 equiv), and 0.5 mL of 1,2-dimethoxyethane (DME) at 85° C. for 48 h. The desired product 2a (111.9 mg, 95% yield) was obtained after solvent removal under high vacuum (45 mtorr, 2 hours) as a colorless oil. $^1$H NMR (500 MHz, CDCl$_3$) δ 2.13 (d, J=6.6 Hz, 2H), 1.84-1.76 (m, 2H), 1.75-1.68 (m, 2H), 1.65 (dtt, J=12.9, 3.4, 1.5 Hz, 1H), 1.47 (dddd, J=14.8, 6.8, 4.7, 3.4 Hz, 1H), 1.24 (tdd, J=15.9, 9.4, 3.4 Hz, 2H), 1.19-1.07 (m, 2H), 1.07-1.01 (m, 1H), 0.98 (t, J=7.9 Hz, 9H), 0.57 (q, J=7.9 Hz, 6H); $^{13}$C NMR (126 MHz, CDCl$_3$) δ 107.73, 82.39, 37.54, 32.72, 27.86, 26.47, 26.32, 7.65, 4.75. IR (Neat Film NaCl) 3422, 2925, 2172, 1645, 1449, 1018, 802, 724 cm$^{-1}$; HRMS (EI+) calc'd for C$_{15}$H$_{27}$Si [(M+H)—H$_2$]: 235.1882, found 235.1881.

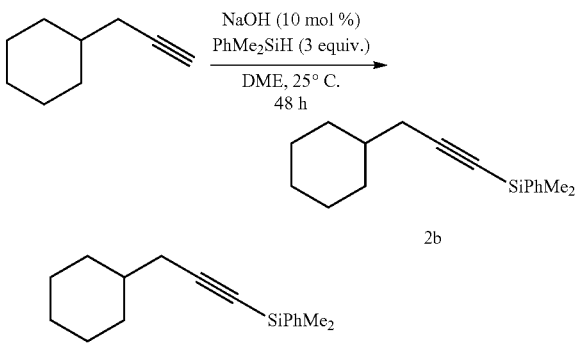

(3-Cyclohexylprop-1-yn-1-yl)dimethyl(phenyl)silane 2b

The general procedure was followed. The reaction was performed with NaOH (2.0 mg, 0.05 mmol, 10 mol %), cyclohexylpropyne (61 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 25° C. for 48 h. The desired product 2b (113.6 mg, 89% yield) was obtained in 95% purity after heating to 85° C. at 45 mtorr for 30 minutes; subsequent purification by silica gel flash chromatography (100% hexanes) yielded the product 2b in analytically pure form as a colorless oil. R$_f$=0.67 (100% hexanes); $^1$H NMR (500 MHz, CDCl$_3$) δ 7.67-7.63 (m, 2H), 7.40-7.34 (m, 3H), 2.19 (d, J=6.6 Hz, 2H), 1.87-1.80 (m, 2H), 1.74 (dt, J=12.8, 3.3 Hz, 2H), 1.67 (dddd, J=11.3, 5.2, 3.3, 1.6 Hz, 1H), 1.52 (ddtd, J=14.9, 11.5, 6.7, 3.5 Hz, 1H), 1.27 (dddd, J=15.9, 12.6, 9.5, 3.3 Hz, 2H), 1.15 (qt, J=12.7, 3.3 Hz, 1H), 1.08-0.98 (m, 2H), 0.41 (s, 6H); $^{13}$C NMR (126 MHz, CDCl$_3$) δ 137.93, 133.81, 129.33, 127.91, 108.67, 83.19, 37.42, 32.81, 27.94, 26.42, 26.29, −0.38. IR (Neat Film NaCl) 3420, 2924, 2852, 2173, 1646, 1448, 1427, 1322, 1248, 1115, 1071, 1027, 815, 730 cm$^{-1}$; HRMS (EI+) calc'd for C$_{17}$H$_{25}$Si [M+H]: 257.1726, found 257.1720.

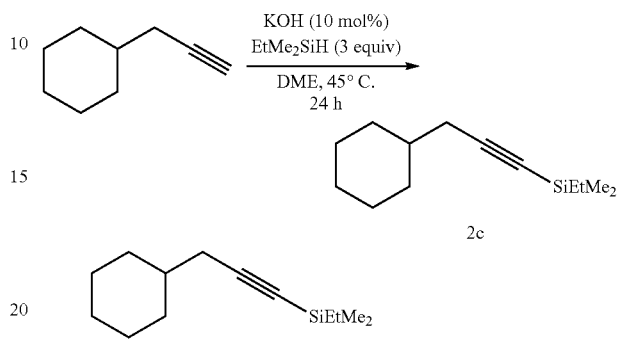

3-Cyclohexylprop-1-yn-1-yl)(ethyl)dimethylsilane 2c

The general procedure was followed. The reaction was performed with KOH (2.8 mg, 0.05 mmol, 10 mol %), cyclohexylpropyne (61 mg, 0.5 mmol, 1.0 equiv), EtMe$_2$SiH (132 mg, 198 μL, 1.5 mmol, 3.0 equiv), and 0.5 mL of 1,2-dimethoxyethane (DME) at 45° C. for 24 h. The desired product 2c (95.1 mg, 91% yield) was obtained after solvent removal under high vacuum (45 mtorr, 2 hours) as a colorless oil. $^1$H NMR (500 MHz, CDCl$_3$) δ 2.12 (d, J=6.6 Hz, 2H), 1.86-1.76 (m, 2H), 1.77-1.69 (m, 2H), 1.66 (dtd, J=12.6, 3.3, 1.6 Hz, 1H), 1.53-1.40 (m, 1H), 1.32-1.19 (m, 2H), 1.20-1.07 (m, 2H), 1.06-0.94 (m, 4H), 0.57 (q, J=7.9 Hz, 2H), 0.12 (s, 6H); $^{13}$C NMR (126 MHz, CDCl$_3$) δ 107.01, 84.30, 37.46, 32.76, 27.84, 26.45, 26.30, 8.47, 7.50, −1.85. IR (Neat Film NaCl) 3422, 2922, 2103, 1646, 1558, 1260, 1027, 720 cm$^{-1}$; HRMS (EI+) calc'd for C$_{13}$H$_{23}$Si [(M+H)—H$_2$]: 207.1569, found 207.1562.

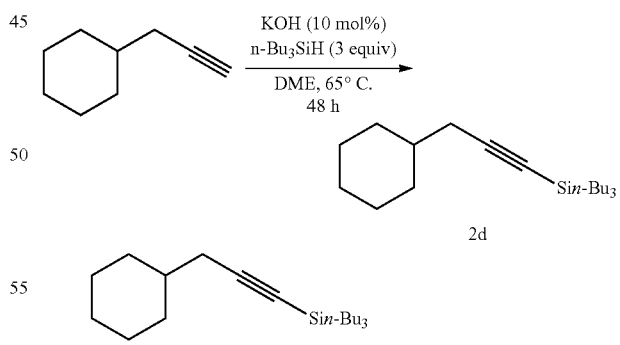

Tributyl(3-cyclohexylprop-1-yn-1-yl)silane 2d

The general procedure was followed. The reaction was performed with KOH (2.8 mg, 0.05 mmol, 10 mol %), cyclohexylpropyne (61 mg, 0.5 mmol, 1.0 equiv), n-Bu$_3$SiH (301 mg, 386 μL, 1.5 mmol, 3.0 equiv), and 0.5 mL of 1,2-dimethoxyethane (DME) at 65° C. for 48 h. The desired product 2d (117.2 mg, 73% yield) was obtained by silica gel flash chromatography (100% hexanes) yielded the product 2d as a colorless oil. $R_f$=0.78 (100% hexanes); $^1$H NMR (500 MHz, CDCl$_3$) δ 2.18 (d, J=6.5 Hz, 2H), 1.85 (dddd, J=12.3, 6.2, 3.1, 1.8 Hz, 2H), 1.77 (ddd, J=14.0, 4.5, 2.3 Hz, 2H), 1.70 (dddt, J=12.8, 5.1, 3.3, 1.5 Hz, 1H), 1.52 (dddt, J=14.5, 7.9, 6.6, 3.2 Hz, 1H), 1.43-1.36 (m, 12H), 1.29 (qt, J=12.6, 3.3 Hz, 2H), 1.18 (qt, J=12.7, 3.3 Hz, 1H), 1.11-1.02 (m, 2H), 0.97-0.91 (m, 9H), 0.67-0.59 (m, 6H); $^{13}$C NMR (126 MHz, CDCl$_3$) δ 107.65, 83.25, 37.57, 32.72, 27.88, 26.64, 26.46, 26.39, 26.32, 13.98, 13.45. IR (Neat Film NaCl) 2955, 2922, 2854, 2172, 1449, 1376, 1191, 1080, 1029, 886, 758, 708 cm$^{-1}$; HRMS (EI+) calc'd for C$_{21}$H$_{40}$Si [M+•]: 320.2899, found 320.2905.

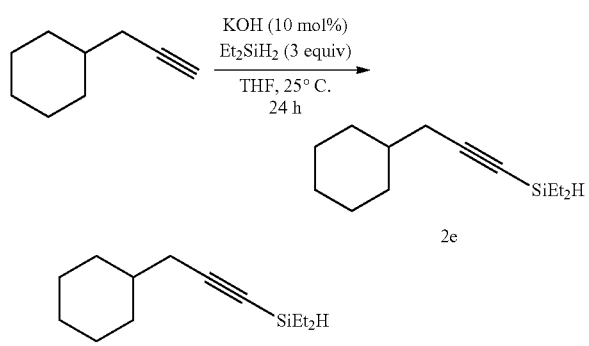

(3-Cyclohexylprop-1-yn-1-yl)diethylsilane 2e

The general procedure was followed. The reaction was performed with KOH (2.8 mg, 0.05 mmol, 10 mol %), cyclohexylpropyne (61 mg, 0.5 mmol, 1.0 equiv), Et$_2$SiH$_2$ (132 mg, 194 μL, 1.5 mmol, 3.0 equiv), and 0.5 mL of tetrahydrofuran (THF) at 25° C. for 24 h. The desired product 2e (73.6 mg, 71% yield) was obtained in 90% purity after solvent removal under high vacuum at 45 mtorr for 30 minutes; subsequent purification by silica gel flash chromatography (100% hexanes) yielded the product 2e as a colorless oil. $R_f$=0.77 (100% hexanes); $^1$H NMR (500 MHz, CDCl$_3$) δ 3.92 (pt, J=3.2, 1.2 Hz, 1H), 2.15 (dd, J=6.7, 1.2 Hz, 2H), 1.85-1.78 (m, 2H), 1.72 (ddd, J=13.9, 4.5, 2.2 Hz, 2H), 1.66 (dddt, J=12.7, 5.1, 3.3, 1.5 Hz, 1H), 1.49 (ddtd, J=14.9, 11.5, 6.8, 3.5 Hz, 1H), 1.31-1.20 (m, 2H), 1.15 (tt, J=12.6, 3.2 Hz, 1H), 1.07-0.95 (m, 8H), 0.70-0.64 (m, 4H); $^{13}$C NMR (126 MHz, CDCl$_3$) δ 109.00, 80.24, 37.39, 32.76, 27.91, 26.41, 26.28, 8.09, 4.23. IR (Neat Film NaCl) 3422, 2957, 2174, 2120, 1646, 1558, 1457, 1260, 1055, 804 cm$^{-1}$; HRMS (EI+) calc'd for C$_{13}$H$_{23}$Si [(M+H)—H$_2$]: 207.1569, found 207.1562.

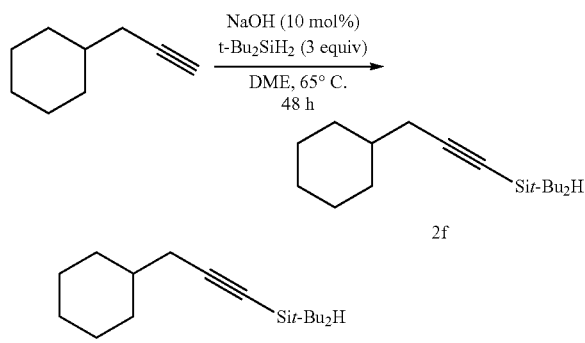

Di-tert-butyl(3-cyclohexylprop-1-yn-1-yl)silane 2f

The general procedure was followed. The reaction was performed with NaOH (2.0 mg, 0.05 mmol, 10 mol %), cyclohexylpropyne (61 mg, 0.5 mmol, 1.0 equiv), t-Bu$_2$SiH$_2$ (216 mg, 297 μL, 1.5 mmol, 3.0 equiv), and 0.5 mL of 1,2-dimethoxyethane (DME) at 65° C. for 48 h. The desired product 2f (120.3 mg, 91% yield) was obtained in 90% purity after high vacuum at 45 mtorr for 30 minutes; subsequent purification by silica gel flash chromatography (100% hexanes) yielded the product 2f as a colorless oil. $R_f$=0.88 (100% hexanes); $^1$H NMR (500 MHz, CDCl$_3$) δ 3.57 (t, J=1.2 Hz, 1H), 2.17 (dd, J=6.5, 1.2 Hz, 2H), 1.84-1.78 (m, 2H), 1.76-1.70 (m, 2H), 1.66 (dddt, J=12.8, 5.1, 3.3, 1.5 Hz, 1H), 1.50 (dddt, J=14.5, 7.8, 6.5, 3.1 Hz, 1H), 1.26 (qt, J=12.7, 3.4 Hz, 3H), 1.19-1.09 (m, 2H), 1.06 (s, 18H).; $^{13}$C NMR (126 MHz, CDCl$_3$) δ 108.94, 79.54, 37.51, 32.75, 28.28, 27.88, 26.44, 26.29, 18.63. IR (Neat Film NaCl) 2958, 2927, 2855, 2173, 2111, 1469, 1449, 1363, 1028, 1012, 810, 793, 617 cm$^{-1}$; HRMS (EI+) calc'd for C$_{17}$H$_{31}$Si [(M+H)—H$_2$]: 263.2195, found 263.2206.

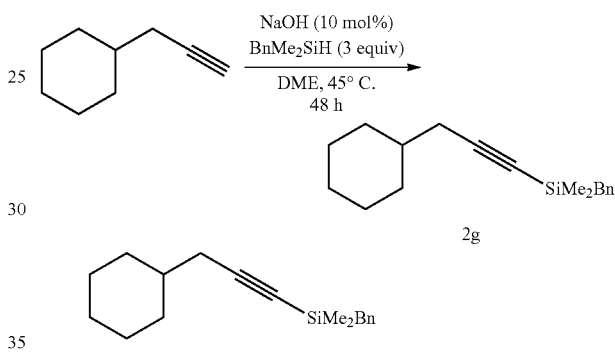

Benzyl(3-cyclohexylprop-1-yn-1-yl)dimethylsilane 2g

The general procedure was followed. The reaction was performed with NaOH (2.0 mg, 0.05 mmol, 10 mol %), cyclohexylpropyne (61 mg, 0.5 mmol, 1.0 equiv), BnMe$_2$SiH (150 mg, 238 μL, 1.5 mmol, 3.0 equiv), and 0.5 mL of 1,2-dimethoxyethane (DME) at 45° C. for 48 h. The desired product 2g (101.9 mg, 75% yield) was obtained by silica gel flash chromatography (100% hexanes) as a colorless oil. $R_f$=0.51 (100% hexanes); $^1$H NMR (500 MHz, CDCl$_3$) δ 7.25-7.21 (m, 2H), 7.12-7.08 (m, 3H), 2.20 (s, 2H), 2.14 (d, J=6.8 Hz, 2H), 1.81 (ddd, J=13.3, 3.5, 1.5 Hz, 2H), 1.75 (dt, J=12.7, 3.2 Hz, 2H), 1.69 (dddd, J=11.3, 5.3, 3.4, 1.7 Hz, 1H), 1.49 (tdt, J=11.4, 6.7, 3.3 Hz, 1H), 1.28 (qt, J=12.6, 3.3 Hz, 2H), 1.16 (qt, J=12.7, 3.3 Hz, 1H), 1.06-0.94 (m, 2H), 0.13 (s, 6H); $^{13}$C NMR (126 MHz, CDCl$_3$) δ 139.44, 128.51, 128.19, 124.32, 108.08, 83.69, 37.38, 32.77, 27.86, 26.71, 26.41, 26.29, −1.69. IR (Neat Film NaCl) 3081, 3060, 3024, 2999, 2922, 2851, 2664, 2173, 1936, 1600, 1493, 1449, 1422, 1408, 1368, 1322, 1249, 1207, 1155, 1056, 1029, 947, 839, 761, 697 cm$^{-1}$; HRMS (EI+) calc'd for C$_{18}$H$_{26}$Si [M+•]: 270.1804, found 270.1810.

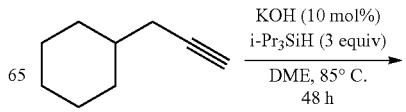

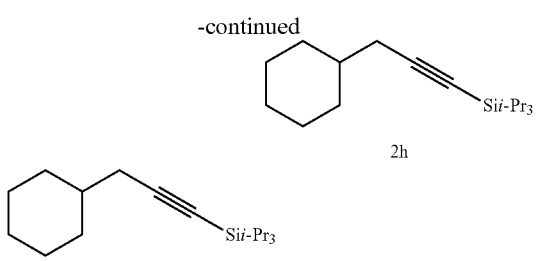

(3-Cyclohexylprop-1-yn-1-yl)triisopropylsilane 2h

The general procedure was followed. The reaction was performed with KOH (2.8 mg, 0.05 mmol, 10 mol %), cyclohexylpropyne (61 mg, 0.5 mmol, 1.0 equiv), i-Pr$_3$SiH (238 mg, 307 µL, 1.5 mmol, 3.0 equiv), and 0.5 mL of 1,2-dimethoxyethane (DME) at 85° C. for 48 h. The desired product 2h (95.6 mg, 69% yield) was obtained by silica gel flash chromatography (100% hexanes) as a colorless oil. $R_f$=0.79 (100% hexanes); $^1$H NMR (500 MHz, CDCl$_3$) δ 2.16 (d, J=6.4 Hz, 2H), 1.84-1.77 (m, 2H), 1.73 (dt, J=12.8, 3.4 Hz, 2H), 1.66 (dtd, J=12.7, 3.3, 1.6 Hz, 1H), 1.48 (ddtd, J=14.6, 11.2, 6.5, 3.4 Hz, 1H), 1.25 (qt, J=12.6, 3.4 Hz, 2H), 1.15 (tt, J=12.6, 3.3 Hz, 1H), 1.10-0.99 (m, 23H); $^{13}$C NMR (126 MHz, CDCl$_3$) δ 108.17, 80.94, 37.64, 32.71, 27.87, 26.49, 26.33, 18.80, 11.48. IR (Neat Film NaCl) 2924, 2864, 2170, 2463, 1449, 1264, 1025, 995, 883, 743, 676, 633 cm$^{-1}$; HRMS (EI+) calc'd for C$_{18}$H$_{33}$Si [(M+H)—H$_2$]: 277.2352, found 277.2349.

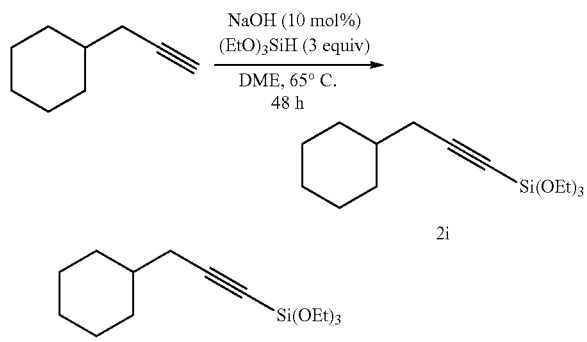

(3-Cyclohexylprop-1-yn-1-yl)triethoxysilane 2i

The general procedure was followed. The reaction was performed with NaOH (2.0 mg, 0.05 mmol, 10 mol %), cyclohexylpropyne (61 mg, 0.5 mmol, 1.0 equiv), (EtO)$_3$SiH (246 mg, 277 µL, 1.5 mmol, 3.0 equiv), and 0.5 mL of 1,2-dimethoxyethane (DME) at 65° C. for 48 h. The desired product 2i (97.1 mg, 68% yield) was obtained by silica gel flash chromatography (5% Et$_2$O in hexanes) as a colorless oil. $R_f$=0.41 (5% Et$_2$O in hexanes); $^1$H NMR (500 MHz, CDCl$_3$) δ 3.87 (q, J=7.0 Hz, 6H), 2.16 (d, J=6.6 Hz, 2H), 1.84-1.78 (m, 2H), 1.72 (dp, J=12.6, 3.7 Hz, 2H), 1.66 (dddt, J=12.8, 5.1, 3.3, 1.5 Hz, 1H), 1.52 (ddtd, J=14.9, 11.5, 6.8, 3.5 Hz, 1H), 1.26 (t, J=7.0 Hz, 9H), 1.24-1.19 (m, 2H), 1.13 (qt, J=12.7, 3.3 Hz, 1H), 1.02 (qd, J=12.7, 3.5 Hz, 2H); $^{13}$C NMR (126 MHz, CDCl$_3$) δ 106.50, 76.85, 59.02, 37.10, 32.74, 27.55, 26.33, 26.20, 18.18. IR (Neat Film NaCl) 2974, 2925, 2852, 2182, 1449, 1390, 1168, 1101, 1079, 1036, 964, 790, 721 cm$^{-1}$; HRMS (EI+) calc'd for C$_{15}$H$_{29}$O$_3$Si [M+H]: 285.1886, found 285.1889.

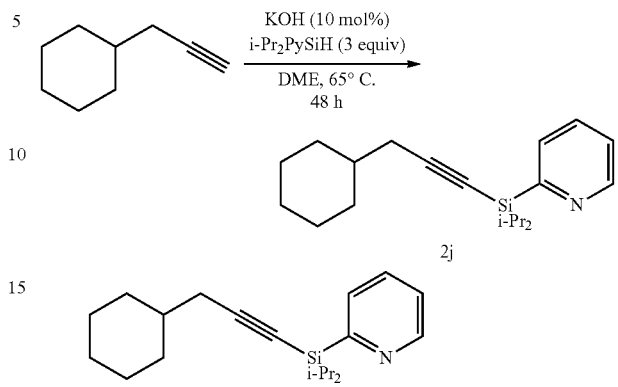

2-((3-Cyclohexylprop-1-yn-1-yl)diisopropylsilyl)pyridine 2j

The general procedure was followed. The reaction was performed with KOH (2.8 mg, 0.05 mmol, 10 mol %), cyclohexylpropyne (61 mg, 0.5 mmol, 1.0 equiv), i-Pr$_2$(Pyr)SiH (290 mg, 322 µL, 1.5 mmol, 3.0 equiv), and 0.5 mL of 1,2-dimethoxyethane (DME) at 65° C. for 48 h. The desired product 2j (122.5 mg, 78% yield) was obtained by silica gel flash chromatography (10% EtOAc in hexanes) as a colorless oil. $R_f$=0.47 (10% EtOAc in hexanes); $^1$H NMR (500 MHz, THF-d8) δ 8.65 (ddd, J=4.8, 1.7, 1.1 Hz, 1H), 7.76 (dt, J=7.5, 1.3 Hz, 1H), 7.59 (td, J=7.6, 1.8 Hz, 1H), 7.19 (ddd, J=7.7, 4.8, 1.4 Hz, 1H), 2.26 (d, J=6.4 Hz, 2H), 1.95-1.84 (m, 2H), 1.78-1.73 (m, 2H), 1.67 (dtt, J=13.0, 3.4, 1.6 Hz, 1H), 1.55 (ddtd, J=14.9, 11.4, 6.6, 3.5 Hz, 1H), 1.37-1.26 (m, 4H), 1.21-1.16 (m, 1H), 1.16-1.11 (m, 2H), 1.09 (d, J=7.4 Hz, 6H), 0.99 (d, J=7.3 Hz, 6H); $^{13}$C NMR (126 MHz, THF-d8) δ 164.80, 150.76, 134.42, 132.12, 123.73, 110.50, 80.33, 38.63, 33.66, 28.41, 27.38, 27.23, 18.46, 18.40, 12.71. IR (Neat Film NaCl) 2924, 2862, 2170, 1573, 1462, 1449, 1417, 1136, 1081, 1028, 995, 882, 747, 723 cm$^{-1}$; HRMS (EI+) calc'd for C$_{20}$H$_{32}$NSi [M+H]: 314.2304, found 314.2311.

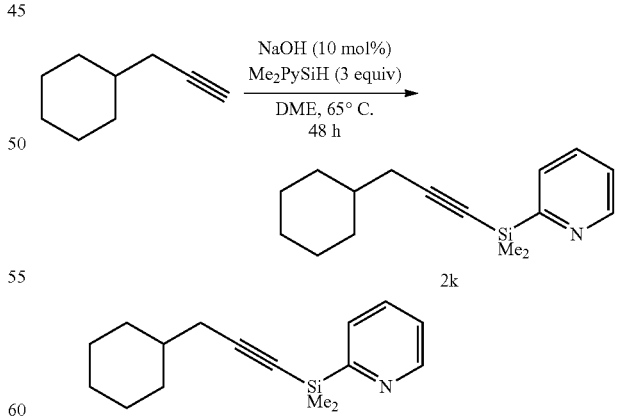

2-((3-Cyclohexylprop-1-yn-1-yl)dimethylsilyl)pyridine 2k

The general procedure was followed. The reaction was performed with NaOH (2.0 mg, 0.05 mmol, 10 mol %), cyclohexylpropyne (61 mg, 0.5 mmol, 1.0 equiv), Me$_2$(Py)SiH (206 mg, 225 μL, 1.5 mmol, 3.0 equiv), and 0.5 mL of 1,2-dimethoxyethane (DME) at 65° C. for 48 h. The desired product 2k (99.9 mg, 78% yield) was obtained by silica gel flash chromatography (10% EtOAc in hexanes) as a colorless oil. R$_f$=0.42 (10% EtOAc in hexanes); $^1$H NMR (500 MHz, THF-d8) δ 8.65 (ddd, J=4.8, 1.8, 1.1 Hz, 1H), 7.74 (dt, J=7.5, 1.2 Hz, 1H), 7.59 (td, J=7.6, 1.8 Hz, 1H), 7.18 (ddd, J=7.7, 4.8, 1.4 Hz, 1H), 2.19 (d, J=6.6 Hz, 2H), 1.88-1.81 (m, 2H), 1.73-1.70 (m, 2H), 1.66 (dddd, J=12.7, 5.1, 3.2, 1.5 Hz, 1H), 1.50 (dddt, J=14.7, 7.9, 6.7, 3.2 Hz, 1H), 1.28 (tdd, J=16.0, 9.4, 3.4 Hz, 2H), 1.17 (qt, J=12.7, 3.3 Hz, 1H), 1.05 (qd, J=12.8, 3.4 Hz, 2H), 0.36 (s, 6H); $^{13}$C NMR (126 MHz, THF-d8) δ 166.55, 150.96, 134.69, 130.13, 123.84, 109.23, 83.58, 38.47, 33.68, 28.42, 27.34, 27.22, −1.00. IR (Neat Film NaCl) 3423, 2924, 2852, 2175, 1646, 1449, 1255, 1044, 832, 797, 676 cm$^{-1}$; HRMS (EI+) calc'd for C$_{16}$H$_{24}$NSi [M+H]: 258.1678. found 258.1672.

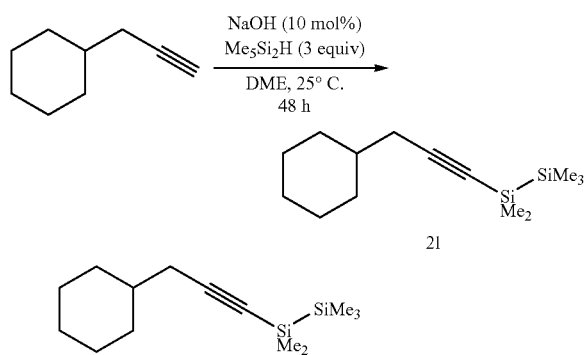

1-(3-Cyclohexylprop-1-yn-1-yl)-1,1,2,2,2-pentamethyldisilane 2l

The general procedure was followed. The reaction was performed with NaOH (2.0 mg, 0.05 mmol, 10 mol %), cyclohexylpropyne (61 mg, 0.5 mmol, 1.0 equiv), Me$_5$Si$_2$H (246 mg, 277 μL, 1.5 mmol, 3.0 equiv), and 0.5 mL of 1,2-dimethoxyethane (DME) at 25° C. for 48 h. The desired product 2l (120.0 mg, 95% yield) was obtained as a cloudy, colorless oil after solvent removal at 85° C. at 45 mtorr for 30 minutes. $^1$H NMR (500 MHz, THF-d8) δ 2.11 (d, J=6.5 Hz, 2H), 1.81 (dddd, J=13.1, 6.1, 3.1, 1.9 Hz, 2H), 1.73-1.69 (m, 2H), 1.65 (dddt, J=12.7, 5.1, 3.2, 1.5 Hz, 1H), 1.44 (dddt, J=14.6, 8.0, 6.7, 3.2 Hz, 1H), 1.33-1.21 (m, 2H), 1.15 (qt, J=12.7, 3.2 Hz, 1H), 1.03 (qd, J=12.8, 3.5 Hz, 2H), 0.15 (s, 6H), 0.11 (s, 9H); $^{13}$C NMR (126 MHz, THF-d8) δ 109.11, 84.06, 38.62, 33.61, 28.52, 27.37, 27.22, −2.25, −2.35. IR (Neat Film NaCl) 2923, 2852, 2168, 1449, 1259, 1244, 1077, 1027, 871, 833, 799, 765, 725, 691, 667 cm$^{-1}$; HRMS (EI+) calc'd for C$_{14}$H$_{28}$Si$_2$ [M+•]: 252.1730, found 252.1737.

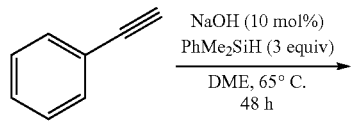

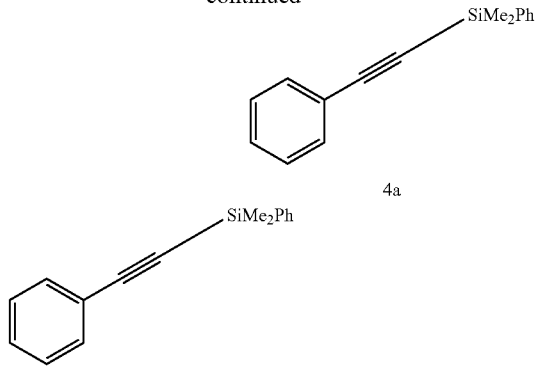

Dimethyl(phenyl)(phenylethynyl)silane 4a

The general procedure was followed. The reaction was performed with NaOH (2.0 mg, 0.05 mmol, 10 mol %), ethynylbenzene (52 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 4a (105.7 mg, 89% yield) was obtained in 95% purity after heating to 85° C. at 45 mtorr for 30 minutes; subsequent purification by silica gel flash chromatography (100% hexanes) yielded the product 4a in analytically pure form as a colorless oil. R$_f$=0.38 (100% hexanes); $^1$H NMR (500 MHz, THF-d8) δ 7.71-7.65 (m, 2H), 7.49-7.44 (m, 2H), 7.38-7.28 (m, 6H), 0.46 (s, 6H). $^{13}$C NMR (126 MHz, THF-d8) δ 137.86, 134.66, 132.88, 130.35, 129.75, 129.28, 128.79, 124.15, 107.86, 92.55, −0.50. IR (Neat Film NaCl) 3068, 3051, 2959, 2899, 2158, 1592, 1488, 1442, 1428, 1278, 1250, 1219, 1118, 1068, 1026, 846, 807, 780, 731, 690 cm$^{-1}$; HRMS (EI+) calc'd for C$_{16}$H$_{17}$Si [M+H]: 237.1100, found 237.1101.

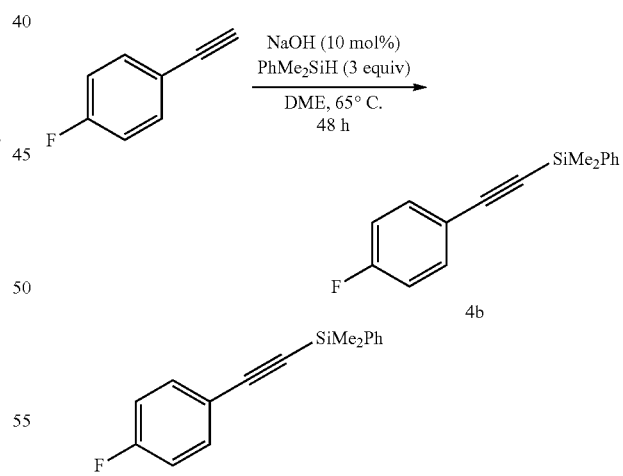

((4-Fluorophenyl)ethynyl)dimethyl(phenyl)silanepyridine 4b

The general procedure was followed. The reaction was performed with NaOH (2.0 mg, 0.05 mmol, 10 mol %), 1-ethynyl-4-fluorobenzene (60 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 4b (111.9 mg, 88% yield) was obtained in 95% purity after solvent removal at 85° C. at 45 mtorr for 30 minutes; subsequent purification by silica gel flash chromatography (100% hexanes) yielded the product 4b in analytically pure form as a colorless oil. $R_f$=0.49 (100% hexanes); $^1$H NMR (500 MHz, THF-d8) δ 7.68-7.65 (m, 2H), 7.53-7.48 (m, 2H), 7.34 (dd, J=4.9, 1.9 Hz, 3H), 7.08 (t, J=8.8 Hz, 2H), 0.46 (s, 6H); $^{13}$C NMR (126 MHz, THF-d8) δ 163.93 (d, J=248.7 Hz), 137.74, 135.10 (d, J=8.5 Hz), 134.65, 130.39, 128.81, 120.43 (d, J=3.5 Hz), 116.51 (d, J=22.4 Hz), 106.68, 92.43 (d, J=1.3 Hz), −0.56. IR (Neat Film NaCl) 3420, 3069, 2961, 2160, 1653, 1600, 1505, 1428, 1251, 1233, 1155, 1117, 1092, 857, 835, 816, 781, 731, 698 cm$^{-1}$; HRMS (EI+) calc'd for $C_{16}H_{16}FSi$ [M+H]: 255.1005, found 255.1000.

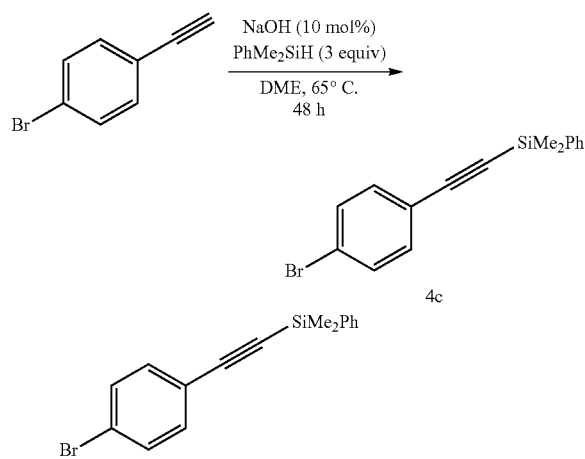

((4-Bromophenyl)ethynyl)dimethyl(phenyl)silane 4c

The general procedure was followed. The reaction was performed with NaOH (2.0 mg, 0.05 mmol, 10 mol %), 1-bromo-4-ethynylbenzene (90 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 4c (81.3 mg, 52% yield) was obtained in 80% purity after solvent removal at 85° C. at 45 mtorr for 30 minutes; subsequent purification by silica gel flash chromatography (100% hexanes) yielded the product 4c as colourless crystals in a 9:1 mixture with diphenyltetramethyldisiloxane. $R_f$=0.54 (100% hexanes); $^1$H NMR (500 MHz, THF-d8) δ 7.69-7.63 (m, 2H), 7.51 (d, J=8.5 Hz, 2H), 7.39 (d, J=8.5 Hz, 2H), 7.36-7.30 (m, 3H), 0.46 (s, 6H); $^{13}$C NMR (126 MHz, THF-d8) δ 137.55, 134.65, 134.53, 132.66, 130.44, 128.83, 123.94, 123.19, 106.51, 94.19, −0.66. IR (Neat Film NaCl) 3068, 2958, 2159, 1653, 1540, 1484, 1473, 1457, 1427, 1249, 1214, 1114, 1071, 1010, 846, 830, 780, 730, 698 cm$^{-1}$; HRMS (EI+) calc'd for $C_{16}H_{16}Si^{18}Br$ [M+H]: 317.0184. found 317.0180.

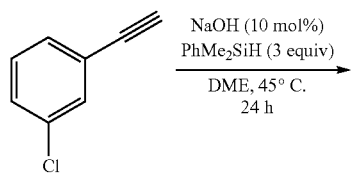

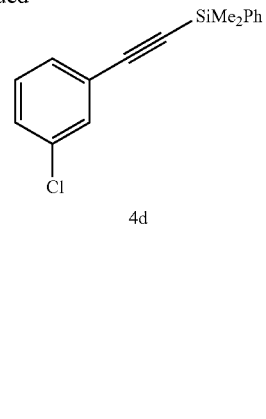

((3-Chlorophenyl)ethynyl)dimethyl(phenyl)silane 4d

The general procedure was followed. The reaction was performed with NaOH (2.0 mg, 0.05 mmol, 10 mol %), 1-chloro-3-ethynylbenzene (68 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 24 h. The desired product 4d (121.6 mg, 90% yield) was obtained in 95% purity after solvent removal at 85° C. at 45 mtorr for 30 minutes; subsequent purification by silica gel flash chromatography (100% hexanes) yielded the product 4d in analytically pure form as a colorless oil. $R_f$=0.42 (100% hexanes); $^1$H NMR (500 MHz, CDCl$_3$) δ 7.70-7.66 (m, 2H), 7.49 (ddd, J=2.1, 1.5, 0.5 Hz, 1H), 7.40 (dd, J=5.0, 1.9 Hz, 3H), 7.38 (dt, J=7.6, 1.4 Hz, 1H), 7.31 (ddd, J=8.1, 2.1, 1.2 Hz, 1H), 7.24 (ddd, J=8.0, 7.6, 0.5 Hz, 1H), 0.51 (s, 6H); $^{13}$C NMR (126 MHz, CDCl$_3$) δ 136.75, 134.21, 133.86, 132.05, 130.29, 129.70, 129.61, 129.12, 128.10, 124.77, 105.13, 93.82, −0.79. IR (Neat Film NaCl) 3420, 2163, 1684, 1647, 1559, 1521, 1507, 1457, 1249, 1117, 1091, 884, 781, 681 cm$^{-1}$; HRMS (EI+) calc'd for $C_{16}H_{16}ClSi$ [M+H]: 271.0710, found 271.0710.

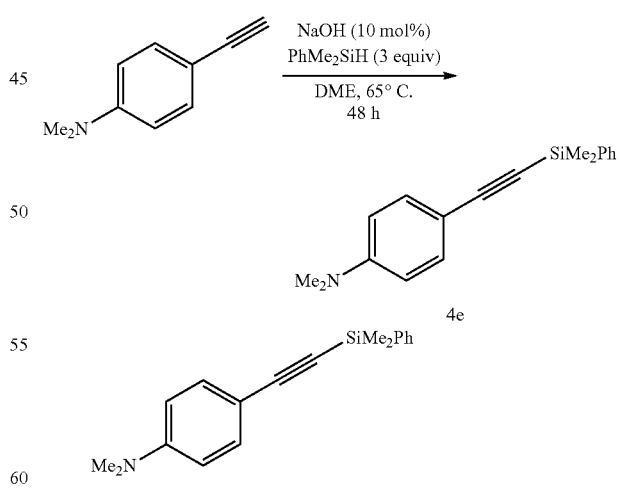

4-((Dimethyl(phenyl)silyl)ethynyl)-N,N-dimethylaniline 4e

The general procedure was followed. The reaction was performed with NaOH (2.0 mg, 0.05 mmol, 10 mol %), 4-ethynyl-N,N-dimethylaniline (73 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 65° C. for 48 h. The desired product 4e (139.4 mg, 100% yield) was obtained as colourless crystals after solvent removal at 85° C. at 45 mtorr for 30 minutes. $^1$H NMR (500 MHz, CDCl$_3$) δ 7.73-7.68 (m, 2H), 7.41-7.36 (m, 5H), 6.61 (d, J=8.9 Hz, 2H), 2.98 (s, 6H), 0.48 (s, 6H); $^{13}$C NMR (126 MHz, CDCl$_3$) δ 150.46, 137.88, 133.93, 133.38, 129.36, 127.94, 111.69, 109.78, 108.49, 89.19, 40.32, −0.39. IR (Neat Film NaCl) 3067, 2957, 2147, 1682, 1607, 1519, 1487, 1427, 1360, 1248, 1186, 1115, 945, 850, 817, 779, 730, 699, 653 cm$^{-1}$; HRMS (EI+) calc'd for C$_{18}$H$_{21}$NSi [M+•]: 279.1443, found 279.1445.

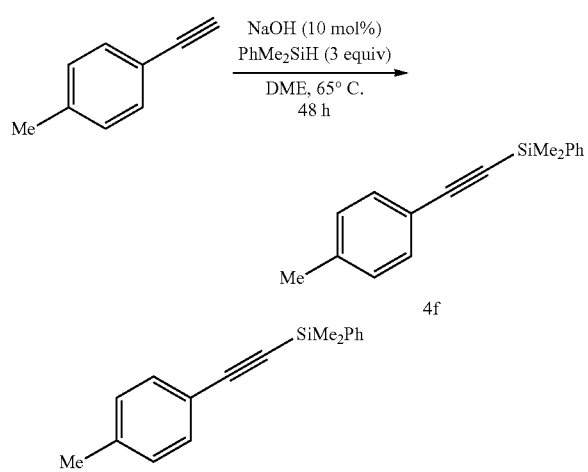

4f

Dimethyl(phenyl)(p-tolylethynyl)silane 4f

The general procedure was followed. The reaction was performed with NaOH (2.0 mg, 0.05 mmol, 10 mol %), 1-ethynyl-4-methylbenzene (58 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 65° C. for 48 h. The desired product 4f (115.5 mg, 92% yield) was obtained as a pale yellow oil after solvent removal at 85° C. at 45 mtorr for 30 minutes. $^1$H NMR (500 MHz, CDCl$_3$) δ 7.71 (ddt, J=6.0, 2.4, 1.1 Hz, 2H), 7.41 (ddq, J=5.8, 3.0, 0.9 Hz, 5H), 7.16-7.10 (m, 2H), 2.37 (s, 3H), 0.51 (d, J=1.1 Hz, 6H); $^{13}$C NMR (126 MHz, CDCl$_3$) δ 139.02, 137.33, 133.90, 132.10, 129.52, 129.12, 128.02, 120.00, 107.18, 91.28, 21.69, −0.59. IR (Neat Film NaCl) 3420, 3068, 3049, 2959, 2920, 2156, 1507, 1428, 1408, 1249, 1223, 1117, 1020, 851, 816, 780, 731, 700, 656 cm$^{-1}$; HRMS (EI+) calc'd for C$_{17}$H$_{19}$Si [M+H]: 251.1256, found 251.1257.

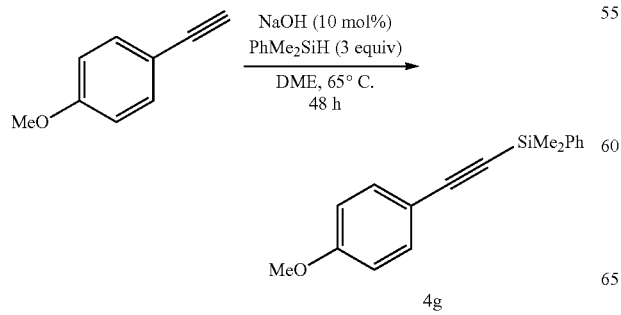

4g

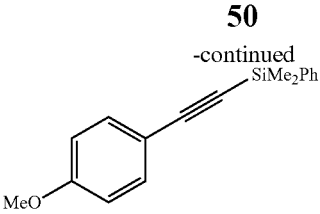

((4-Methoxyphenyl)ethynyl)dimethyl(phenyl)silane 4g

The general procedure was followed. The reaction was performed with NaOH (2.0 mg, 0.05 mmol, 10 mol %), 1-ethynyl-4-methoxybenzene (66 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 65° C. for 48 h. The desired product 4g (121.6 mg, 91% yield) was obtained in 95% purity after solvent removal at 85° C. at 45 mtorr for 30 minutes; subsequent purification by silica gel flash chromatography (100% hexanes→5% EtOAc in hexanes) yielded the product 4g in analytically pure form as a yellow oil. R$_f$=0.27 (100% hexanes); $^1$H NMR (500 MHz, CDCl$_3$) δ 7.71 (dd, J=6.5, 3.0 Hz, 2H), 7.46 (d, J=8.9 Hz, 2H), 7.43-7.38 (m, 3H), 6.84 (d, J=8.9 Hz, 2H), 3.82 (s, 3H), 0.51 (s, 6H); $^{13}$C NMR (126 MHz, CDCl$_3$) δ 160.02, 137.42, 133.89, 133.73, 129.50, 128.01, 115.20, 113.96, 107.03, 90.47, 55.42, −0.56. IR (Neat Film NaCl) 3068, 2959, 2154, 1605, 1507, 1441, 1293, 1249, 1171, 1116, 1032, 853, 832, 812, 779, 755, 731, 699 cm$^{-1}$; HRMS (EI+) calc'd for C$_{17}$H$_{18}$OSi [M+•]: 266.1127, found 266.1135.

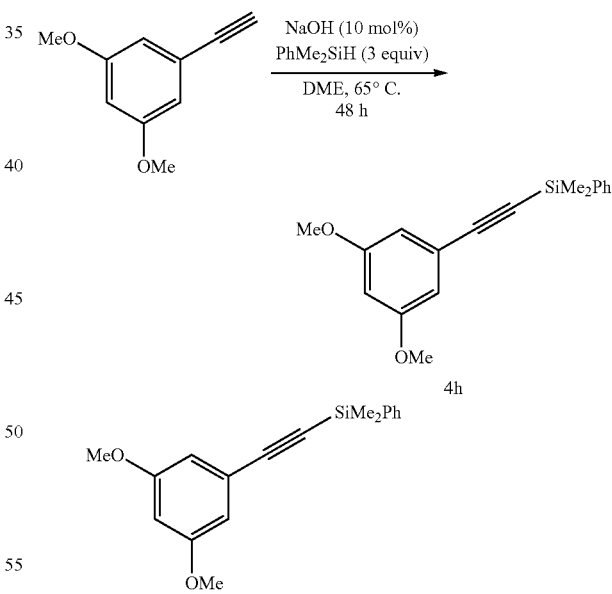

4h ((3,5-Dimethoxyphenyl)ethynyl)dimethyl(phenyl) silane 4h

The general procedure was followed. The reaction was performed with NaOH (2.0 mg, 0.05 mmol, 10 mol %), 1-ethynyl-3,5-dimethoxybenzene (81 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 65° C. for 48 h. The desired product 4h (140.6 mg, 95% yield) was obtained as a light yellow oil after solvent removal at 85° C. at 45 mtorr for 30 minutes. $^1$H NMR (500 MHz, CDCl$_3$) δ 7.70 (ddd, J=5.5, 2.7, 1.2 Hz, 2H), 7.41 (dd, J=4.6, 2.1 Hz, 3H), 6.67 (d, J=2.3 Hz, 2H), 6.47 (t, J=2.3 Hz, 1H), 3.79 (s, 6H), 0.52 (d, J=1.5 Hz, 6H); $^{13}$C NMR (126 MHz, CDCl$_3$) δ 160.56, 137.05, 133.90, 129.61, 128.05, 124.29, 109.87, 106.78, 102.53, 91.75, 55.57, −0.68. IR (Neat Film NaCl) 3421, 3069, 3001, 2959, 2837, 2160, 1596, 1456, 1419, 1348, 1298, 1250, 1205, 1155, 1116, 1064, 979, 964, 817, 753, 732, 681 cm$^{-1}$; HRMS (EI+) calc'd for C$_{18}$H$_{21}$O$_2$Si [M+H]: 297.1311, found 297.1309.

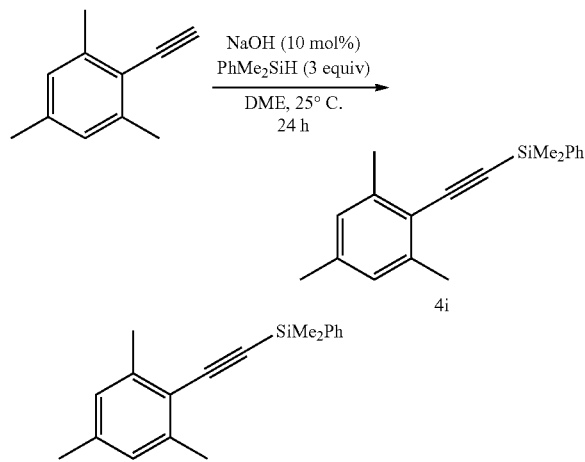

2-Ethynyl-1,3,5-trimethylbenzene 4i

The general procedure was followed. The reaction was performed with NaOH (2.0 mg, 0.05 mmol, 10 mol %), 2-ethynyl-1,3,5-trimethylbenzene (57 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 25° C. for 24 h. The desired product 4i (119.1 mg, 86% yield) was obtained as a colorless oil after solvent removal at 85° C. at 45 mtorr for 30 minutes. $^1$H NMR (500 MHz, CDCl$_3$) δ 7.73 (ddt, J=4.5, 3.2, 0.8 Hz, 3H), 7.40 (dd, J=2.5, 0.8 Hz, 2H), 6.88-6.86 (m, 2H), 2.42 (s, 6H), 2.29 (s, 3H), 0.52 (t, J=0.7 Hz, 6H); $^{13}$C NMR (126 MHz, CDCl$_3$) δ 140.86, 138.23, 137.66, 133.89, 129.45, 127.99, 127.67, 119.94, 104.95, 99.66, 21.51, 21.15, −0.34. IR (Neat Film NaCl) 3440, 3068, 2959, 2146, 1646, 1610, 1474, 1428, 1224, 1117, 841, 825, 779, 753, 698 cm$^{-1}$; HRMS (EI+) calc'd for C$_{19}$H$_{23}$Si [M+H]: 279.1569, found 279.1561.

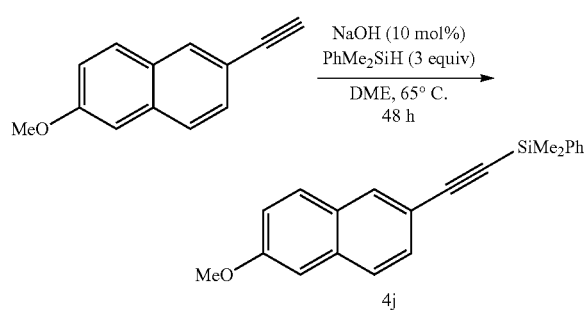

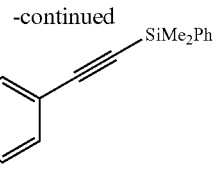

((6-Methoxynaphthalen-2-yl)ethynyl)dimethyl(phenyl)silane 4j

The general procedure was followed. The reaction was performed with NaOH (2.0 mg, 0.05 mmol, 10 mol %), 2-ethynyl-6-methoxynaphthalene (91 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 4j (134.8 mg, 85% yield) was obtained in 95% purity as a colorless oil after solvent removal at 85° C. at 45 mtorr for 30 minutes. This product decomposes on silica. $^1$H NMR (500 MHz, CDCl$_3$) δ 7.99 (dd, J=1.5, 0.7 Hz, 1H), 7.78-7.72 (m, 2H), 7.70 (d, J=9.0 Hz, 1H), 7.68 (d, J=8.2 Hz, 1H), 7.53 (dd, J=8.4, 1.6 Hz, 1H), 7.46-7.40 (m, 3H), 7.17 (dd, J=8.9, 2.5 Hz, 1H), 7.11 (d, J=2.6 Hz, 1H), 3.93 (s, 3H), 0.56 (s, 6H); $^{13}$C NMR (126 MHz, CDCl$_3$) δ 158.57, 137.30, 134.48, 133.93, 132.17, 129.56, 129.34, 128.44, 128.05, 126.85, 122.76, 119.59, 117.93, 107.50, 105.91, 91.68, 55.50, −0.57. IR (Neat Film NaCl) 3422, 2959, 2152, 1631, 1601, 1499, 1481, 1461, 1390, 1267, 1232, 1161, 1117, 1031, 937, 890, 814, 780, 731, 703, 656 cm$^{-1}$; HRMS (EI+) calc'd for C$_{21}$H$_{20}$OSi [M+•]: 316.1284, found 316.1296.

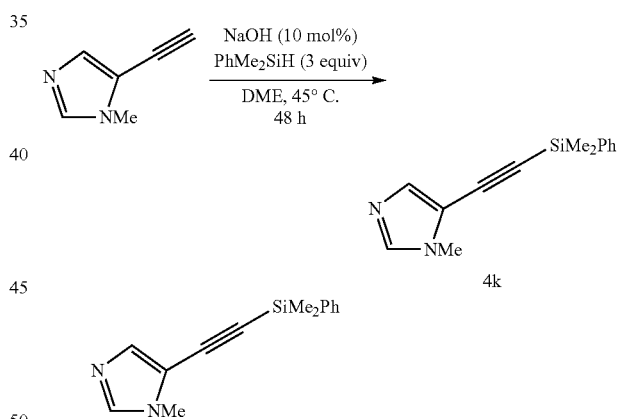

5-((Dimethyl(phenyl)silyl)ethynyl)-1-methyl-1H-imidazole 4k

The general procedure was followed. The reaction was performed with NaOH (2.0 mg, 0.05 mmol, 10 mol %), 5-ethynyl-1-methyl-1H-imidazole (53 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4k (98.7 mg, 82% yield) was obtained in 95% purity after solvent removal at 85° C. at 45 mtorr for 30 minutes; subsequent purification by silica gel flash chromatography (100% EtOAc) yielded the product 4k in analytically pure form as a colorless oil. R$_f$=0.45 (100% EtOAc); $^1$H NMR (500 MHz, CDCl$_3$) δ 7.68-7.65 (m, 2H), 7.40 (m, 4H), 7.31 (d, J=1.0 Hz, 1H), 3.68-3.65 (m, 3H), 0.52 (s, 6H); $^{13}$C NMR (126 MHz, CDCl$_3$) δ 138.37, 136.49, 135.29, 133.74, 129.73, 128.09, 116.28, 100.60, 94.11, 32.11, −0.85. IR (Neat Film NaCl) 3417, 2960, 2157, 1646, 1533, 1489, 1428, 1274, 1250, 1227, 1116, 924, 823, 782, 732, 702, 661 cm$^{-1}$; HRMS (EI+) calc'd for C$_{14}$H$_{17}$N$_2$Si [M+H]: 241.1161, found 241.1169.

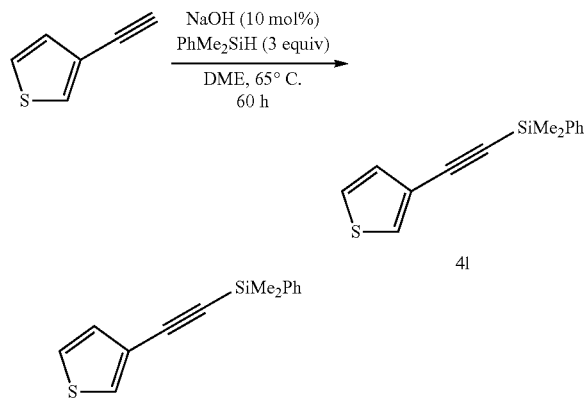

Dimethyl(phenyl)(thiophen-3-ylethynyl)silane 4l

The general procedure was followed. The reaction was performed with NaOH (2.0 mg, 0.05 mmol, 10 mol %), 3-ethynylthiophene (54 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 60 h. The desired product 4l (113.2 mg, 93% yield) was obtained in 95% purity after solvent removal at 85° C. at 45 mtorr for 30 minutes; subsequent purification by silica gel flash chromatography (100% hexanes) yielded the product 4l in analytically pure form as a colorless oil. R$_f$=0.39 (100% hexanes); $^1$H NMR (500 MHz, CDCl$_3$) δ 7.72-7.68 (m, 2H), 7.53 (dd, J=3.0, 1.2 Hz, 1H), 7.43-7.39 (m, 3H), 7.27-7.24 (m, 1H), 7.17 (dd, J=5.0, 1.2 Hz, 1H), 0.51 (s, 6H); $^{13}$C NMR (126 MHz, CDCl$_3$) δ 137.08, 133.88, 130.26, 130.11, 129.59, 128.04, 125.36, 122.32, 101.67, 91.93, −0.68. IR (Neat Film NaCl) 3107, 3068, 2959, 2152, 1427, 1356, 1249, 1163, 1116, 944, 870, 781, 753, 698 cm$^{-1}$; HRMS (EI+) calc'd for C$_{14}$H$_{14}$SSi [M+•]: 242.0586, found 242.0576.

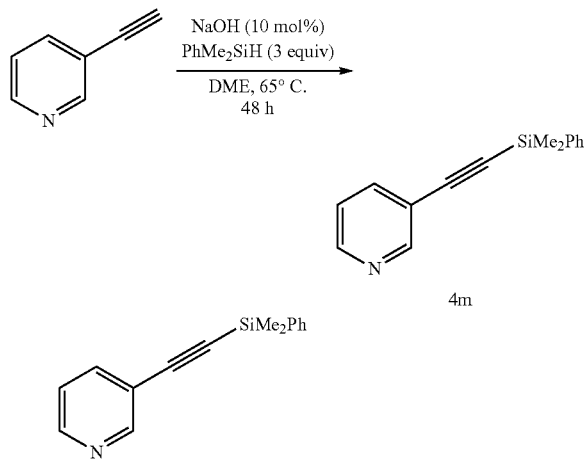

3-((Dimethyl(phenyl)silyl)ethynyl)pyridine 4m

The general procedure was followed. The reaction was performed with NaOH (2.0 mg, 0.05 mmol, 10 mol %), 3-ethynylpyridine (52 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 4m (91.8 mg, 77% yield) was obtained in 95% purity after solvent removal at 85° C. at 45 mtorr for 30 minutes; subsequent purification by silica gel flash chromatography (100% hexanes) yielded the product 4m in analytically pure form as a colorless oil. R$_f$=0.31 (100% hexanes); $^1$H NMR (500 MHz, CDCl$_3$) δ 8.74 (dd, J=2.1, 0.9 Hz, 1H), 8.54 (dd, J=4.9, 1.7 Hz, 1H), 7.77 (ddd, J=7.9, 2.1, 1.7 Hz, 1H), 7.71-7.67 (m, 2H), 7.42 (dd, J=4.9, 1.9 Hz, 3H), 7.24 (ddd, J=7.9, 4.9, 0.9 Hz, 1H), 0.54 (s, 6H); $^{13}$C NMR (126 MHz, CDCl$_3$) δ 152.82, 149.02, 139.01, 136.49, 133.81, 129.74, 128.11, 123.00, 120.21, 103.14, 96.34, −0.88. IR (Neat Film NaCl) 3420, 3069, 3048, 3025, 2960, 2161, 1559, 1474, 1406, 1250, 1184, 1119, 1022, 847, 781, 754, 703, 670 cm$^{-1}$; HRMS (EI+) calc'd for C$_{15}$H$_{16}$NSi [M+H]: 238.1052, found 238.1049.

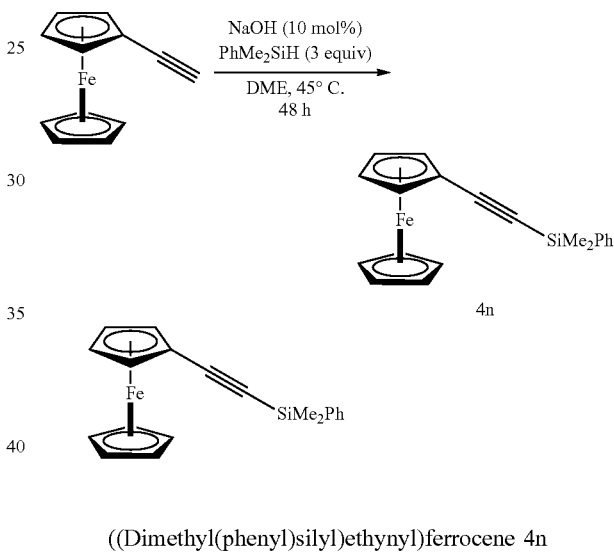

((Dimethyl(phenyl)silyl)ethynyl)ferrocene 4n

The general procedure was followed. The reaction was performed with NaOH (2.0 mg, 0.05 mmol, 10 mol %), ethynylferrocene (105 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4n (170.1 mg, 99% yield) was obtained as a red crystalline solid after solvent removal at 85° C. at 45 mtorr for 30 minutes. $^1$H NMR (500 MHz, CDCl$_3$) δ 7.70 (dd, J=6.1, 3.1 Hz, 2H), 7.43-7.37 (m, 3H), 4.48 (s, 2H), 4.21 (m, 7H), 0.47 (s, 6H); $^{13}$C NMR (126 MHz, CDCl$_3$) δ 137.71, 133.89, 129.44, 127.98, 106.30, 88.52, 72.02, 70.26, 69.00, 64.64, −0.40. IR (Neat Film NaCl) 2958, 2147, 1428, 1248, 1106, 1024, 1001, 925, 819, 779, 753, 730, 699 cm$^{-1}$; HRMS (EI+) calc'd for C$_{20}$H$_{20}$FeSi [M+•]: 344.0684, found 344.0696.

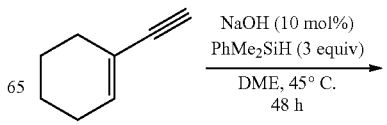

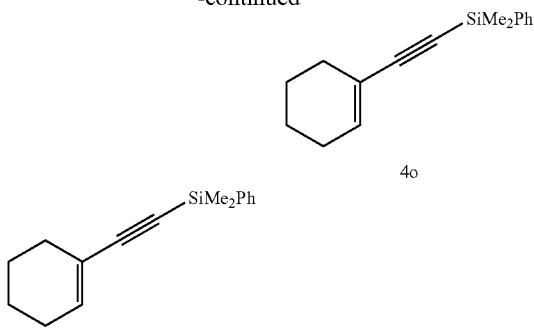

(Cyclohex-1-en-1-ylethynyl)dimethyl(phenyl)silane
4o

The general procedure was followed. The reaction was performed with NaOH (2.0 mg, 0.05 mmol, 10 mol %), 1-ethynylcyclohex-1-ene (53 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4o (102.7 mg, 85% yield) was obtained in 95% purity after solvent removal at 85° C. at 45 mtorr for 15 minutes; subsequent purification by silica gel flash chromatography (100% hexanes) yielded the product 4o in analytically pure form as a colorless oil. R$_f$=0.50 (100% hexanes); $^1$H NMR (500 MHz, CDCl$_3$) δ 7.67-7.63 (m, 2H), 7.39-7.36 (m, 3H), 6.24 (tt, J=3.9, 1.8 Hz, 1H), 2.17 (tdd, J=6.0, 2.7, 1.8 Hz, 2H), 2.11 (tdd, J=6.4, 4.6, 2.5 Hz, 2H), 1.68-1.55 (m, 4H), 0.43 (s, 6H); $^{13}$C NMR (126 MHz, CDCl$_3$) δ 137.59, 136.90, 133.84, 129.40, 127.94, 120.82, 109.17, 88.79, 29.14, 25.81, 22.33, 21.54, −0.51. IR (Neat Film NaCl) 3422, 2937, 2145, 1647, 1428, 1249, 1116, 863, 819, 779, 730, 698 cm$^{-1}$; HRMS (EI+) calc'd for C$_{16}$H$_{21}$Si [M+H]: 241.1413. found 241.1402.

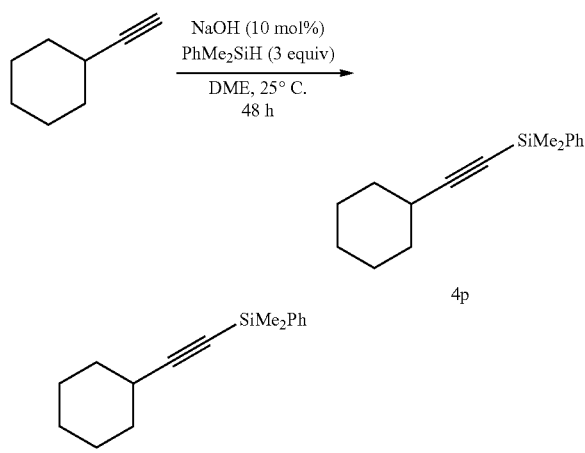

(Cyclohexylethynyl)dimethyl(phenyl)silane 4p

The general procedure was followed. The reaction was performed with NaOH (2.0 mg, 0.05 mmol, 10 mol %), ethynylcyclohexane (54 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 25° C. for 48 h. The desired product 4p (97.4 mg, 80% yield) was obtained in 80% purity after solvent removal at 85° C. at 45 mtorr for 15 minutes; subsequent purification by silica gel flash chromatography (100% hexanes) yielded the product 4p as a colorless oil in a 9:1 mixture with diphenyltetramethyldisiloxane. R$_f$=0.53 (100% hexanes); $^1$H NMR (500 MHz, CDCl$_3$) δ 7.65 (ddd, J=5.4, 2.4, 1.7 Hz, 2H), 7.37 (ddq, J=4.0, 1.9, 0.8 Hz, 3H), 2.47 (tt, J=9.0, 3.8 Hz, 1H), 1.89-1.79 (m, 2H), 1.73 (ddd, J=9.8, 6.2, 3.1 Hz, 2H), 1.52 (td, J=9.7, 9.2, 3.8 Hz, 3H), 1.38-1.26 (m, 3H), 0.40 (d, J=1.0 Hz, 6H); $^{13}$C NMR (126 MHz, CDCl$_3$) δ 133.82, 133.13, 129.29, 127.89, 113.93, 81.74, 32.70, 30.23, 26.00, 24.93, −0.30. IR (Neat Film NaCl) 2931, 2854, 2173, 1448, 1427, 1248, 1116, 1076, 843, 834, 816, 779, 729, 698 cm$^{-1}$; HRMS (EI+) calc'd for C$_{16}$H$_{21}$Si [(M+H)—H$_2$]: 241.1413, found 241.1419.

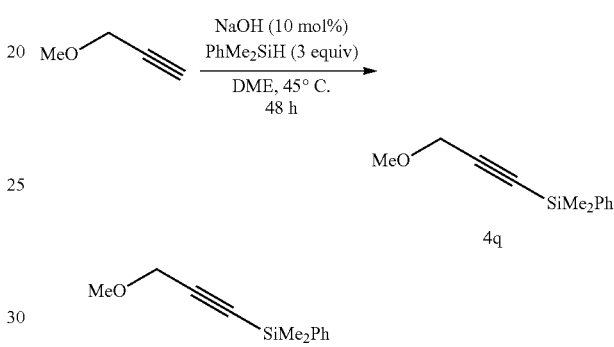

(3-Methoxyprop-1-yn-1-yl)dimethyl(phenyl)silane
4q

The general procedure was followed. The reaction was performed with NaOH (2.0 mg, 0.05 mmol, 10 mol %), 3-methoxyprop-1-yne (35 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4q (61.0 mg, 60% yield) was obtained in 95% purity after solvent removal at 85° C. at 45 mtorr for 15 minutes; careful heating is necessary, as the product is volatile under these conditions. Subsequent purification by silica gel flash chromatography (1:1 DCM:hexanes) yielded the product 4q in analytically pure form as a colorless oil. R$_f$=0.38 (1:1 DCM:hexanes); $^1$H NMR (500 MHz, CDCl$_3$) δ 7.65-7.62 (m, 2H), 7.41-7.36 (m, 3H), 4.16 (s, 2H), 3.41 (s, 3H), 0.45 (s, 6H); $^{13}$C NMR (126 MHz, CDCl$_3$) δ 136.63, 133.66, 129.49, 127.90, 103.05, 89.53, 60.48, 57.67, −0.97. IR (Neat Film NaCl) 3423, 2925, 2173, 1640, 1428, 1353, 1250, 1186, 1103, 1007, 990, 903, 838, 817, 781, 731, 698 cm$^{-1}$; HRMS (EI+) calc'd for C$_{12}$H$_{16}$OSi [M+•]: 204.0971, found 204.0977.

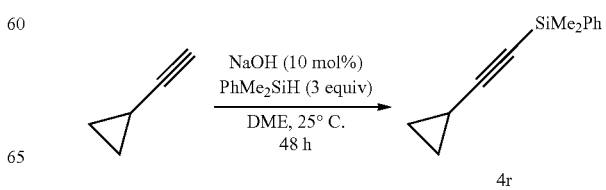

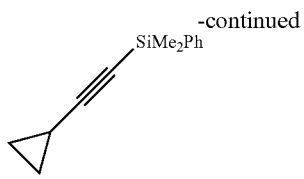

(Cyclopropylethynyl)dimethyl(phenyl)silane 4r

The general procedure was followed. The reaction was performed with NaOH (2.0 mg, 0.05 mmol, 10 mol %), ethynylcyclopropane (33 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 25° C. for 48 h. The desired product 4r (70.1 mg, 70% yield) was obtained in 95% purity after solvent removal at 85° C. at 45 mtorr for 30 minutes; careful heating is necessary, as this product is volatile under these conditions. Subsequent purification by silica gel flash chromatography (100% hexanes) yielded the product 4r in analytically pure form as a colorless oil. R$_f$=0.38 (100% hexanes); $^1$H NMR (500 MHz, CDCl$_3$) δ 7.64-7.61 (m, 2H), 7.39-7.36 (m, 3H), 1.40-1.30 (m, 1H), 0.87-0.75 (m, 4H), 0.40 (s, 6H); $^{13}$C NMR (126 MHz, CDCl$_3$) δ 137.77, 133.79, 129.36, 127.92, 112.40, 77.65, 8.97, 0.70, −0.45. IR (Neat Film NaCl) 3423, 3068, 2960, 2172, 2158, 1646, 1428, 1348, 1249, 1114, 1028, 839, 779, 730, 659 cm$^{-1}$; HRMS (EI+) calc'd for C$_{13}$H$_{16}$Si [M+•]: 200.1021, found 200.1031.

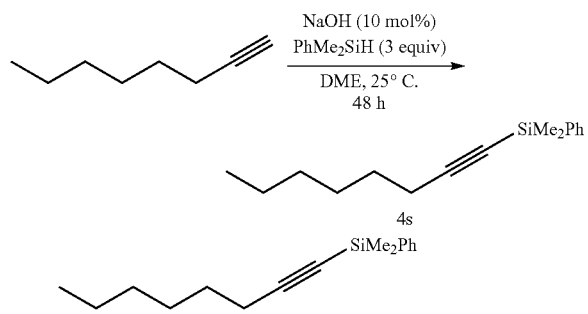

Dimethyl(oct-1-yn-1-yl)(phenyl)silane 4s

The general procedure was followed.
The reaction was performed with NaOH (2.0 mg, 0.05 mmol, 10 mol %), oct-1-yne (55 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 25° C. for 48 h. The desired product 4s (101.0 mg, 83% yield) was obtained in 95% purity after solvent removal at 85° C. at 45 mtorr for 15 minutes; subsequent purification by silica gel flash chromatography (100% hexanes) yielded the product 4s in analytically pure form as a colorless oil. R$_f$=0.53 (100% hexanes); $^1$H NMR (500 MHz, CDCl$_3$) δ 7.67-7.62 (m, 2H), 7.40-7.35 (m, 3H), 2.28 (t, J=7.1 Hz, 2H), 1.59-1.53 (m, 2H), 1.47-1.39 (m, 2H), 1.35-1.27 (m, 4H), 0.91 (t, J=6.9 Hz, 3H), 0.40 (s, 6H); $^{13}$C NMR (126 MHz, CDCl$_3$) δ 137.86, 133.80, 129.35, 127.92, 109.85, 82.31, 31.43, 28.68, 28.64, 22.69, 20.12, 14.19, −0.44. IR (Neat Film NaCl) 3422, 3069, 2957, 2931, 2858, 2174, 1647, 1428, 1248, 1115, 836, 815, 779, 729, 699 cm$^{-1}$; HRMS (EI+) calc'd for C$_{16}$H$_{23}$Si [M+H]: 245.1726, found 245.1727.

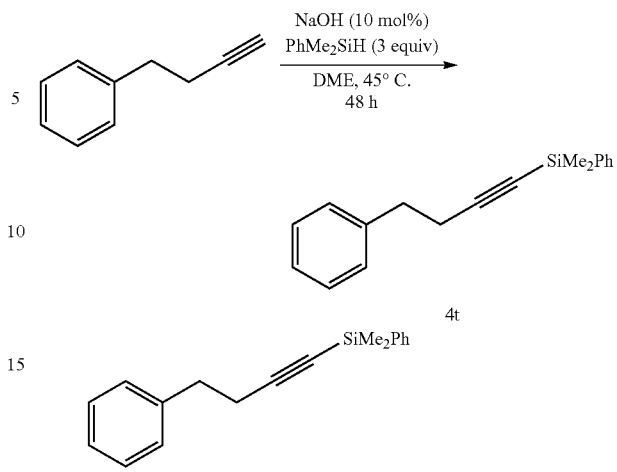

Dimethyl(phenyl)(4-phenylbut-1-yn-1-yl)silane 4t

The general procedure was followed. The reaction was performed with NaOH (2.0 mg, 0.05 mmol, 10 mol %), but-3-yn-1-ylbenzene (65 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4t (130.0 mg, 98% yield) was obtained as a pale yellow oil after solvent removal at 85° C. at 45 mtorr for 30 minutes. $^1$H NMR (500 MHz, CDCl$_3$) δ 7.64-7.59 (m, 2H), 7.42-7.37 (m, 3H), 7.31 (dd, J=8.0, 6.8 Hz, 2H), 7.28-7.23 (m, 3H), 2.90 (t, J=7.5 Hz, 2H), 2.60 (t, J=7.5 Hz, 2H), 0.42 (d, J=0.6 Hz, 6H); $^{13}$C NMR (126 MHz, CDCl$_3$) δ 140.63, 137.56, 133.80, 129.39, 128.68, 128.47, 127.93, 126.43, 108.62, 83.39, 35.10, 22.38, −0.56. IR (Neat Film NaCl) 3423, 3086, 3067, 3027, 2959, 2174, 1647, 1602, 1495, 1453, 1427, 1248, 1114, 1077, 1042, 869, 811, 779, 729, 696, 661 cm$^{-1}$; HRMS (EI+) calc'd for C$_{18}$H$_{19}$Si [(M+H)—H$_2$]: 263.1256, found 263.1258.

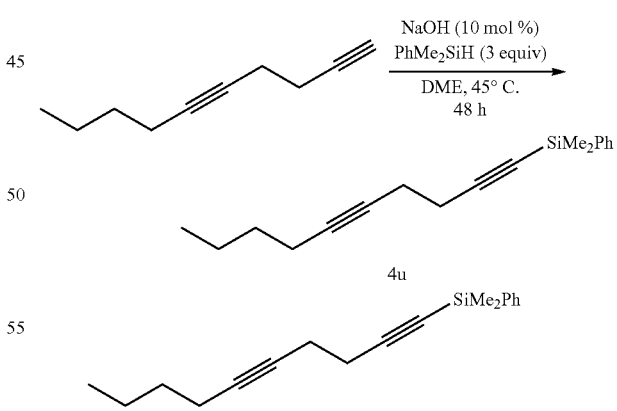

Deca-1,5-diyn-1-yldimethyl(phenyl)silane 4u

The general procedure was followed. The reaction was performed with NaOH (2.0 mg, 0.05 mmol, 10 mol %), deca-1,5-diyne (67 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4u (131.3 mg, 98% yield) was obtained as a colorless oil after solvent removal at 85° C. at 45 mtorr for 30 minutes. $^1$H NMR (500 MHz, CDCl$_3$) δ 7.68-7.64 (m, 2H), 7.38 (dd, J=5.0, 1.9 Hz, 3H), 2.49 (ddd, J=7.7, 6.1, 1.7 Hz, 2H), 2.46-2.39 (m, 2H), 2.18 (tt, J=7.0, 2.3 Hz, 2H), 1.52-1.39 (m, 4H), 0.92 (t, J=7.2 Hz, 3H), 0.42 (s, 6H); $^{13}$C NMR (126 MHz, CDCl$_3$) δ 137.56, 133.81, 129.40, 127.92, 107.79, 83.33, 81.59, 78.33, 31.20, 22.05, 20.79, 19.16, 18.54, 13.77, −0.54. IR (Neat Film NaCl) 2958, 2932, 2872, 2177, 1465, 1428, 1336, 1249, 1115, 1042, 870, 837, 816, 780, 754, 731, 700, 662 cm$^{-1}$; HRMS (EI+) calc'd for C$_{18}$H$_{23}$Si [(M+H)—H$_2$]: 267.1569, found 267.1565.

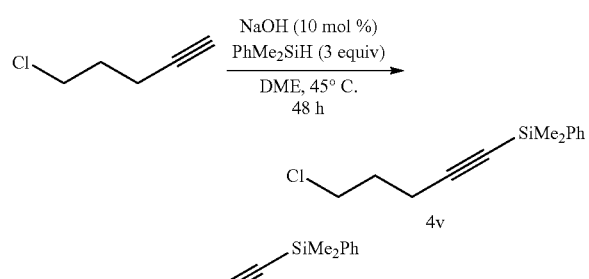

(5-Chloropent-1-yn-1-yl)dimethyl(phenyl)silane 4v

The general procedure was followed. The reaction was performed with NaOH (2.0 mg, 0.05 mmol, 10 mol %), 5-chloropent-1-yne (51 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4v (93.3 mg, 79% yield) was obtained in 95% purity after solvent removal at 85° C. at 45 mtorr for 30 minutes; careful heating is necessary, as this product is volatile under these conditions. Subsequent purification by silica gel flash chromatography (100% hexanes) yielded the product 4v in analytically pure form as a colorless oil. R$_f$=0.31 (100% hexanes); $^1$H NMR (500 MHz, CDCl$_3$) δ 7.65-7.60 (m, 2H), 7.38 (dd, J=4.9, 1.9 Hz, 3H), 3.67 (t, J=6.4 Hz, 2H), 2.49 (t, J=6.8 Hz, 2H), 2.01 (p, J=6.6 Hz, 2H), 0.41 (s, 6H); $^{13}$C NMR (126 MHz, CDCl$_3$) δ 137.46, 133.75, 129.48, 127.99, 107.20, 83.81, 43.77, 31.40, 17.57, −0.56. IR (Neat Film NaCl) 3420, 3069, 2960, 2928, 2174, 1646, 1428, 1249, 1114, 1041, 837, 816, 780, 731, 701, 665 cm$^{-1}$; HRMS (EI+) calc'd for C$_{13}$H$_{16}$ClSi [(M+H)—H$_2$]: 235.0710, found 235.0713.

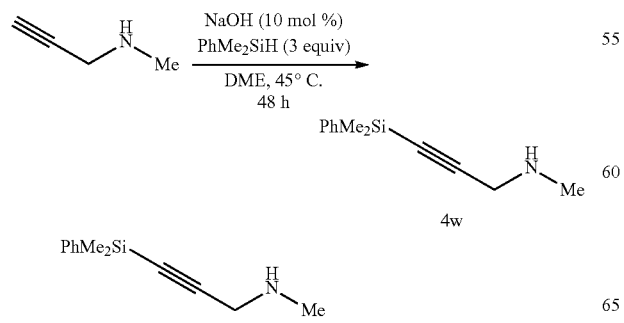

3-(Dimethyl(phenyl)silyl)-N-methylprop-2-yn-1-amine 4w

The general procedure was followed. The reaction was performed with NaOH (2.0 mg, 0.05 mmol, 10 mol %), N-methylprop-2-yn-1-amine (69 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 48 h. The desired product 4w (81.8 mg, 80% yield) was obtained in 95% purity after solvent removal at 85° C. at 45 mtorr for 15 minutes; careful heating is necessary, as the product is volatile under these conditions. Subsequent purification by silica gel flash chromatography (100% EtOAc) yielded the product 4w in analytically pure form as a colorless oil. R$_f$=0.32 (100% EtOAc); $^1$H NMR (500 MHz, THF-d8) δ 7.63-7.59 (m, 2H), 7.33-7.29 (m, 3H), 3.36 (s, 2H), 2.39 (s, 3H), 0.36 (s, 6H); $^{13}$C NMR (126 MHz, THF-d8) δ 138.26, 134.58, 130.18, 128.67, 108.45, 85.45, 41.75, 35.64, −0.33. IR (Neat Film NaCl) 3416, 3068, 2957, 2165, 1725, 1651, 1427, 1250, 1116, 1044, 836, 817, 730, 699 cm$^{-1}$; HRMS (EI+) calc'd for C$_{12}$H$_{18}$NSi [M+H]: 204.1208, found 204.1214.

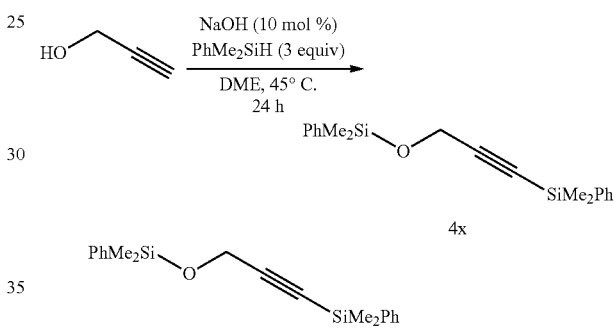

(3-((Dimethyl(phenyl)silyl)oxy)prop-1-yn-1-yl)dimethyl(phenyl)silane 4x

The general procedure was followed. The reaction was performed with NaOH (2.0 mg, 0.05 mmol, 10 mol %), prop-2-yn-1-ol (28 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 24 h. The desired product 4x (142.9 mg, 88% yield) was obtained as a colorless oil after solvent removal at 85° C. at 45 mtorr for 30 minutes. Careful heating is necessary, as the product is volatile under these conditions. $^1$H NMR (500 MHz, CDCl$_3$) δ 7.62 (ddt, J=6.4, 1.8, 0.9 Hz, 4H), 7.44-7.36 (m, 6H), 4.35 (s, 2H), 0.48 (s, 6H), 0.43 (s, 6H); $^{13}$C NMR (126 MHz, CDCl$_3$) δ 137.08, 136.80, 133.82, 133.73, 129.93, 129.57, 128.01, 127.98, 105.77, 88.23, 52.27, −0.93, −1.36. IR (Neat Film NaCl) 3069, 3049, 2959, 2177, 1428, 1363, 1250, 1117, 1085, 1043, 1004, 817, 782, 731, 698 cm$^{-1}$; HRMS (EI+) calc'd for C$_{19}$H$_{23}$OSi$_2$ [(M+H)—H$_2$]: 323.1288, found 323.1297.

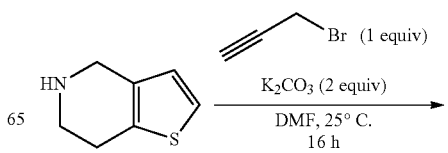

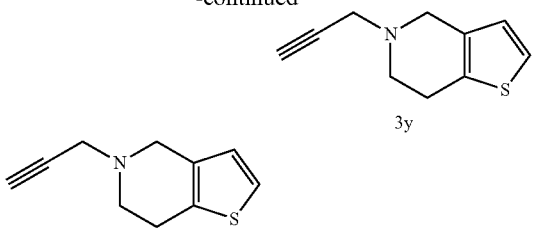

5-(Prop-2-yn-1-yl)-4,5,6,7-tetrahydrothieno[3,2-c]pyridine 3y

To a mixture of tetrahydrothieno[3,2-c]pyridine hydrochloride (1.40 g, 10 mmol, 1 equiv) and $K_2CO_3$ (2.76 g, 20 mmol, 2 equiv) in DMF (30 ml), was added 1-propyne-3-bromide (1.18 g, 10 mmol, 1 equiv) and the mixture was stirred at room temperature for 16 h. The mixture was filtered and solvent was removed under reduced pressure to give a brown oil. This oil was diluted with 20 mL of diethyl ether and washed with 20 mL of water, then 20 mL brine, then dried over anhydrous $Na_2SO_4$. The solvent was removed in vacuo and the residue was purified by column chromatography on silica gel (10:1 hexanes:$Et_2O$) yielding the product 3y as a yellow liquid (1.27 g, 72% yield). $R_f$=0.35 (10% EtOAc in hexanes); $^1H$ NMR (500 MHz, $CDCl_3$) δ 7.08 (dt, J=5.1, 0.7 Hz, 1H), 6.73 (d, J=5.1 Hz, 1H), 3.69 (t, J=1.7 Hz, 2H), 3.53 (d, J=2.4 Hz, 2H), 2.95-2.91 (m, 2H), 2.91-2.88 (m, 2H), 2.29 (t, J=2.4 Hz, 1H); $^{13}C$ NMR (126 MHz, $CDCl_3$) δ 133.55, 132.89, 125.19, 122.83, 78.78, 73.39, 51.50, 49.70, 46.37, 25.57. IR (Neat Film NaCl) 3937, 3626, 3390, 3289, 3103, 3065, 2910, 2816, 2101, 2651, 1614, 1565, 1461, 1428, 1405, 1328, 1275, 1219, 1191, 1166, 1130, 1109, 1079, 1051, 1017, 983, 902, 835, 789, 703 $cm^{-1}$; HRMS (EI+) calc'd for $C_{10}H_{12}NS$ [M+H]: 178.0690, found 178.0689.

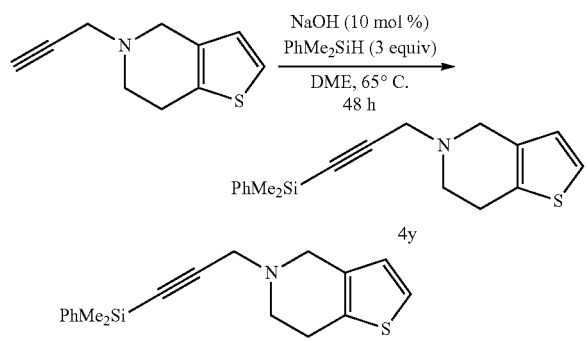

5-(3-(Dimethyl(phenyl)silyl)prop-2-yn-1-yl)-4,5,6,7-tetrahydrothieno[3,2-c]pyridine 4y The general procedure was followed. The reaction was performed with NaOH (2.0 mg, 0.05 mmol, 10 mol %), 5-(prop-2-yn-1-yl)-4,5,6,7-tetrahydrothieno[3,2-c]pyridine (89 mg, 0.5 mmol, 1.0 equiv), $PhMe_2SiH$ (204 mg, 230 µL, 1.5 mmol, 3.0 equiv), and 0.5 mL of 1,2-dimethoxyethane (DME) at 65° C. for 48 h. The desired product 4y (120.4 mg, 77% yield) was obtained in 95% purity after solvent removal at 85° C. at 45 mtorr for 15 minutes; subsequent purification by silica gel flash chromatography (10% EtOAc in hexanes) yielded the product 4y in analytically pure form as a yellow oil. $R_f$=0.40 (10% EtOAc in hexanes); $^1H$ NMR (500 MHz, $CDCl_3$) δ 7.67-7.61 (m, 2H), 7.43-7.34 (m, 3H), 7.09 (dd, J=5.1, 0.8 Hz, 1H), 6.75 (d, J=5.1 Hz, 1H), 3.72 (t, J=1.6 Hz, 2H), 3.61 (d, J=0.7 Hz, 2H), 2.99-2.88 (m, 4H), 0.43 (s, 6H); $^{13}C$ NMR (126 MHz, $CDCl_3$) δ 137.12, 133.78, 133.16, 133.06, 129.54, 128.00, 125.36, 122.92, 102.74, 88.35, 51.69, 49.89, 47.60, 25.69, −0.60. IR (Neat Film NaCl) 3067, 2957, 2906, 2814, 2163, 1427, 1327, 1249, 1166, 1115, 1034, 1016, 975, 836, 817, 780, 731, 699 $cm^{-1}$; HRMS (EI+) calc'd for $C_{18}H_{20}NSSi$ [(M+H)—$H_2$]: 310.1086, found 310.1087.

Example 3.2

Procedure for the Multi-Gram Scale Synthesis of 4s

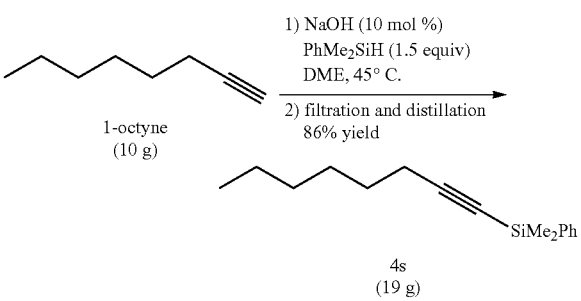

Dimethyl(oct-1-yn-1-yl)(phenyl)silane 4s

A 500 mL oven-dried Schlenk flask equipped with a stir bar and stoppered with a rubber septum was evacuated and refilled once with argon. NaOH (364 mg, 9.1 mmols, 10 mol %) was weighed out on the bench and added to the flask under a strong flow of argon. The charged flask was then evacuated and heated under vacuum for 2 minutes with a heat gun, then refilled with argon. 1,2-dimethoxyethane (DME) (degassed, 90 mL), 1-octyne (13.4 mL, 90.7 mmol, 1.0 equiv) and $PhMe_2SiH$ (20.9 mL, 136.1 mmol, 1.5 equiv) were added through the septum by syringe. The flask was then heated with a heating mantle set at 45° C. and stirred for 60 hours. The flask with the resultant cloudy brown-tan solution was removed from heating and allowed to cool to room temperature, diluted with anhydrous $Et_2O$ (50 mL), and filtered through a short pad of silica to remove solid residue. After the solvent was removed in vacuo, a stirbar was added and the transparent deep amber solution was stirred under high vacuum (100 millitorr) for several hours to remove remaining volatiles. The mixture was then subjected to distillation under vacuum:

a) Heating bath to 80 OC, vacuum stabilizes at 200 millitorr as a small amount of droplets condense into the forerun. Forerun comes off as a colorless liquid. Thermometer reads 22° C.
b) Vacuum stays at 200 millitorr. Heating bath set to 85° C. as the last of the remaining silane boils off.
c) Heating bath temperature increased to 125° C. The solution starts to boil slowly. Thermometer reads 60° C. Vacuum stays at 200 millitorr.
d) Increase temperature to 130° C., vacuum at 200 millitorr to distill over the desired dimethyl(oct-1-yn-1-yl)

(phenyl)silane (colorless oil). Thermometer reads 85° C. The desired product 4s is obtained as a colorless oil (19.0 g, 86% yield).

Example 3.3

Synthesis of mono- and bis-silylated diynes

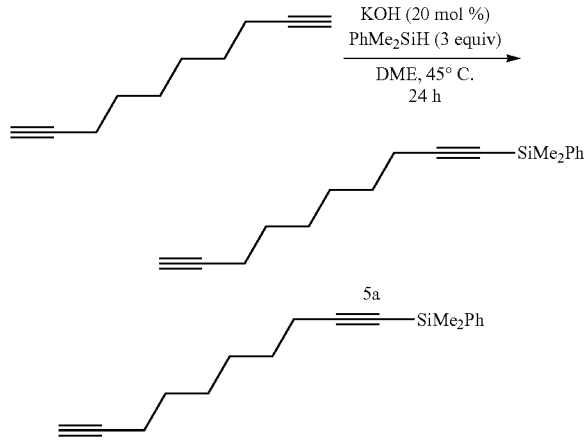

Deca-1,9-diyn-1-yldimethyl(phenyl)silane 5a

The general procedure was followed. The reaction was performed with KOH (5.6 mg, 0.1 mmol, 20 mol %), deca-1,9-diyne (67 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 45° C. for 24 h. The desired product 5a (126.2 mg, 94% yield) was obtained in 95% purity after solvent removal at 85° C. at 45 mtorr for 20 minutes; subsequent purification by silica gel flash chromatography (100% hexanes) yielded the product 5a in analytically pure form as a colorless oil. R$_f$=0.48 (100% hexanes); $^1$H NMR (500 MHz, CDCl$_3$) δ 7.66-7.61 (m, 2H), 7.40-7.35 (m, 3H), 2.29 (t, J=7.1 Hz, 2H), 2.20 (td, J=7.1, 2.6 Hz, 2H), 1.96 (t, J=2.6 Hz, 1H), 1.57 (dtd, J=9.6, 7.1, 4.5 Hz, 4H), 1.47-1.42 (m, 4H), 0.40 (s, 6H); $^{13}$C NMR (126 MHz, CDCl$_3$) δ 137.79, 133.78, 129.37, 127.93, 109.55, 84.74, 82.51, 68.34, 28.51, 28.45, 28.39, 28.31, 20.04, 18.48, −0.46. IR (Neat Film NaCl) 3420, 3306, 3068, 2936, 2859, 2173, 2117, 1646, 1457, 1428, 1325, 1248, 1114, 1026, 836, 816, 754, 731, 700, 661 cm$^{-1}$; HRMS (EI+) calc'd for C$_{18}$H$_{23}$Si [(M+H)−H$_2$]: 267.1569, found 267.1556.

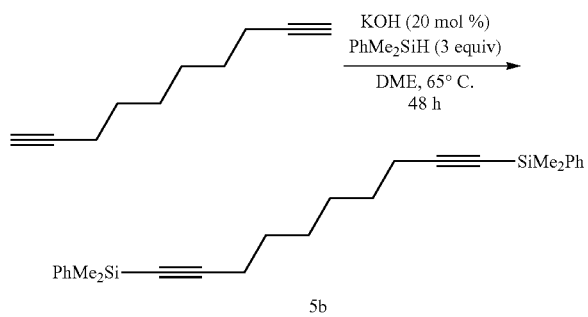

1,10-Bis(dimethyl(phenyl)silyl)deca-1,9-diyne 5b

The general procedure was followed. The reaction was performed with KOH (5.6 mg, 0.1 mmol, 20 mol %), deca-1,9-diyne (67 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 65° C. for 48 h. The desired product 5b (190.9 mg, 95% yield) was obtained in 95% purity after solvent removal at 85° C. at 45 mtorr for 30 minutes; subsequent purification by silica gel flash chromatography (100% hexanes) yielded the product 5b in analytically pure form as a colorless oil. R$_f$=0.43 (100% hexanes); $^1$H NMR (500 MHz, CDCl$_3$) δ 7.65 (ddt, J=5.4, 3.0, 1.4 Hz, 4H), 7.38 (ddt, J=4.4, 2.2, 1.1 Hz, 6H), 2.30 (td, J=7.2, 1.1 Hz, 4H), 1.59 (t, J=6.8 Hz, 4H), 1.49-1.42 (m, 4H), 0.43-0.40 (s, 12H); $^{13}$C NMR (126 MHz, CDCl$_3$) δ 137.79, 133.78, 129.37, 127.93, 109.58, 82.49, 28.53, 28.38, 20.04, −0.45. IR (Neat Film NaCl) 3423, 3068, 2937, 2858, 2173, 1647, 1428, 1248, 1114, 836, 815, 753, 730, 699, 661 cm$^{-1}$; HRMS (EI+) calc'd for C$_{26}$H$_{33}$Si$_2$ [(M+H)−H$_2$]: 401.2121, found 401.2120.

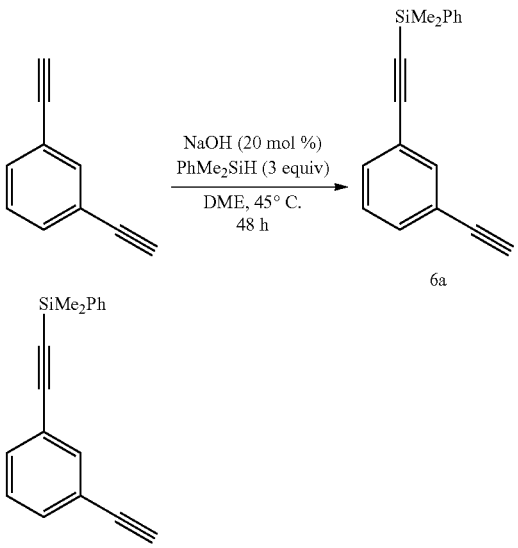

((3-Ethynylphenyl)ethynyl)dimethyl(phenyl)silane 6a

The general procedure was followed. The reaction was performed with NaOH (4.0 mg, 0.1 mmol, 20 mol %), 1,3-diethynylbenzene (63 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 45° C. for 48 h. The desired product 6a (99.2 mg, 76% yield) was obtained as a colorless oil after solvent removal at 85° C. at 45 mtorr for 30 minutes and subsequent purification by silica gel flash chromatography (100% hexanes→3% EtOAc in hexanes).

R$_f$=0.27 (100% hexanes); $^1$H NMR (500 MHz, CDCl$_3$) δ 7.70-7.68 (m, 2H), 7.64 (t, J=1.6 Hz, 1H), 7.46 (ddt, J=14.2, 7.8, 1.4 Hz, 2H), 7.41 (dd, J=4.9, 1.9 Hz, 3H), 7.29 (dd, J=7.7, 0.6 Hz, 1H), 3.09 (s, 1H), 0.51 (d, J=0.5 Hz, 6H); $^{13}$C NMR (126 MHz, CDCl$_3$) δ 136.86, 135.71, 133.86, 132.38, 132.35, 129.66, 128.48, 128.09, 123.43, 122.51, 105.63, 93.20, 82.78, 77.99, −0.75. IR (Neat Film NaCl) 3294, 2950, 2152, 1474, 1428, 1249, 1118, 924, 838, 818, 781, 731, 698 cm$^{-1}$; HRMS (EI+) calc'd for C$_{18}$H$_{17}$Si [M+H]: 261.1100. found 261.1093.

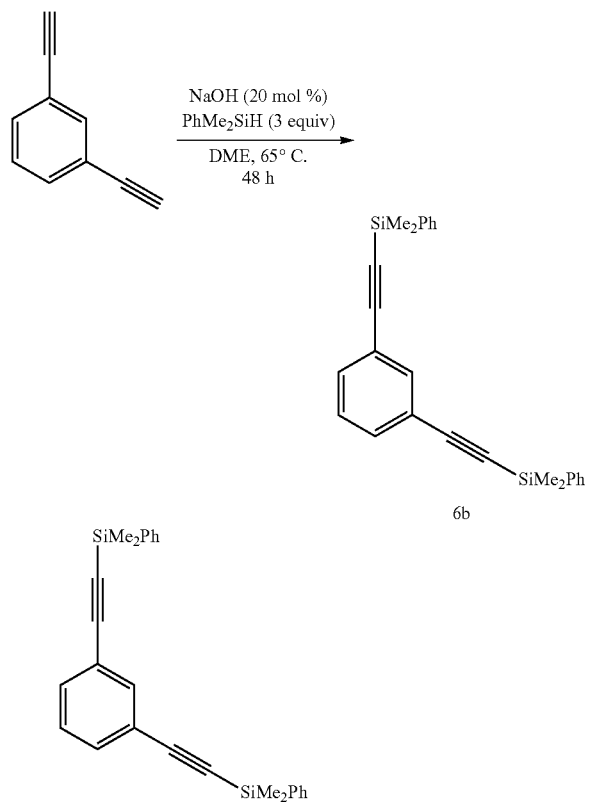

1,3-bis((dimethyl(phenyl)silyl)ethynyl)benzene 6b

The general procedure was followed. The reaction was performed with NaOH (4.0 mg, 0.1 mmol, 20 mol %), 1,3-diethynylbenzene (63 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 65° C. for 48 h. The desired product 6b (173.5 mg, 88% yield) was obtained in 95% purity after solvent removal at 85° C. at 45 mtorr for 30 minutes; subsequent purification by silica gel flash chromatography (100% hexanes→3% EtOAc in hexanes) yielded the product 6b in analytically pure form as a light yellow oil. R$_f$=0.26 (100% hexanes); $^1$H NMR (500 MHz, CDCl$_3$) δ 7.73-7.70 (m, 4H), 7.69 (t, J=1.7 Hz, 1H), 7.47 (dd, J=7.8, 1.7 Hz, 2H), 7.44-7.41 (m, 6H), 7.28 (ddd, J=8.0, 7.4, 0.5 Hz, 1H), 0.53 (s, 12H); $^{13}$C NMR (126 MHz, CDCl$_3$) δ 136.88, 135.69, 133.86, 132.23, 129.64, 128.40, 128.08, 123.33, 105.73, 93.08, −0.74. IR (Neat Film NaCl) 3068, 2959, 2153, 1589, 1474, 1428, 1405, 1249, 1164, 1118, 944, 838, 816, 780, 753, 730, 702, 685 cm$^{-1}$; HRMS (EI+) calc'd for C$_{26}$H$_{27}$Si$_2$ [M+H]: 395.1651, found 395.1659.

Example 3.4

Synthesis of Symmetric and Unsymmetric Diethynylsilanes

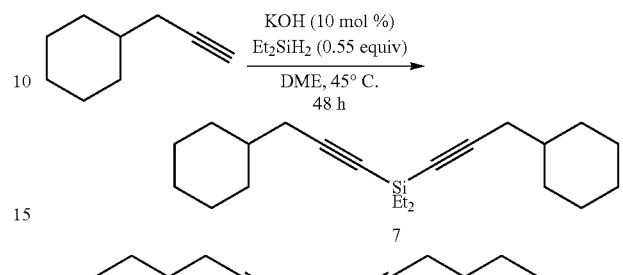

Bis(3-cyclohexylprop-1-yn-1-yl)diethylsilane 7

The general procedure was followed. The reaction was performed with KOH (2.8 mg, 0.05 mmol, 10 mol %), cyclohexylpropyne (61 mg, 0.5 mmol, 1.0 equiv), Et$_2$SiH$_2$ (24 mg, 36 μL, 0.275 mmol, 0.55 equiv), and 0.5 mL of tetrahydrofuran (THF) at 45° C. for 48 h. The desired product 7 (125.0 mg, 76% yield) was obtained in 90% purity after solvent removal under high vacuum at 45 mtorr for 30 minutes; subsequent purification by silica gel flash chromatography (100% hexanes) yielded the product 7 as a colorless oil. R$_f$=0.51 (100% hexanes); $^1$H NMR (500 MHz, CDCl$_3$) δ 2.15 (d, J=6.6 Hz, 4H), 1.81 (ddd, J=13.6, 4.0, 1.8 Hz, 4H), 1.72 (dt, J=12.7, 3.2 Hz, 4H), 1.65 (dddt, J=12.7, 5.1, 3.3, 1.5 Hz, 2H), 1.49 (dddt, J=14.6, 8.0, 6.7, 3.2 Hz, 2H), 1.25 (qt, J=12.7, 3.4 Hz, 4H), 1.15 (tt, J=12.6, 3.2 Hz, 4H), 1.05 (t, J=7.8 Hz, 6H), 1.03-0.98 (m, 2H), 0.67 (q, J=7.8 Hz, 4H). $^{13}$C NMR (126 MHz, CDCl$_3$) δ 108.03, 80.73, 37.36, 32.76, 27.95, 26.43, 26.29, 7.47, 7.02. IR (Neat Film NaCl) 2923, 2873, 2852, 2175, 1448, 1031, 725, 688 cm$^{-1}$; HRMS (EI+) calc'd for C$_{22}$H$_{37}$Si [M+H]: 329.2665, found 329.2661.

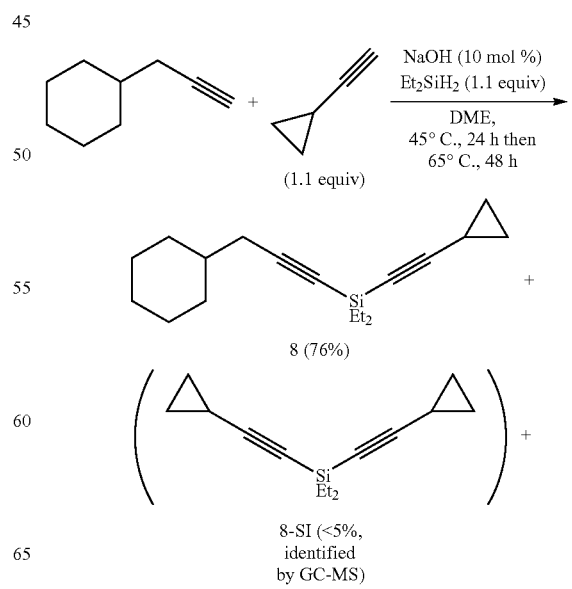

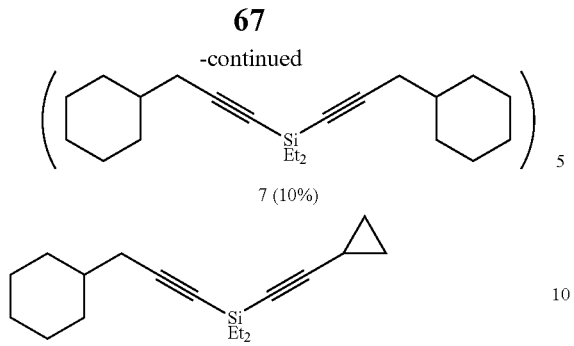

7 (10%)

(3-Cyclohexylprop-1-yn-1-yl)(cyclopropylethynyl)diethylsilane 8

The general procedure was followed. The reaction was performed with NaOH (2.0 mg, 0.05 mmol, 10 mol %), cyclohexylpropyne (61 mg, 0.5 mmol, 1.0 equiv), cyclopropylacetylene (36 mg, 0.55 mmol, 1.1 equiv), Et$_2$SiH$_2$ (49 mg, 71 μL, 0.55 mmol, 1.1 equiv), and 0.5 mL of 1,2-dimethoxyethane (DME) at 45° C. for 24 h, then 65° C. for 48 h. The desired product 8 (102.8 mg, 76% yield) was obtained in 90% purity after solvent removal under high vacuum at 45 mtorr for 30 minutes; subsequent purification by silica gel flash chromatography (100% hexanes) yielded the product 8 as a colorless oil. Also isolated was 10% yield of the homocoupled 3-cyclohexyl-1-propyne product 7; <5% of the homocoupled cyclopropylacetylene 8-SI was identified by GC-MS. This same product 8 can be achieved in comparable yield (106.4 mg, 78% yield) in a 2-step process by first isolating the silylated cyclohexylpropyne 2e and then combining this pre-silylated product with cyclopropylacetylene (1.1 equiv) and NaOH (10 mol %). $R_f$=0.34 (100% hexanes); $^1$H NMR (500 MHz, CDCl$_3$) δ 2.14 (d, J=6.6 Hz, 2H), 1.83-1.77 (m, 2H), 1.71 (dt, J=12.7, 3.2 Hz, 2H), 1.65 (dddt, J=12.8, 5.1, 3.3, 1.5 Hz, 1H), 1.48 (ddtd, J=15.0, 11.6, 6.8, 3.6 Hz, 1H), 1.33-1.28 (m, 1H), 1.28-1.19 (m, 2H), 1.13 (qt, J=12.8, 3.3 Hz, 1H), 1.03 (t, J=7.9 Hz, 6H), 1.01-0.95 (m, 2H), 0.81-0.73 (m, 4H), 0.65 (q, J=7.9 Hz, 4H); $^{13}$C NMR (126 MHz, CDCl$_3$) δ 111.83, 108.11, 80.57, 75.08, 37.34, 32.76, 27.94, 26.41, 26.27, 8.98, 7.43, 6.98, 0.73. IR (Neat Film NaCl) 3422, 3094, 3012, 2955, 1923, 2852, 2174, 2105, 1641, 1449, 1424, 1376, 1348, 1322, 1275, 1232, 1130, 1073, 1052, 1028, 979, 891, 873, 828, 779, 725, 688, 642 cm$^{-1}$; HRMS (EI+) calc'd for C$_{18}$H$_{29}$Si [M+H]: 273.2039, found 273.2025.

Example 3.5

Late-Stage Silylation of Pharmaceuticals

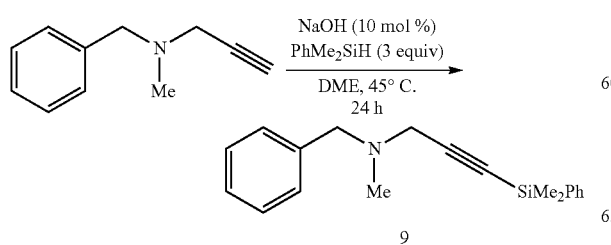

9

N-benzyl-3-(dimethyl(phenyl)silyl)-N-methylprop-2-yn-1-amine 9

The general procedure was followed. The reaction was performed with NaOH (2.0 mg, 0.05 mmol, 10 mol %), Pargyline (N-benzyl-N-methylprop-2-yn-1-amine) (80 mg, 0.5 mmol, 1.0 equiv), PhMe$_2$SiH (204 mg, 230 μL, 1.5 mmol, 3.0 equiv), and 0.5 mL of 1,2-dimethoxyethane (DME) at 45° C. for 24 h. The desired product 9 (140.4 mg, 96% yield) was obtained as a pale yellow oil after solvent removal at 85° C. at 45 mtorr for 30 minutes. $^1$H NMR (500 MHz, CDCl$_3$) δ 7.69 (dq, J=6.8, 3.4, 2.7 Hz, 2H), 7.40 (dt, J=4.3, 2.1 Hz, 3H), 7.35-7.31 (m, 4H), 7.30-7.26 (m, 1H), 3.60 (d, J=3.0 Hz, 2H), 3.38 (d, J=3.1 Hz, 2H), 2.38 (d, J=3.2 Hz, 3H), 0.47 (d, J=3.4 Hz, 6H); $^{13}$C NMR (126 MHz, CDCl$_3$) δ 138.47, 137.34, 133.82, 129.54, 129.39, 128.45, 128.01, 127.35, 102.95, 88.41, 60.17, 46.08, 42.09, -0.49. IR (Neat Film NaCl) 3067, 3026, 2958, 2793, 2162, 1494, 1453, 1428, 1366, 1249, 1115, 1026, 980, 837, 817, 780, 732, 698 cm$^{-1}$; HRMS (EI+) calc'd for C$_{19}$H$_{24}$NSi [M+H]: 294.1678, found 294.1689.

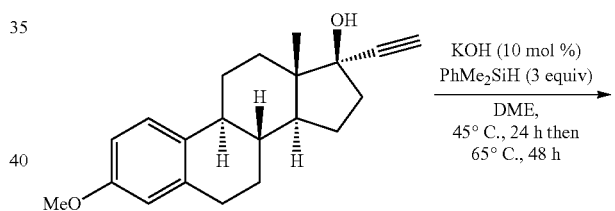

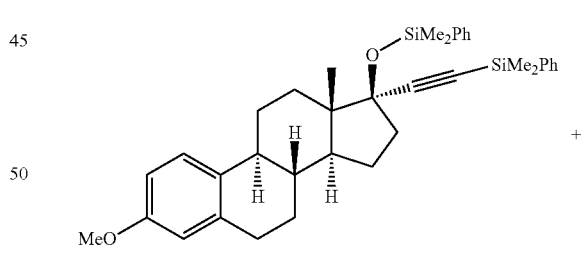

10a

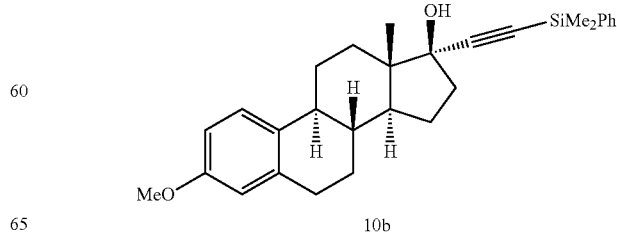

10b

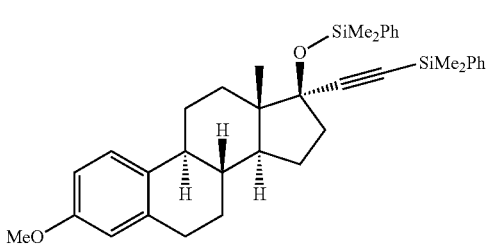

(((8R,9S,13S,14S,17S)-17-((dimethyl(phenyl)silyl)ethynyl)-3-methoxy-13-methyl-7,8,9,11,12,13,14,15,16,17-decahydro-6H-cyclopenta[a]phenanthren-17-yl)oxy)dimethyl (phenyl)silane 10a The general procedure was followed. The reaction was performed with KOH (2.8 mg, 0.05 mmol, 10 mol %), mestranol ((8R,9S,13S,14S,17R)-17-ethynyl-3-methoxy-13-methyl-7,8,9,11,12,13,14,15,16,17-decahydro-6H-cyclopenta[a]phenanthren-17-ol) (155 mg, 0.5 mmol, 1.0 equiv), PhMe$_2$SiH (204 mg, 230 µL, 1.5 mmol, 3.0 equiv), and 0.5 mL of 1,2-dimethoxyethane (DME) at 45° C. for 24 h then 65° C. for 48 h. The product 10a (185.5 mg, 64% yield) was obtained as a colorless oil by silica gel flash chromatography (1%→5% EtOAc in hexanes). R$_f$=0.50 (5% EtOAc in hexanes); $^1$H NMR (500 MHz, THF-d8) δ 7.62-7.56 (m, 4H), 7.30 (dtq, J=9.6, 5.1, 2.2 Hz, 6H), 7.16 (d, J=8.6 Hz, 1H), 6.63 (dd, J=8.5, 2.7 Hz, 1H), 6.59-6.55 (m, 1H), 3.69 (d, J=1.0 Hz, 3H), 2.88-2.75 (m, 2H), 2.42-2.23 (m, 2H), 2.18 (qd, J=10.8, 10.1, 3.5 Hz, 2H), 2.11-1.95 (m, 2H), 1.94-1.85 (m, 1H), 1.83-1.74 (m, 2H), 1.54-1.38 (m, 4H), 1.34 (ddt, J=24.2, 12.3, 5.9 Hz, 1H), 0.94 (d, J=2.0 Hz, 3H), 0.52-0.43 (m, 6H), 0.38-0.32 (m, 6H). $^{13}$C NMR (126 MHz, THF-d8) δ 158.87, 140.78, 138.42, 134.65, 134.38, 133.09, 130.31, 129.98, 128.73, 128.45, 127.12, 114.47, 112.88, 112.37, 90.44, 82.68, 55.34, 51.46, 49.86, 45.16, 41.66, 40.95, 34.17, 30.86, 28.64, 27.69, 24.01, 17.10, 13.81, 1.44, −0.61. IR (Neat Film NaCl) 3417, 3068, 3048, 2946, 2869, 2234, 2160, 2081, 1610, 1575, 1500, 1465, 1427, 1279, 1252, 1136, 1117, 1088, 1045, 929, 886, 818, 783, 730, 699, 642 cm$^{-1}$; HRMS (EI+) calc'd for C$_{37}$H$_{47}$O$_2$Si$_2$ [M+H]: 579.3115, found 579.3109.

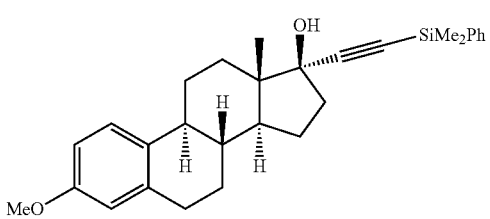

(8R,9S,13S,14S,17S)-17-((dimethyl(phenyl)silyl)ethynyl)-3-methoxy-13-methyl-7,8,9,11,12,13,14,15,16,17-decahydro-6H-cyclopenta[a]phenanthren-17-ol 10b The desired product 10b (40.0 mg, 18% yield) was also obtained from this reaction as a white solid foam by silica gel flash chromatography (1%→5% EtOAc in hexanes) in a 9:1 mixture with 10a. R$_f$=0.39 (5% EtOAc in hexanes); $^1$H NMR (500 MHz, THF-d8) δ 7.62-7.56 (m, 2H), 7.32-7.27 (m, 3H), 7.05 (dd, J=8.8, 0.9 Hz, 1H), 6.60 (dd, J=8.5, 2.8 Hz, 1H), 6.57 (d, J=2.7 Hz, 1H), 5.68 (s, 1H), 3.71 (s, 3H), 2.82-2.78 (m, 2H), 2.33-2.26 (m, 1H), 2.24-2.16 (m, 3H), 2.00 (ddd, J=13.3, 11.9, 4.1 Hz, 1H), 1.90-1.81 (m, 3H), 1.68-1.60 (m, 1H), 1.40-1.27 (m, 4H), 0.91 (s, 3H), 0.44 (d, J=1.5 Hz, 6H); $^{13}$C NMR (126 MHz, THF-d8) δ 158.91, 140.86, 138.41, 134.21, 132.92, 130.05, 128.59, 127.30, 114.45, 112.45, 91.04, 82.87, 55.37, 49.97, 48.26, 45.20, 40.94, 40.81, 37.16, 34.18, 30.91, 28.64, 27.77, 24.00, 14.21, 1.45. IR (Neat Film NaCl) 3421, 2932, 2869, 1609, 1500, 1464, 1427, 1979, 1253, 1138, 1117, 1099, 1035, 888, 829, 783, 742, 699 cm$^{-1}$; HRMS (EI+) calc'd for C$_{29}$H$_{37}$O$_2$Si [M+H]: 445.2563, found 445.2575.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

What is claimed:

1. A method comprising contacting at least one organic substrate comprising a terminal alkynyl C—H bond, with a mixture of at least one organosilane and an alkali metal hydroxide, under conditions sufficient to form a silylated terminal alkynyl moiety, wherein the method forms the silylated terminal alkynyl moiety.

2. The method of claim 1, wherein at least one organosilane comprises an organosilane of Formula (I), Formula (II), or Formula (III):

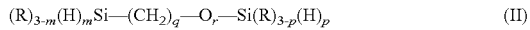

where: m and p are independently 1, 2, or 3; q is 0, 1, 2, 3, 4, 5, or 6; r is 0 or 1; n is 10 to 100; and each R is independently F, Br, Cl, or I, provided at least one R contains carbon, optionally substituted C$_{1-12}$ alkyl or C$_{1-12}$ heteroalkyl, optionally substituted C$_{2-12}$ alkenyl or C$_{2-12}$ heteroalkenyl, optionally substituted C$_{2-12}$ alkynyl or heteroalkynyl, optionally substituted C$_{6-20}$ aryl or C$_{3-20}$ heteroaryl, optionally substituted C$_{7-30}$ alkaryl or C$_{6-30}$ heteroalkaryl, optionally substituted C$_{7-30}$ aralkyl or C$_{5-30}$ heteroaralkyl, optionally substituted —O—C$_{1-12}$ alkyl or —O—C$_{1-12}$ heteroalkyl, optionally substituted —O—C$_{6-20}$ aryl or —O—C$_{3-20}$ heteroaryl, optionally substituted —O—C$_{7-30}$ alkaryl or —O—C$_{5-30}$ heteroalkaryl, or optionally substituted —O—C$_{7-30}$ aralkyl or —O—C$_{5-30}$ heteroaralkyl, and, if substituted, the substituents may be phosphonato, phosphoryl, phosphanyl, phosphino, sulfonato, C$_1$-C$_{20}$ alkylsulfanyl, C$_{6-20}$ arylsulfanyl, C$_1$-C$_{20}$ alkylsulfonyl, C$_{6-20}$ arylsulfonyl, C$_1$-C$_{20}$ alkylsulfinyl, C$_{6-20}$ arylsulfinyl, sulfonamido, amino, amido, imino, nitro, nitroso, hydroxyl, C$_1$-C$_{20}$ alkoxy, C$_{6-20}$ aryloxy, C$_2$-C$_{20}$ alkoxycarbonyl, C$_{6-20}$ aryloxycarbonyl, carboxyl, carboxylato, mercapto, formyl, C$_1$-C$_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents optionally provide a tether to an insoluble or sparingly soluble support media comprising alumina, silica, or carbon.

3. The method of claim 2, wherein the organosilane is $(R)_3SiH$, $(R)_2SiH_2$, or $(R)SiH_3$, where R is independently alkoxy, alkyl, alkenyl, aryl, aryloxy, heteroaryl, aralkyl, or heteroaralkyl.

4. The method of claim 1, wherein the alkali metal hydroxide is sodium hydroxide (NaOH).

5. The method of claim 4, wherein the at least one organosilane is $EtMe_2SiH$, $(n-Bu)_3SiH$, $Et_2SiH_2$, $PhMe_2SiH$, $BnMe_2SiH$, $(EtO)_3SiH$, $Me_2(pyridinyl)SiH$, or $Me_3Si—SiMe_2H$.

6. The method of claim 1, wherein the alkali metal hydroxide is potassium hydroxide (KOH).

7. The method of claim 6, wherein the at least one organosilane is $EtMe_2SiH$, $PhMe_2SiH$, $(n-Bu)_3SiH$, $Et_2SiH_2$, $(i-Pr)_3SiH$, or $(i-Pr)_2(pyridinyl)SiH$.

8. The method of claim 1, wherein the at least one organic substrate comprising the terminal alkynyl C—H bond has a formula:

$$R^1—C≡C—H,$$

where $R^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene.

9. The method of claim 8, wherein $R^1$ comprises:
(a) an optionally substituted linear alkyl, an optionally substituted branched alkyl, or an optionally substituted cycloalkyl;
(b) an optionally substituted linear alkenyl, an optionally substituted branched alkenyl, or an optionally substituted cycloalkenyl;
(c) an optionally substituted linear heteroalkyl, an optionally substituted branched heteroalkyl, or an optionally substituted heterocycloalkyl;
(d) an optionally substituted aryl, an optionally substituted aralkyl, optionally substituted heteroaryl, or an optionally substituted heteroaralkyl; or
(e) a combination of two or more of (a) through (d).

10. The method of claim 1, wherein the at least one organic substrate comprising the terminal alkynyl C—H bond is polymeric.

11. The method of claim 1, wherein the at least one organosilane is $(R)_2Si(H)_2$, the method further comprising contacting a second organic substrate having a terminal alkynyl C—H bond with the silylated terminal alkynyl moiety to form a di- or tri-alkynyl cross-coupled silane product.

12. The method of claim 1, further comprising polymerizing the silylated terminal alkynyl moiety.

13. The method of claim 1, further comprising reacting the silylated terminal alkynyl moiety with:
(a) another unsaturated moiety in a [2+2] or [4+2] cycloaddition reaction to form an aromatic, heteroaromatic, cycloalkenyl, or heterocycloalkenyl moiety;
(b) a second, unsaturated organic moiety in a cross-metathesis reaction to form a diolefin or polyolefin product;
(c) an organic azide in a [3+2] azide-alkyne cycloaddition reaction;

(d) hydrogen, water, an alcohol, hydrogen cyanide, hydrogen chloride, dihalogen, or carboxylic acids to give corresponding olefin or alkane, vinyl compounds, or carbonyl compound;
(e) an aromatic halide compound under conditions sufficient to form an alkynyl-arene linkage;
(f) an N-halosuccinimide in the presence of a cationic gold catalyst to produce a terminal alkynyl halide; or
(g) any combination of (a) through (f).

14. The method of claim 1, further comprising removing the silyl group originally added to the terminal alkynyl C—H bond.

15. The method of claim 1, wherein the at least one organosilane comprises an optionally substituted $C_{2-12}$ alkenyl or $C_{2-12}$ heteroalkenyl, such that the silylated terminal alkynyl moiety comprises a silicon bonded optionally substituted $C_{2-12}$ alkenyl or heteroalkenyl, the method further comprising reacting the silylated terminal alkynyl moiety with an alcohol and a catalyst under conditions to result in the intramolecular allylation of the silylated terminal alkynyl moiety.

16. The method of claim 1, wherein the at least one organosilane comprises a 2-pyridinyl group, the method further comprising:
(a) reacting the silylated terminal alkynyl moiety with a copper carbomagnesation catalyst and an optionally substituted aryl magnesium complex or optionally substituted heteroaryl magnesium complex under conditions sufficient to carbomagnesate the silylated terminal alkynyl moiety; and then optionally
(b) reacting the carbomagnesated silylated terminal alkynyl moiety with an optionally substituted aryl iodide or optionally substituted heteroaryl iodide in the presence of a palladium catalyst to form a trisubstituted silylated olefin; and then optionally
(c) reacting the trisubstituted silylated olefin with $BCl_3$ and pinacol under conditions sufficient to borodesilylate the compound, and then optionally
(d) reacting the borodesilylated compound with a second optionally substituted aryl iodide or optionally substituted heteroaryl iodide under conditions suitable to cross-couple the resulting C—B bond and the second optionally substituted aryl iodide or optionally substituted heteroaryl iodide.

17. A chemical composition comprising a mixture of (a) at least one organosilane and (b) an alkali metal hydroxide or alkali metal alkoxide, (c) at least one organic substrate comprising a terminal alkynyl C—H bond, and (d) a silylated terminal alkynyl moiety having a C—Si bond in a position corresponding to the terminal alkynyl C—H bond in the substrate.

18. The chemical composition of claim 17, wherein at least one organosilane comprises an organosilane of Formula (I), Formula (II), or Formula (III):

$$(R)_{4-m}Si(H)_m \quad (I)$$

$$(R)_{3-m}(H)_mSi—(CH_2)_q—O_r—Si(R)_{3-p}(H)_p \quad (II)$$

$$R—[—SiH(R)—O—]_n—R \quad (III)$$

where: m and p are are independently 1, 2, or 3; q is 0, 1, 2, 3, 4, 5, or 6; r is 0 or 1; n is 10 to 100; and each R is independently F, Br, Cl, I, provided at least one R contains carbon, optionally substituted $C_{1-12}$ alkyl or $C_{1-12}$ heteroalkyl, optionally substituted $C_{2-12}$ alkenyl or $C_{2-12}$ heteroalkenyl, optionally substituted $C_{2-12}$ alkynyl or $C_{2-12}$ heteroalkynyl, optionally substituted $C_{6-20}$ aryl or $C_{3-20}$ heteroaryl, optionally substituted $C_{7-30}$ alkaryl or $C_{6-30}$ heteroalkaryl, optionally substituted $C_{7-30}$ aralkyl or $C_{6-30}$ heteroaralkyl, optionally substituted —O—$C_{1-12}$ alkyl or —O—$C_{1-12}$ heteroalkyl, optionally substituted —O—$C_{6-20}$ aryl or —O—$C_{3-20}$ heteroaryl, optionally substituted —O—$C_{7-30}$ alkaryl or heteroalkaryl, or optionally substituted —O—$C_{7-30}$ aralkyl or —O—$C_{5-30}$ heteroaralkyl, and, if substituted, the substituents may be phosphonato, phosphoryl, phosphanyl, phosphino, sulfonato, $C_1$-$C_{20}$ alkylsulfanyl, $C_{6-20}$ arylsulfanyl, $C_1$-$C_{20}$ alkylsulfonyl, $C_{6-20}$ arylsulfonyl, $C_1$-$C_{20}$ alkylsulfinyl, $C_{6-20}$ arylsulfinyl, sulfonamido, amino, amido, imino, nitro, nitroso, hydroxyl, $C_1$-$C_{20}$ alkoxy, $C_{6-20}$ aryloxy, $C_2$-$C_{20}$ alkoxycarbonyl, $C_{6-20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents optionally provide a tether to an insoluble or sparingly soluble support media comprising alumina, silica, or carbon.

19. The chemical composition of claim 18, wherein the alkali metal hydroxide is sodium hydroxide (NaOH) or potassium hydroxide (KOH).

20. The chemical composition of claim 19, wherein the organosilane is $EtMe_2SiH$, $(n-Bu)_3SiH$, $(i-Pr)_3SiH$, $Et_2SiH_2$, $PhMe_2SiH$, $BnMe_2SiH$, $(Me)_2(pyridinyl)SiH$, $(i-Pr)_2(pyridinyl)SiH$, $(EtO)_3SiH$, or $Me_3Si$—$SiMe_2H$.

21. The chemical composition of claim 17, wherein the at least one organic substrate comprising the terminal alkynyl C—H bond has a formula:

$$R^1\text{—}C\equiv C\text{—}H,$$

where $R^1$ comprises H, an optionally substituted alkyl, optionally substituted alkenyl, optionally substituted alkynyl, optionally substituted aryl, optionally substituted heteroalkyl, optionally substituted heteroaryl, optionally substituted aralkyl, optionally substituted heteroaralkyl, or optionally substituted metallocene.

22. The chemical composition of claim 21, wherein $R^1$ comprises:
(a) an optionally substituted linear alkyl, an optionally substituted branched alkyl, or an optionally substituted cycloalkyl;
(b) an optionally substituted linear heteroalkyl, an optionally substituted branched heteroalkyl, or an optionally substituted heterocycloalkyl;
(c) an optionally substituted aryl, an optionally substituted aralkyl, optionally substituted heteroaryl, or an optionally substituted heteroaralkyl; or
(d) a combination of two or more of (a) through (d).

23. The chemical composition of claim 17, comprising at least two different organosilanes.

24. The chemical composition of claim 17, comprising at least two different organic substrates, each comprising a terminal alkynyl C—H bond.

* * * * *